(12) United States Patent
Cho et al.

(10) Patent No.: US 7,318,964 B2
(45) Date of Patent: Jan. 15, 2008

(54) FLUORENE COMPOUNDS CONTAINING VARIOUS FUNCTIONAL GROUPS, POLYMERS THEREOF AND EL ELEMENT USING THE SAME

(75) Inventors: Hyun-Nam Cho, Seoul (KR); Sung Hyun Jung, Seoul (KR); Sang Won Son, Jeollabuk-do (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/135,728

(22) Filed: May 1, 2002

(65) Prior Publication Data

US 2003/0091859 A1    May 15, 2003

(30) Foreign Application Priority Data

May 22, 2001    (KR)    ................................ 2001-28020

(51) Int. Cl.
*C09B 27/00*    (2006.01)
*C09B 31/00*    (2006.01)
*C07C 321/00*    (2006.01)
*C07C 323/00*    (2006.01)
*H01L 1/62*    (2006.01)

(52) U.S. Cl. .................. 428/690; 534/573; 313/504; 313/506

(58) Field of Classification Search ................ 428/690, 428/917; 528/366, 397; 313/504, 507, 503, 313/506, 509; 534/573
See application file for complete search history.

(56) References Cited

U.S. PATENT DOCUMENTS

| | | | |
|---|---|---|---|
| 5,069,975 A * | 12/1991 | Nakada et al. ............... 428/457 |
| 5,801,974 A | 9/1998 | Park ............................ 364/722 |
| 5,807,974 A * | 9/1998 | Kim et al. .................... 528/366 |
| 5,876,864 A | 3/1999 | Kim et al. .................... 428/690 |
| 5,900,327 A * | 5/1999 | Pei et al. ..................... 428/690 |
| 6,169,163 B1 * | 1/2001 | Woo et al. .................... 528/397 |
| 6,605,373 B2 * | 8/2003 | Woo et al. .................... 428/690 |
| 6,800,381 B2 * | 10/2004 | Cho et al. .................... 428/690 |

FOREIGN PATENT DOCUMENTS

| | | | |
|---|---|---|---|
| JP | 56-25465 B2 | 6/1981 |
| JP | 58-177954 | * 10/1983 |
| JP | 58-177954 A | 10/1983 |
| JP | 02-222484 A | 9/1990 |

(Continued)

OTHER PUBLICATIONS

Goodwin et al., "Thermal Behaior of Fluorinated Aromatic Polyethers and Poly(ether ketone)s", American Chemical Society, 30(2), pp. 2764-2774.*

(Continued)

*Primary Examiner*—Milton I. Cano
*Assistant Examiner*—Camie S. Thompson
(74) *Attorney, Agent, or Firm*—Darby & Darby P.C.

(57) ABSTRACT

The present invention relates to fluorene compounds and polymers thereof, having various structures and functional groups, and capable of being used as a luminescent material for organic and polymer-based electro-luminescence (EL) element and other optical element, and to an EL element using the same as a luminescent material.

19 Claims, 3 Drawing Sheets

FOREIGN PATENT DOCUMENTS

| | | |
|---|---|---|
| JP | 3046814 | 2/1991 |
| JP | 08-333569 A | 12/1996 |
| JP | 11-224779 A | 8/1999 |
| JP | 2000-012230 A | 1/2000 |
| JP | 2000-275435 A | 10/2000 |
| JP | 2001-055447 A | 2/2001 |
| WO | WO-00/46321 A1 | 8/2000 |

OTHER PUBLICATIONS

Katsumi Yoshino et al., Synthetic Metals 49-50 (1992) pp. 491-497: "Gel chromism and anomalous luminescence in poly(3-alkylthiophene)".

Gabriele Grem et al., Advanced Materials, 4 (1992) No. 1 pp. 36-37: "Realization of Blue-Light-Emitting Device using Poly(p-phenylene)".

Arno Kraft et al., Angew. Chem. Int. Ed. (1998), 37, pp. 402-428: "Electroluminescent Conjugated Polymers—Seeing Polymers in a New Light".

D. Y. Kim et al., Prog. Polym. Sci. 25 (2000) pp. 1089-1139: "Blue Light emitting polymers".

Mark T. Bernius et al., Advanced Materials, 12 (2000) No. 23 pp. 1737-1750: "Progress with Light-Emitting Polymers".

C. Zhang et al., Synthetic Metals, 62, (1994) pp. 35-40: Blue electroluminescent diodes utilizing blends of poly(p-phenylphenylene vinylene) in poly(9-vinylcarbozole).

M. R. Andersson et al., Macromolecules (1995) 28, pp. 725-7529: "Electroluminescence from Substituted Poly(thiophenes): From Blue to Near-Infrared".

M. Moroni et al., Macromolecules (1994) 27, pp. 562-571: "Rigid Rod Conjugated Polymers for Nonlinear Optics, 1. Characterization and Linear Optical Properties of Poly(aryleneethynylene) Derivatives".

Christoph Weder et al., Macromolecules (1996) 29, pp. 5157-5165: "Efficient Solid-State Photoluminescence in New Poly(2,5-dialkoxy-p-phenyleneethynylene)s".

Christoph Weder et al., Science (1998) 279, pp. 835-837: "Incorporation of Photoluminescent Polarizers into Liquid Crystal Displays".

Kevin Bunten et al., Macromolecules (1994) 29, pp. 2885-2893: "Synthesis, Optical Absorption, Fluorescence, Quantum Efficiency, and Electrical Conductivity Studies of Pyridine/Pyridinium Dialkynyl Organic and Pt(II)-σ-Acetylide Monomers and Polymers".

Yasuyuki Saito et al., Japanese Journal of Applied Physics (1991) vol. 30, No. 9A, pp. 1940-1941: "Deep-Level Transient Spectroscopy Spectra of Drain Current of Si-Implanted GaAs Metal-Semiconductor Field-Effect Transistors Having Large and Small Low-Frequency Oscillations".

Ahn, T. et al. (2001). "Synthesis and Luminescent Properties of Blue Light-emitting Polymers Containing High Electron Affinity and Hold Transporting Group," *Synthetic Metals* 121:1663-1664.

Andreschev, E. A. (Apr. 19, 1983). "Aryl and Diarylethylenes," *Journal Organucheskou Chemie* 775-779.

Carbonneau, C. et al. (1999). "Efficient Syntheses of New Phosphonate Terminated Trialcoxysilane Derived Oligoarylenevinylene Fluorophores," *Tetrahedron Letters* 40(32):5855-5858.

Cho, H. N. et al. (1997). "Control of Band Gaps of Conjugated Polymers by Copolymerization," *Synthetic Metals* 91:293-296.

Corriu, R. J. P. et al. (1996). "Preparation and Optical Properties of Hybrid Sol-gel Systems Containing Doubly Anchored Oligoarylenevinylenes," *Chem. Commun.* 15:1845-1846.

Jung, S. et al. (2000). "Palladium-Catalyzed Direct Synthesis, Photophysical Properties, and Tunable Electroluminescence of Novel Silicon-Based Alternating Copolymers," *Macromolecules* 33:9277-9288.

Kelley, C. J. et al. (1997). "The Synthesis of Bridged Oligophenylenes from Fluorene: Part 1. Terphenyls and Quaterphenyls," *J. Chem. Research* (S):446-447 and (M):2701-2733.

Kim, Y. C. et al. (2001). "Low-Threshold Amplified Spontaneous Emission in a Fluorene-Based Liquid Crystalline Polymer Blend," *Advanced Materials* 13(9):646-649.

Shah, H. et al. (1999). "Synthesis and Opto-electronic Properties of Polynaphthalenes from Bis-*ortho*-diynylarenes," *Polym. Mat. Sci. & Eng. (Am. Chem. Soc., Div. PMSE)* 80:199.

Katsumi Yoshino et al., Synthetic Metals 49-50 (1992) pp. 491-497: "Gel chromism and anomalous luminescence in poly(3-alkylthiophene)", 1992.

Gabriele Grem et al., Advanced Materials, 4 (1992) No. 1 pp. 36-37: "Realization of Blue-Light-Emitting Device using Poly(p-phenylene)", Jan. 1992.

Arno Kraft et al., Angew. Chem. Int. Ed. (1998), 37, pp. 402-428: "Electroluminescent Conjugated Polymers—Seeing Polymers in a New Light", 1998.

D. Y. Kim et al., Prog. Polym. Sci. 25 (2000) pp. 1089-1139: "Blue Light emitting polymers", Jul. 2000.

Mark T. Bernius et al., Advanced Materials, 12 (2000) No. 23 pp. 1737-1750: "Progress with Light-Emitting Polymers", Dec. 2000.

C. Zhang et al., Synthetic Metals, 62, (1994) pp. 35-40: Blue electroluminescent diodes utilizing blends of poly(p-phenylphenylene vinylene) in poly(9-vinylcarbozole), 1994.

M. R. Andersson et al., Macromolecules (1995) 28, pp. 725-7529: "Electroluminescence from Substituted Poly(thiophenes): From Blue to Near-Infrared", Jul. 1995.

M. Moroni et al., Macromolecules (1994) 27, pp. 562-571: "Rigid Rod Conjugated Polymers for Nonlinear Optics, 1. Characterization and Linear Optical Properties of Poly(aryleneethynylene) Derivatives", Dec. 1993.

Christoph Weder et al., Macromolecules (1996) 29, pp. 5157-5165: "Efficient Solid-State Photoluminescence in New Poly(2,5-dialkoxy-p-phenyleneethynylene)s", Dec. 1995.

Christoph Weder et al., Science (1998) 279, pp. 835-837: "Incorporation of Photoluminescent Polarizers into Liquid Crystal Displays", Feb. 1998.

Kevin Bunten et al., Macromolecules (1994) 29, pp. 2885-2893: "Synthesis, Optical Absorption, Fluorescence, Quantum Efficiency, and Electrical Conductivity Studies of Pyridine/Pyridinium Dialkynyl Organic and Pt(II)-σ-Acetylide Monomers and Polymers", Jan. 1996.

Yasuyuki Saito et al., Japanese Journal of Applied Physics (1991) vol. 30, No. 9A, pp. 1940-1941: "Deep-Level Transient Spectroscopy Spectra of Drain Current of Si-Implanted GaAs Metal-Semiconductor Field-Effect Transistors Having Large and Small Low-Frequency Oscillations", Sep. 1991.

\* cited by examiner

FLUORENE COMPOUNDS CONTAINING VARIOUS FUNCTIONAL GROUPS, POLYMERS THEREOF AND EL ELEMENT USING THE SAME

BACKGROUND OF THE INVENTION

1. Field of the Invention

The present invention relates to a new fluorene compounds containing various functional groups and polymers thereof which can be used as organic polymer semiconductor and photo-electronic materials, and especially as a material for electro-luminescence (hereinafter, referred to as "EL"), and to an EL element using the same.

2. Description of the Background Art

Generally, polymers of a polyphenylene vinylene (hereinafter, referred to as "PPV"), of a polythiophene (hereinafter, referred to as "PTh") and of a polyphenylene (refer to *Synth. Met.*, 50 (1-3), P491 (1992) and *Adv Mater.*, 4, p 36 (1992)) are known as organic polymer semiconductor and photoelectronic materials (refer to *Semiconducting Polymers: Chemistry, Physics and Engineering*, Edited by G. Hadziioannou and P. F. van Hutten) WILEY-VCH (2000)) or as a material for polymer EL (refer to *Angew. Chem. Int. Ed.*, 37, p. 402 (1998), *Prog. Polym. Sci.*, 25, p. 1089 (2000) and *Adv. Mater.*, 12, p. 1737 (2000)). At present, studies for these polymer materials have been made, however, these materials have disadvantages in that the final product is not dissolved in an organic solvent. Also, PPV or PTh derivatives which are improved its processability by introducing an appropriate substituent and illuminate lights of blue, green and red colors are known as the materials (refer to *Synth. Met.*, 62, p. 35 (1994), *Adv. Mater.*, 4, p. 36 (1992), and *Macromolecules*, 28, p. 7525 (1995)). However, the fabrication processes for these derivatives are very complex, and they have a problem in stability.

Polymers having an acetylene group are also disclosed (refer to *Macromol. Chem.*, 191, p. 857 (1990), *Macromolecules*, 27, p. 562 (1994), *J. Chem. Soc., Chem. Commun.*, p. 1433 (1995), and *Macromolecules*. 29. P5157 (1996)), and applications for nonlinear optics or for light conductivity, and photoluminescence (hereinafter referred to as "PL") are reported (refer to *Science*, 279, p. 835 (1998)). Also, polymers having a diacetylene group are disclosed (refer to *Prog. Polym. Sci.*, 20, p. 943 (1995), *CHEMTECH*, October, p 32, (1993)), and *Macromolecules*, 29, p. 2885 (1996)). These polymers are more sensitive to heat or light than the polymers of acetylene group and therefore a cross-link reaction can be easily taken place. These polymers can be applied for a material of nonlinear optics, a heat resistant polymer, a polarized PL polymer, and an electric or optically active polymer. Applying the polymers having a novel acetylene or diacetylene group to a material for the EL has patented by the present inventors (U.S. Pat. No. 5,876,864 and Japanese Patent No. 3,046,814).

A fluorene-based polymer emitting blue light has also been reported (refer to *Jpn. J. Appl. Phys.*, 30, p. L1941 (1991)). However, it uses a preparation method that can not be applied to a preparation of a polymer having various conjugated double bonds. The present inventors has solved the above problem and disclosed fluorene-based alternating copolymers for EL element having conjugated double bond (U.S. Pat. No. 5,801,974. However, there are few examples of preparing or applying fluorene-based polymers having various functional groups as polymeric EL materials.

SUMMARY OF THE INVENTION

Therefore, an object of the present invention is to provide fluorene-based compounds containing various functional groups and polymers thereof which can be dissolved in an organic solvent and can be applied for EL and photo-electonic materials, and to provide EL elements using the same.

The object of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
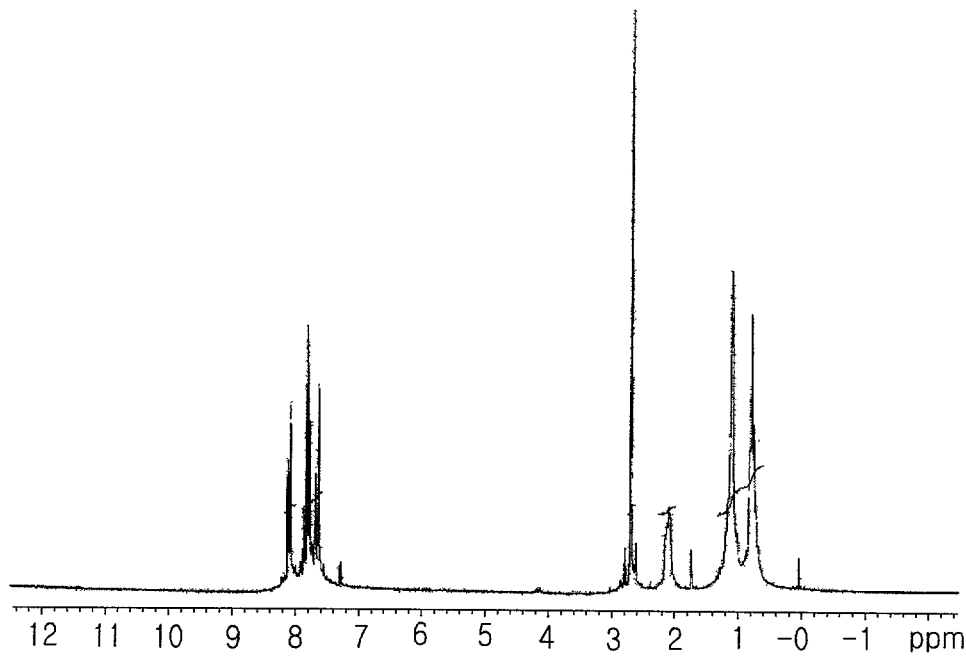
FIG. 1 shows a $^1$H NMR spectrum of the monomer M-34 of Example 34.

Reference will now be made in detail to the preferred embodiments of the present invention, examples of which are illustrated in the accompanying drawings.

The fluorene compound according to the present invention have the following general formula (1):

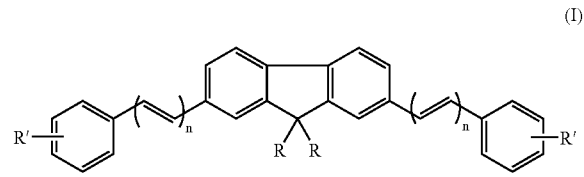

(I)

wherein,

R represents hydrogen, $C_1$-$C_{22}$ aliphatic alkyl or alkoxy, $C_1$-$C_{22}$ alicyclic alkyl or alkoxy, $C_6$-$C_{18}$ aryl or aryloxy, or alkyl or aryl derivatives of silicon, tin, germanium or the like;

R' means a functional group which presents in meta- or para-position of the phenyl group and is not limited to a certain group, and any functional groups can be included if it is easy to be prepared and has good properties; and n represents 0 or 1.

For example, R may be a hydrogen, methyl, ethyl, propyl, isopropyl, butyl, isobutyl, pentyl, hexyl, ethylhexyl, heptyl, octyl, isooctyl, nonyl, decyl, dodecyl, hexadecyl, octadecyl, docodecyl, cyclopropyl, cyclopentyl, cyclohexyl, methoxy, ethoxy, buthoxy, hexyloxy, methoxyethoxyethyl, methoxyethoxyethoxyethyl, phenyl, phenoxy, tolyl, benzyl, naphthyl, anthracene group, trimethylsilyl, triphenylsilyl, tributyltin or triethylgermanium; and R' may be an ether, ester, amine, amide, imide, aldehyde, ketone, sulfone, sulfide, nitro, nitrile, acetylene, halogen, carboxylic acid, boronic acid, vinyl, hydrazide, isocyanate, urethane, carbonate, chloromethyl, hydroxy, anhydride, cyanate, azometine, quinoline, oxadiazole, azo or the like.

The fluorene-based polymer according to the present invention includes polymerization products of the same or different fluorene compounds according to the present invention and polymerization products of the fluorene compounds of the present invention with another organic compound.

The functional groups included in the polymer according to the present invention are not specifically limited, and any functional group can be included if the compound having those functional groups can be prepared easily and has a good EL properties. There may be an ether, ester, amide, imide, ketone, sulfone, sulfides, acetylene, diacetylene, vinyl, hydrazide, urea, urethane, carbonate, azometine, quinoline, oxadiazole, azo group, etc., but, it is not limited therto. To a polymer having a functional group with an atom such as nitrogen (for example, azometine, quinoline, etc.), if an inorganic or organic acid is added, its salt is generated and thereby its UV and maximum PL wavelengths are changed. For example, when hydrochloric acid is added to [P-1] which is an azometine polymer as shown in Reaction Scheme 8, the UV maximum wavelength is changed from 370 nm to 355 nm, and light is emitted at a maximum PL wavelength of 411 nm although the pure [P-1] polymer does not originally show maximum PL wavelength.

The fluorene compounds and polymers thereof of the present invention can be prepared by the following Reaction Schemes 1 to 14:

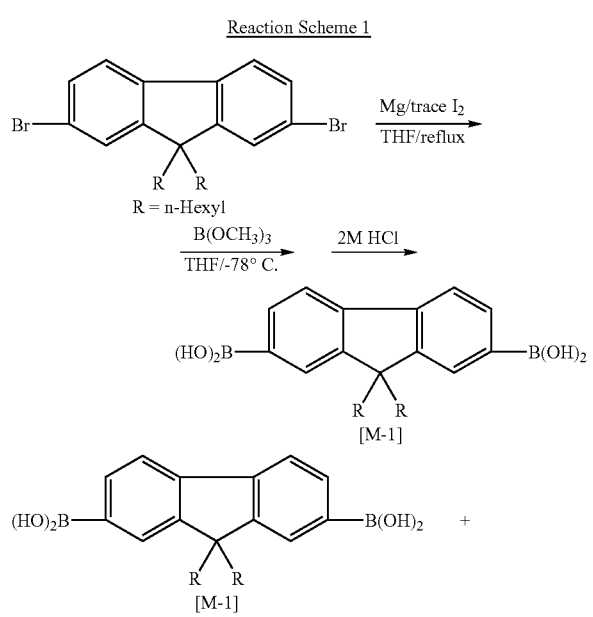

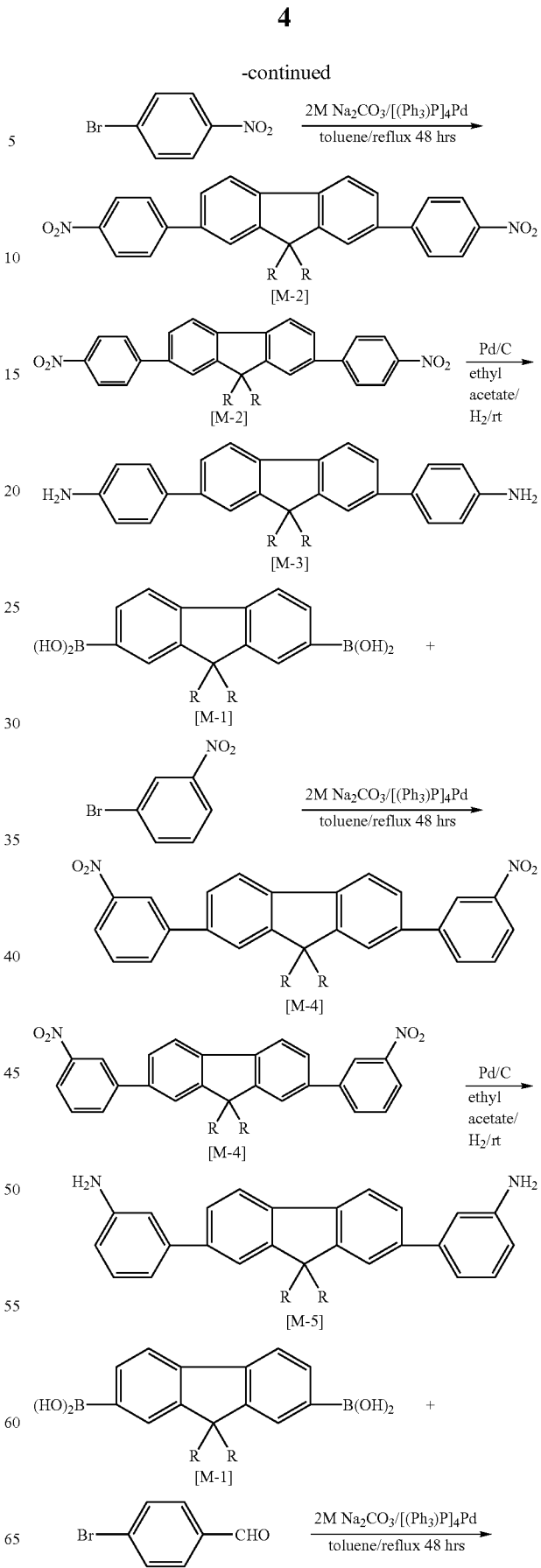

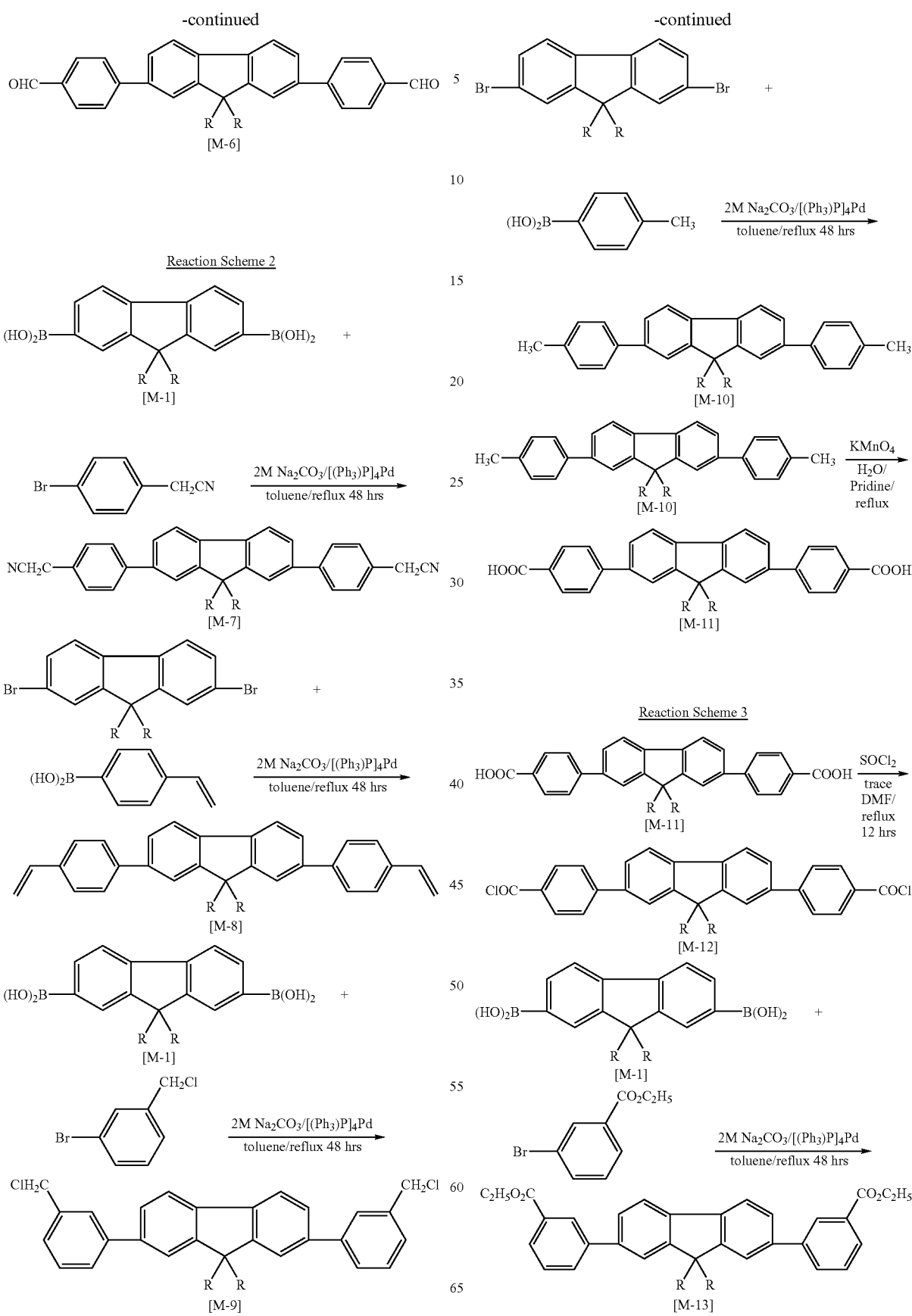

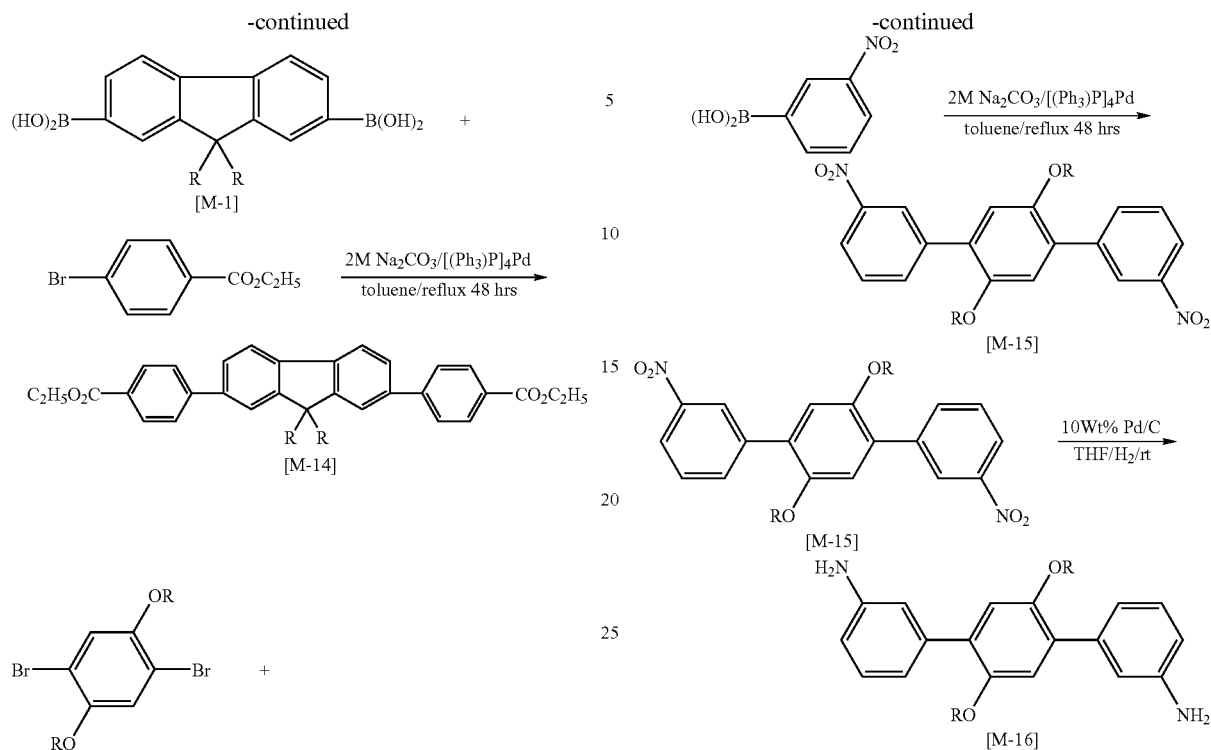
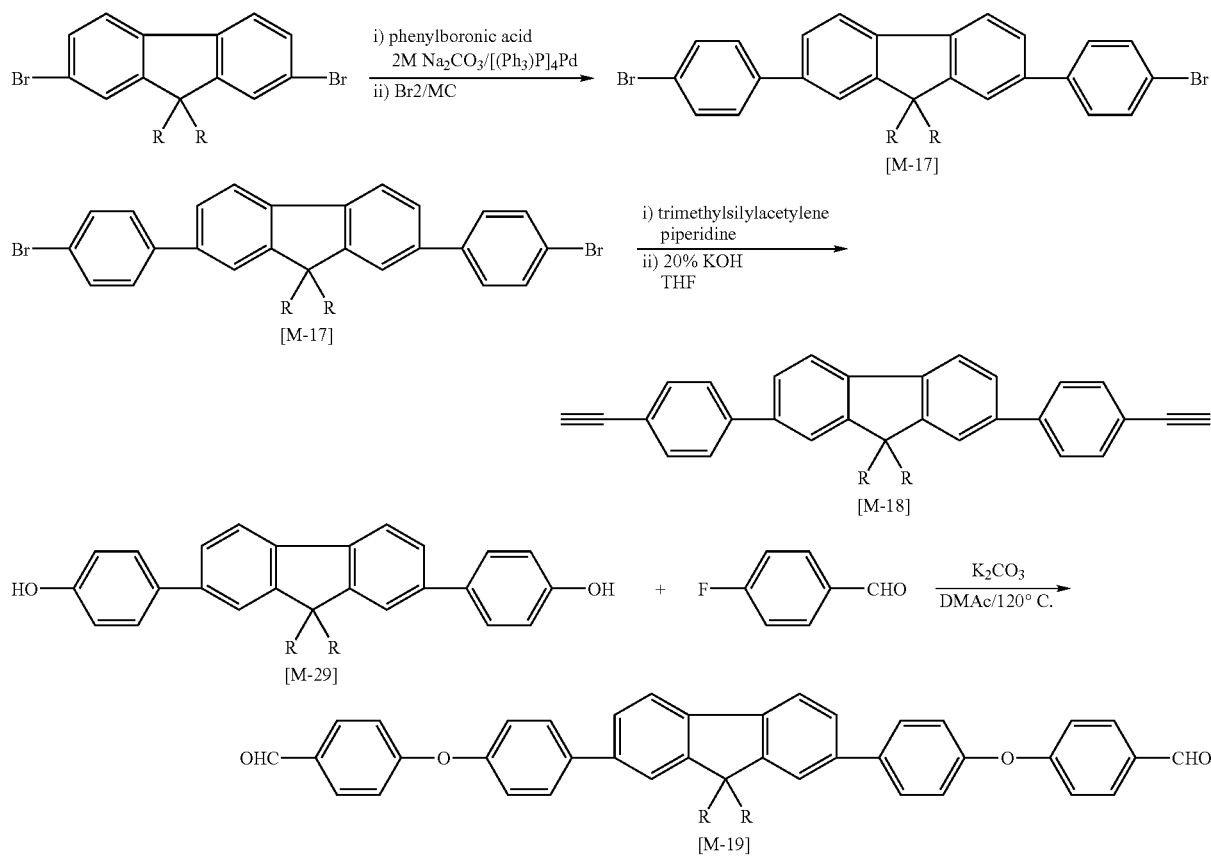
Reaction Scheme 4

-continued
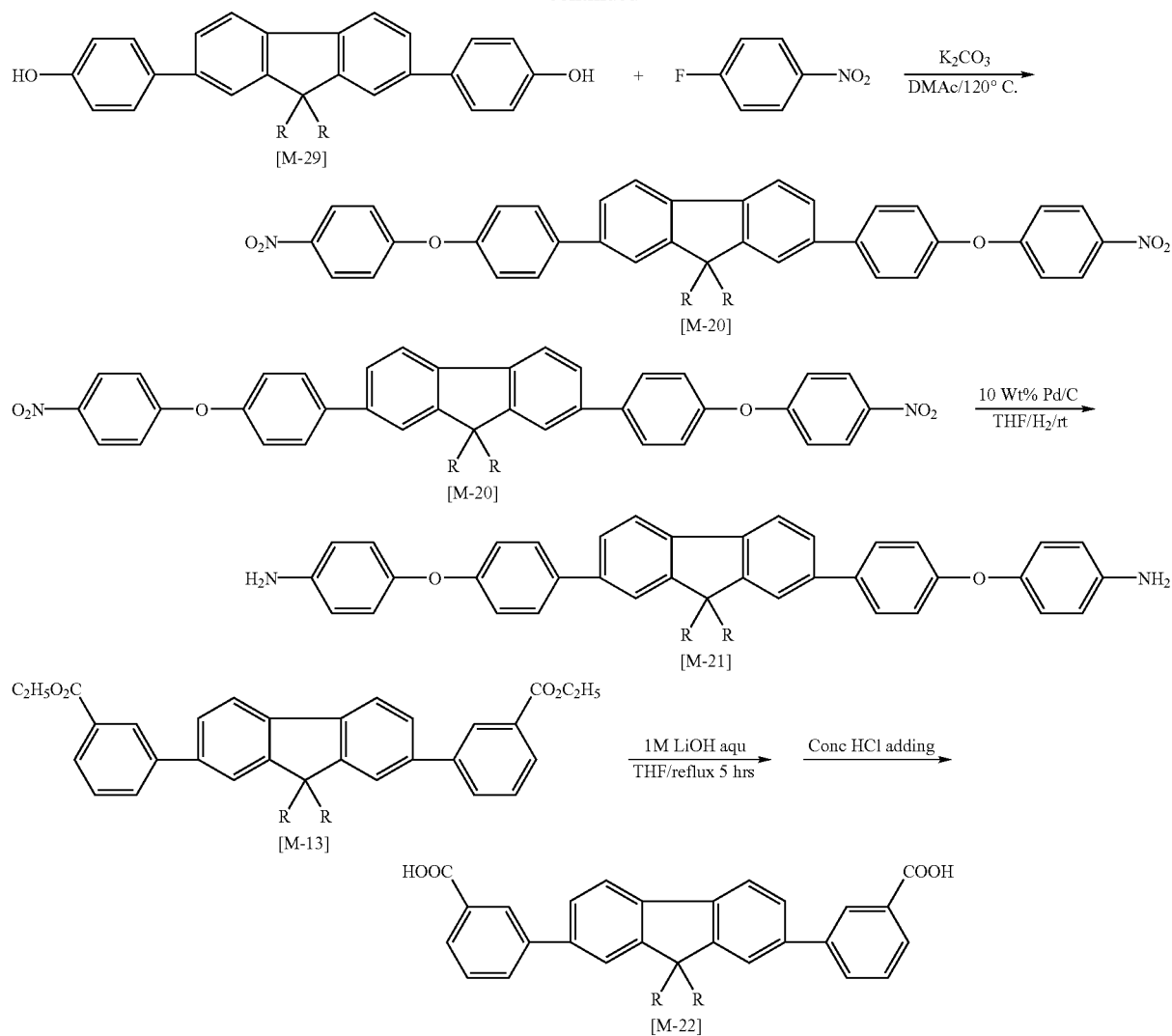
Reaction Scheme 5
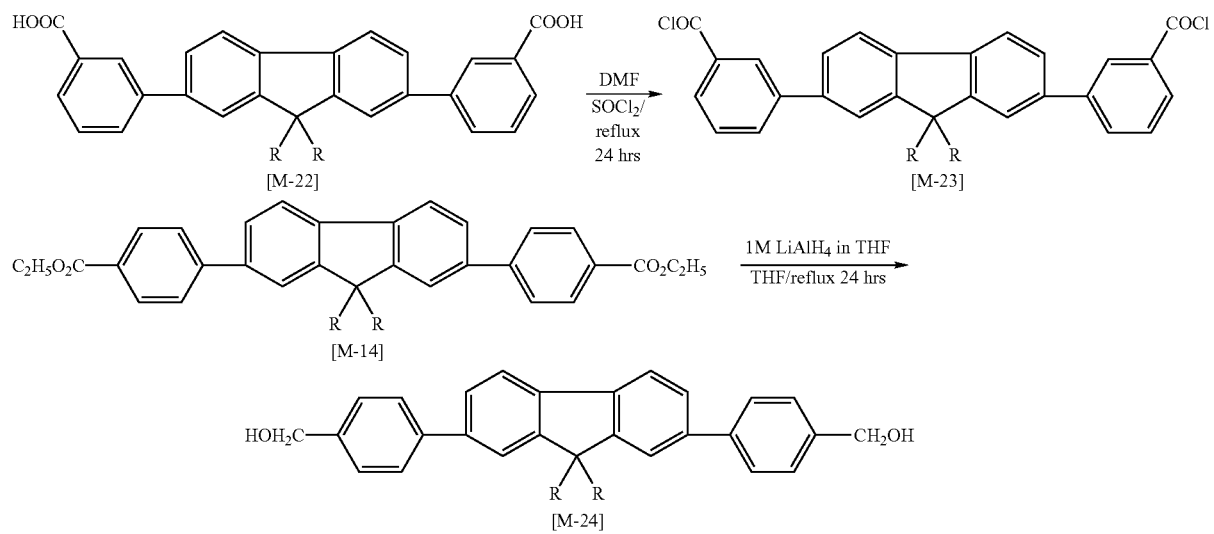

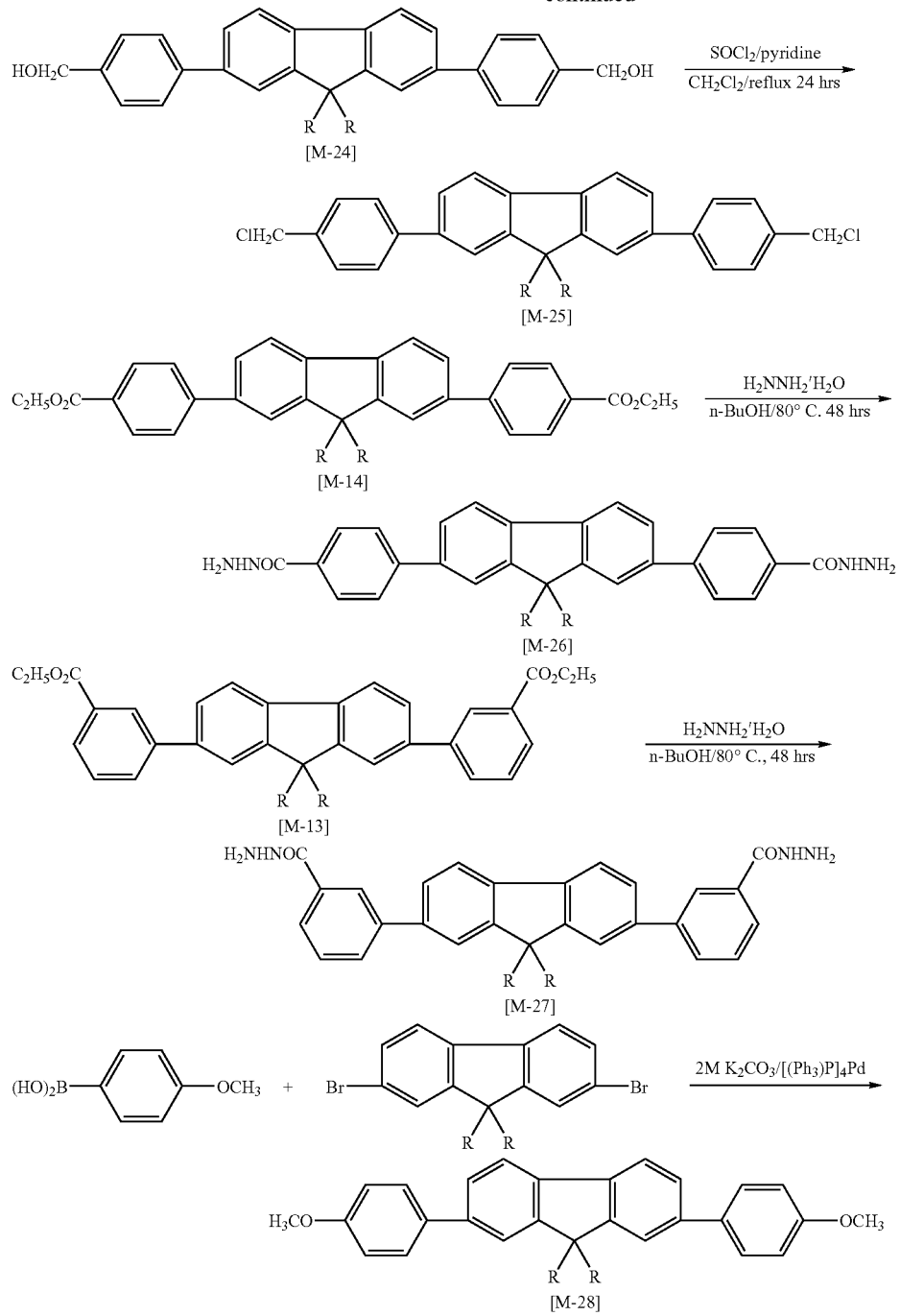
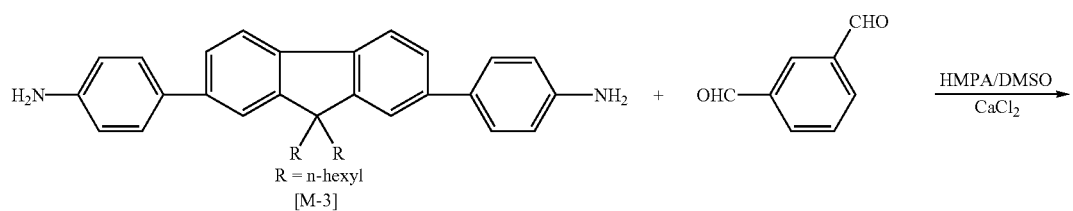
Reaction Scheme 6

-continued
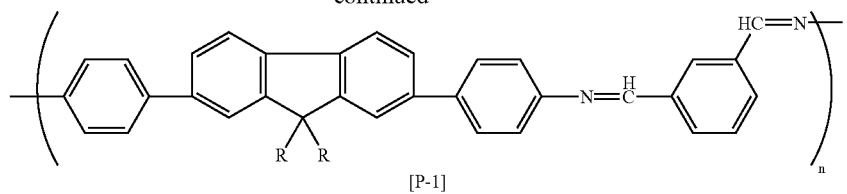
[P-1]
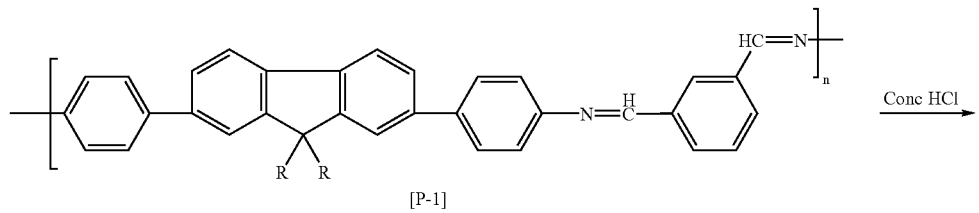
[P-1] → Conc HCl
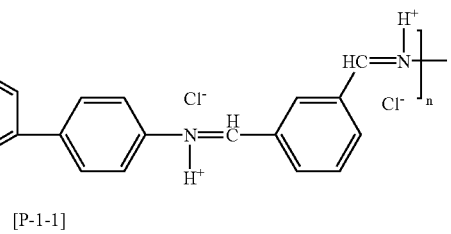
[P-1-1]
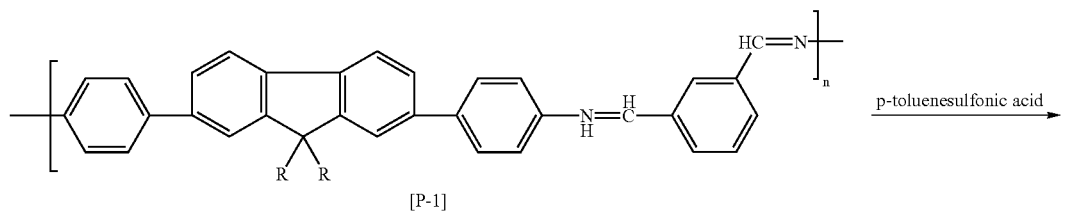
[P-1] → p-toluenesulfonic acid
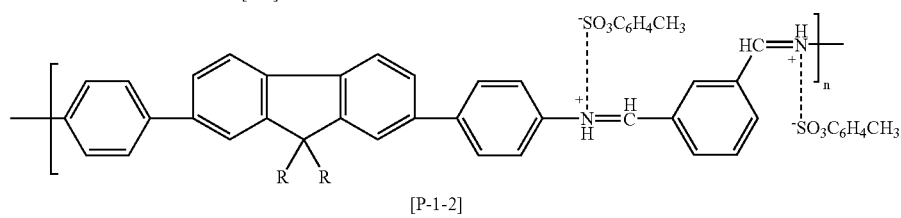
[P-1-2]
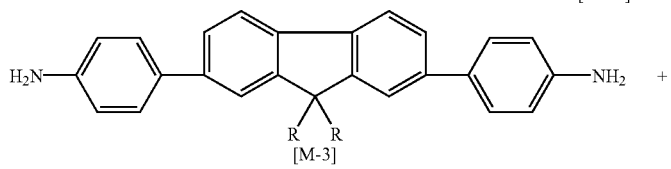
[M-3] +
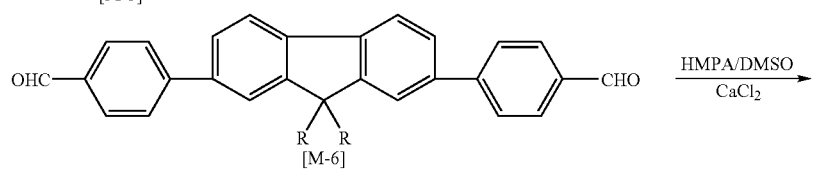
[M-6] → HMPA/DMSO / CaCl₂
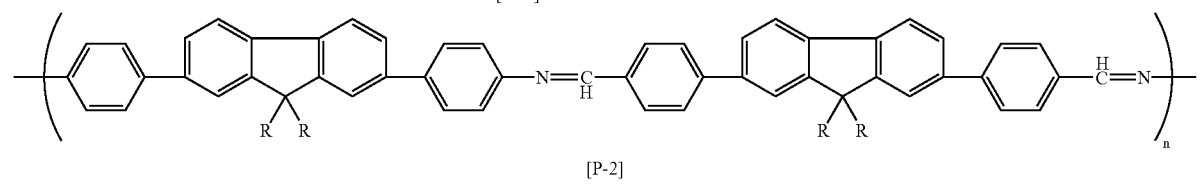
[P-2]

Reaction Scheme 7
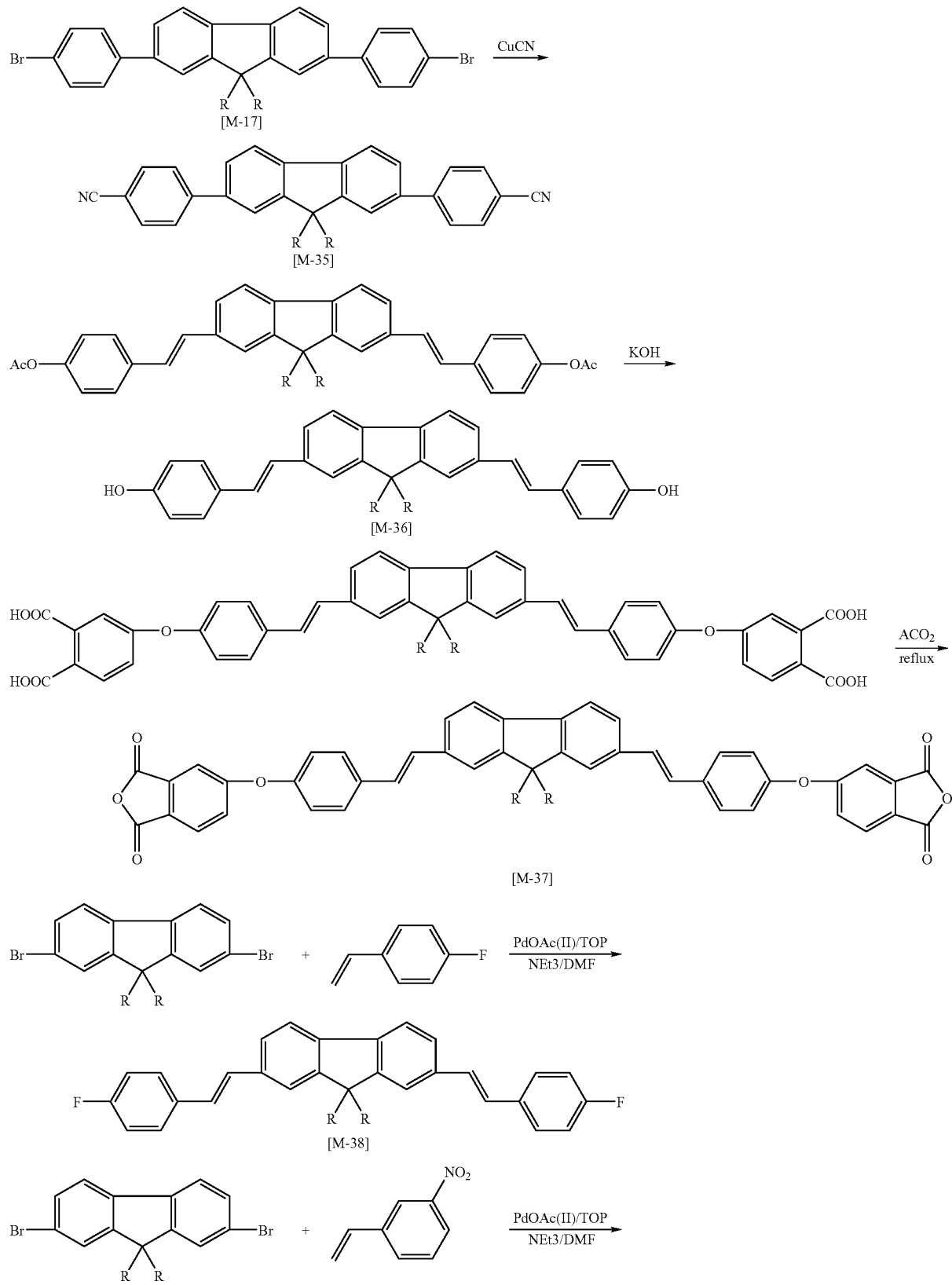

-continued
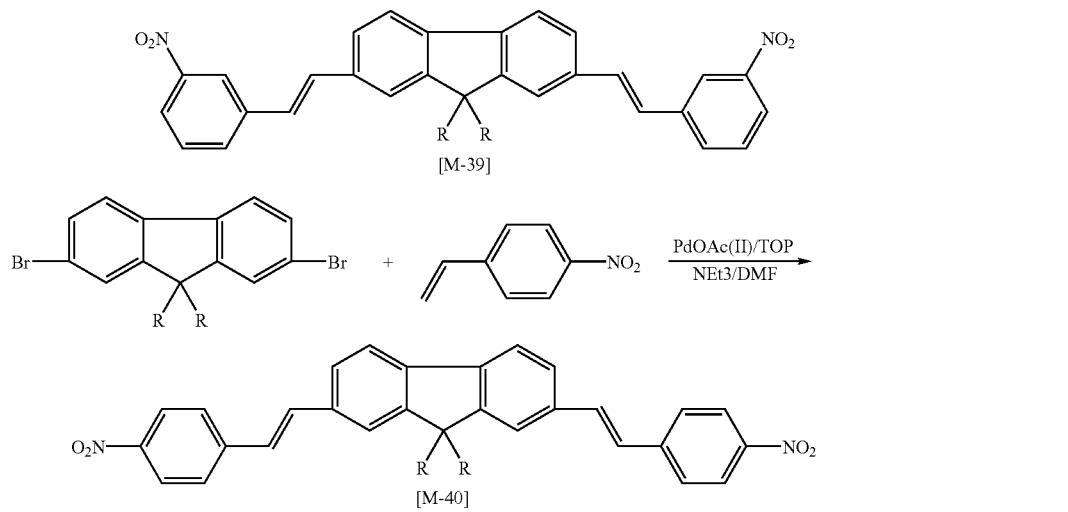
Reaction Scheme 8
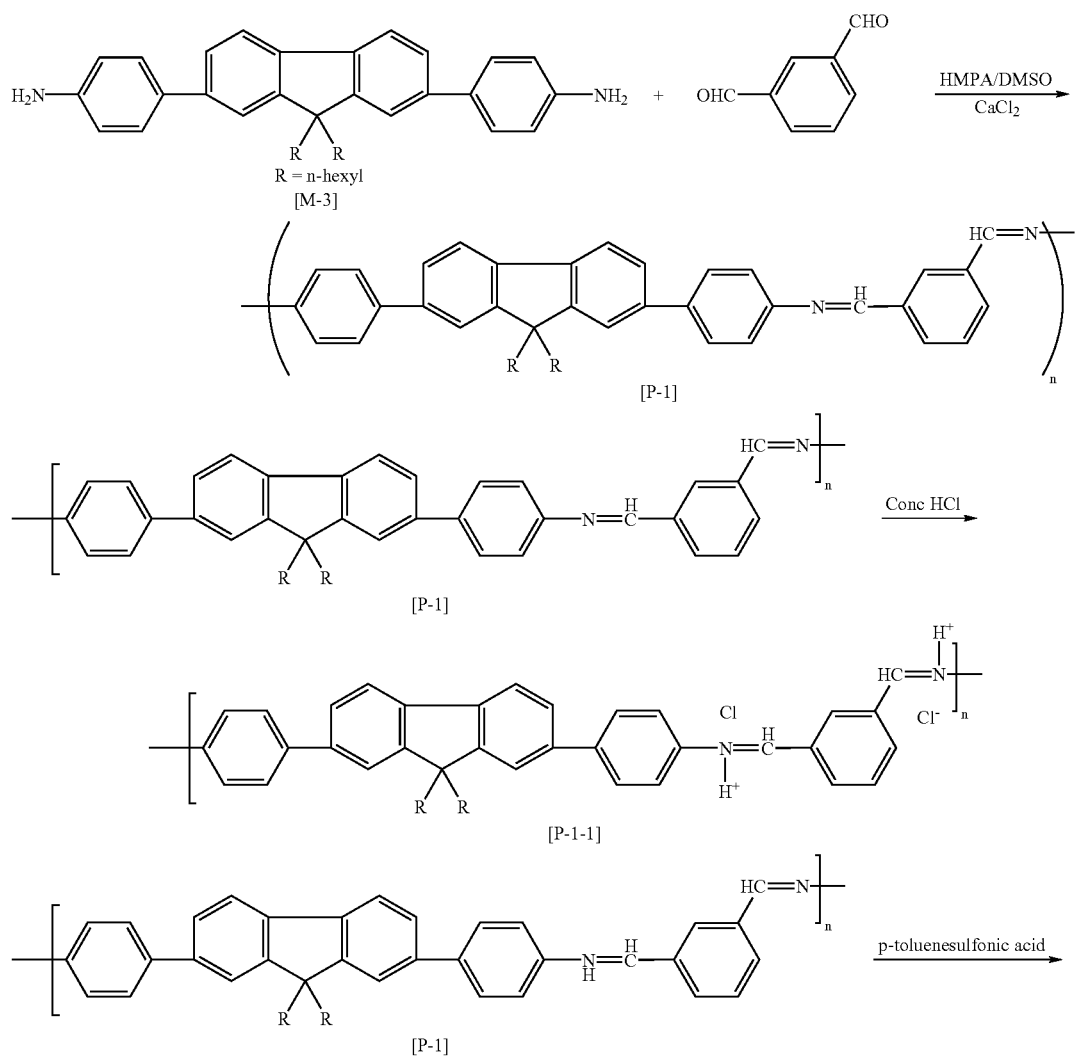

-continued
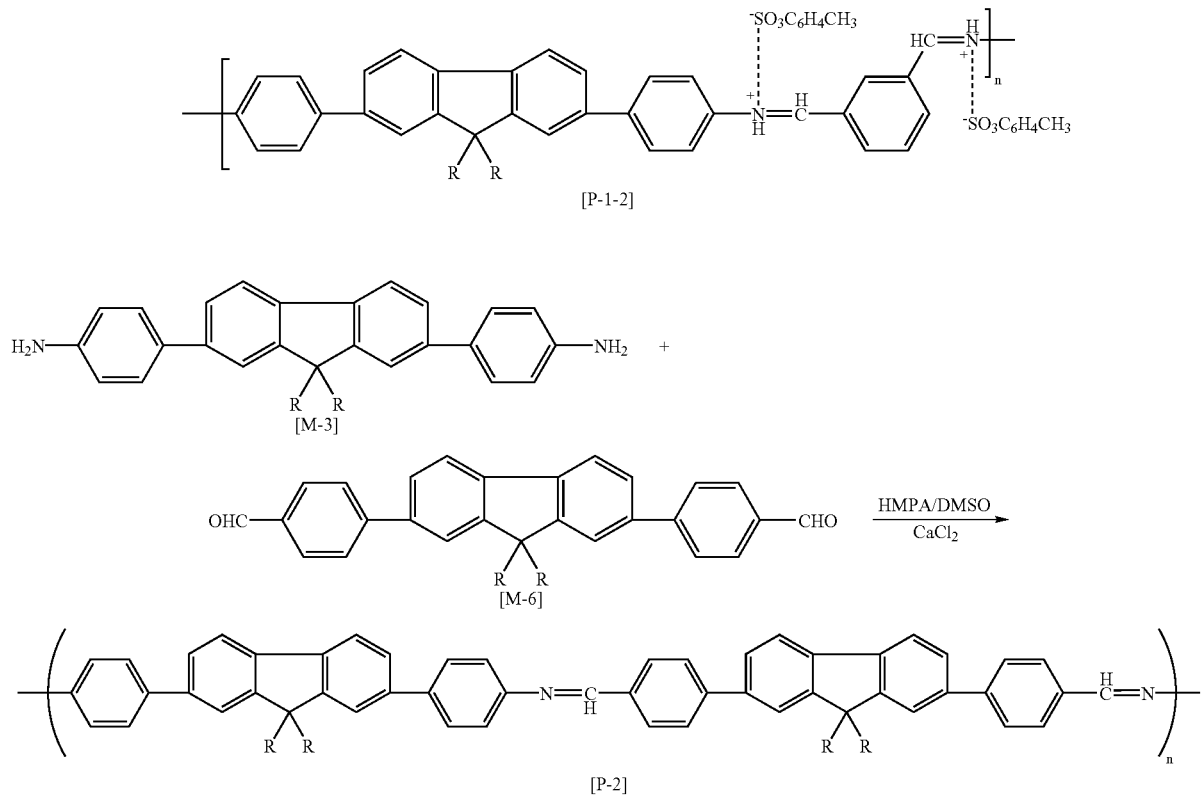
Reaction Scheme 9
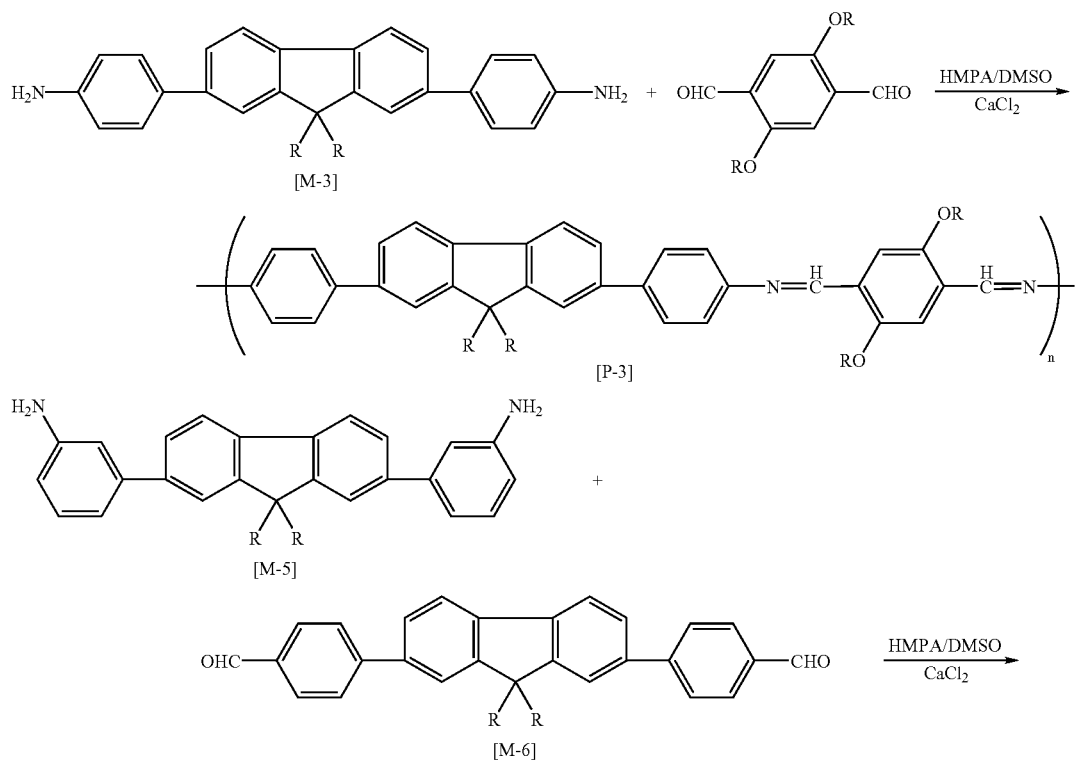

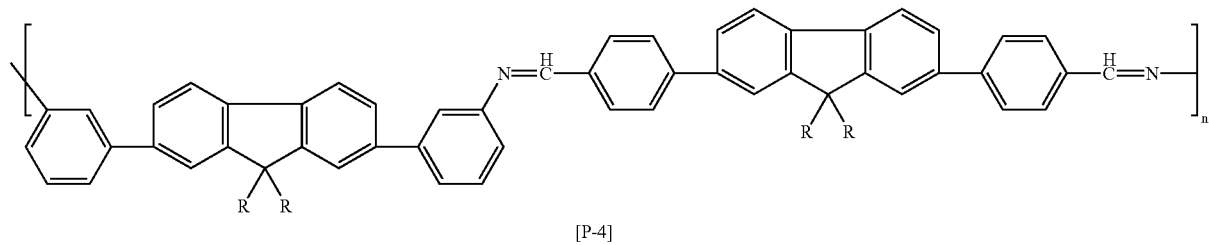
[P-4]
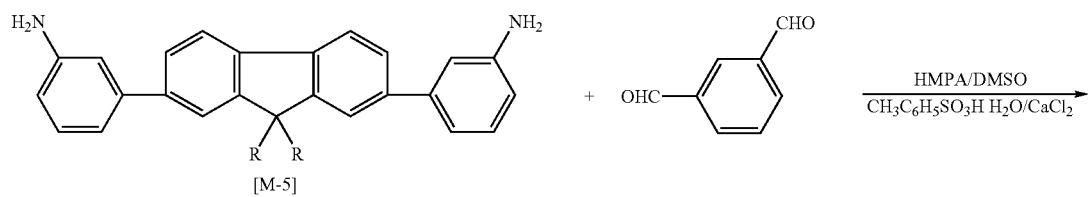
[M-5]
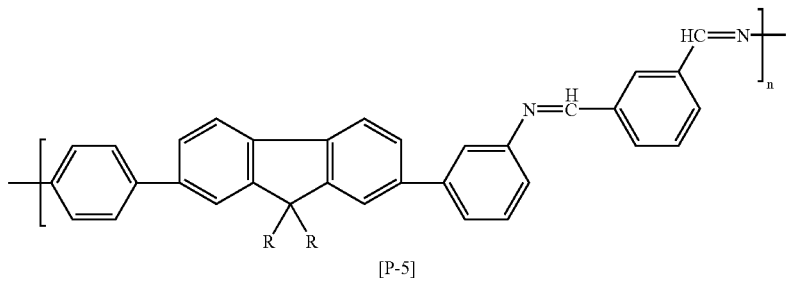
[P-5]
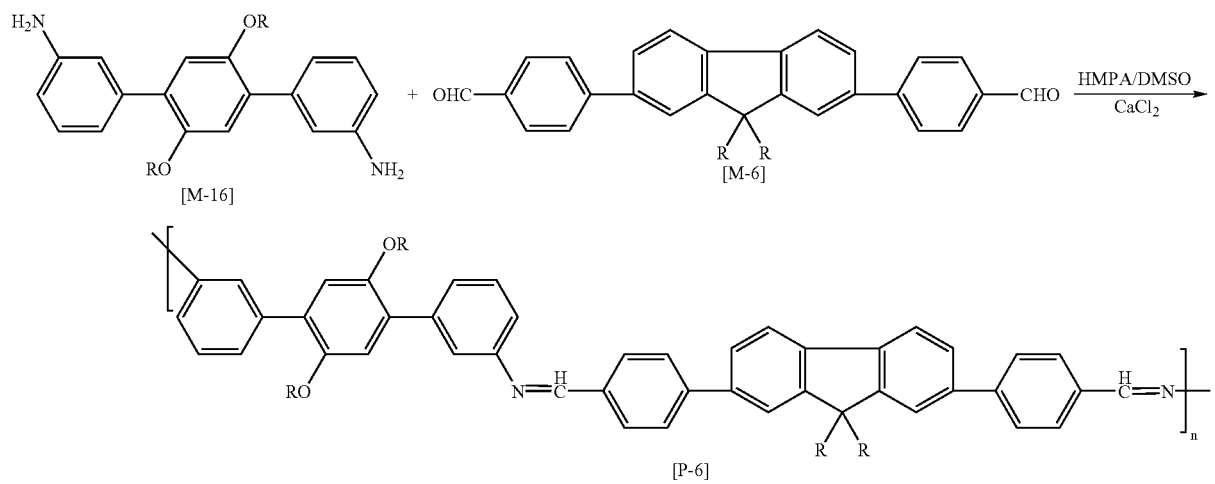
[M-16] + [M-6]
[P-6]
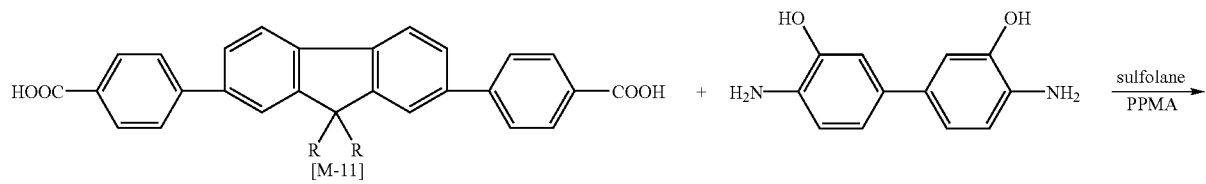
[M-11]

-continued
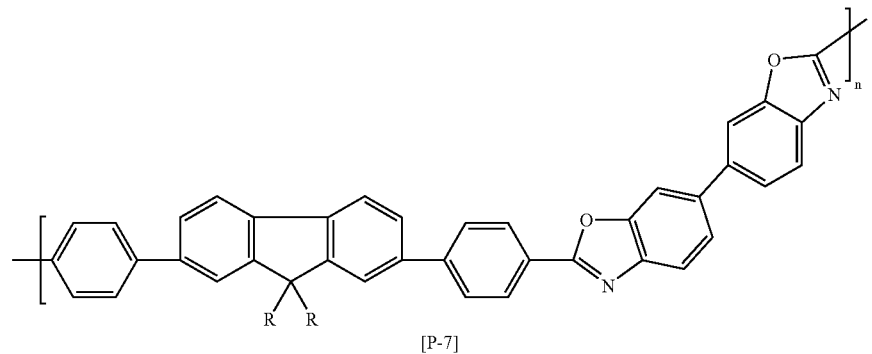
[P-7]
Reaction Scheme 10
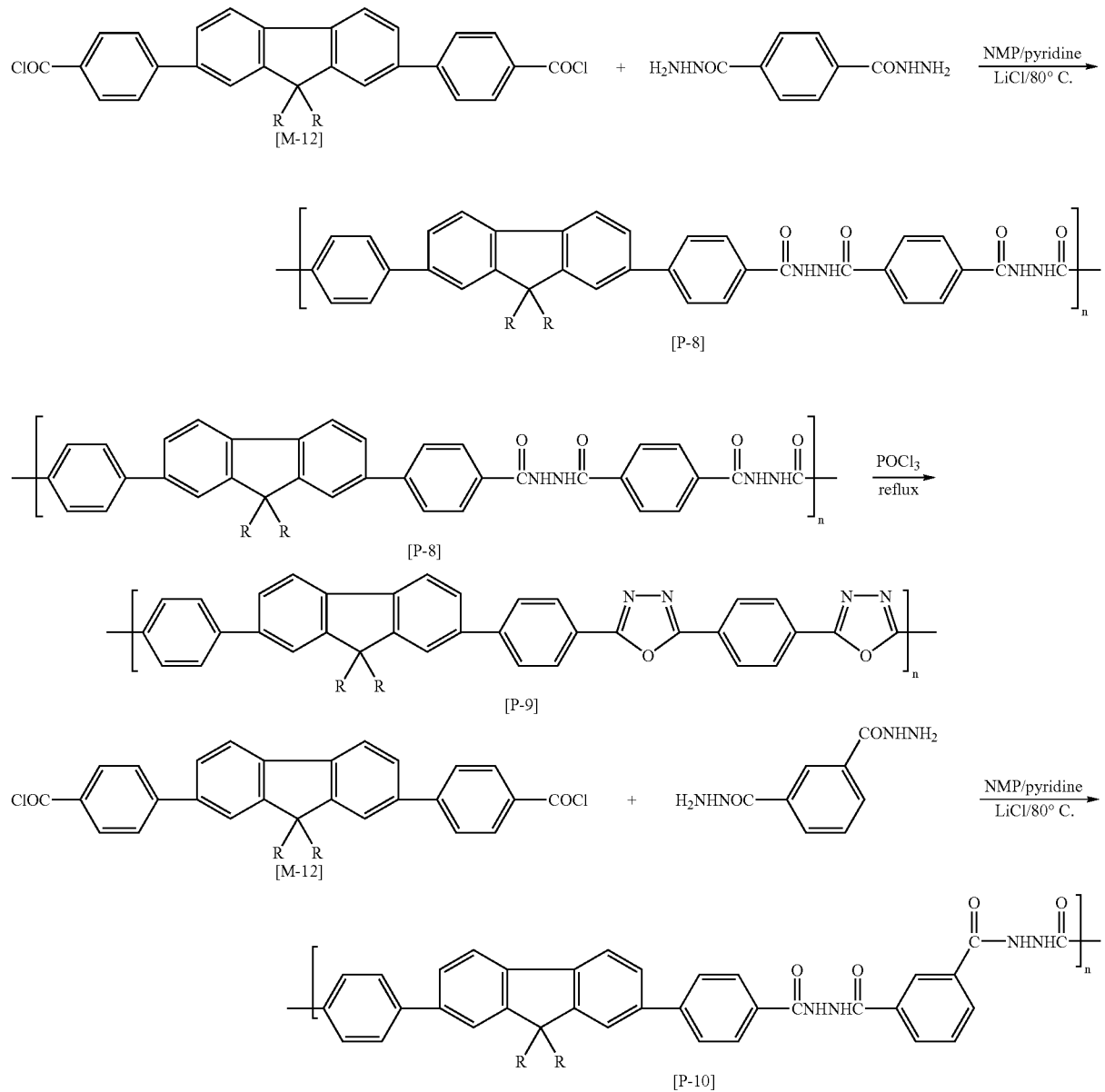

-continued
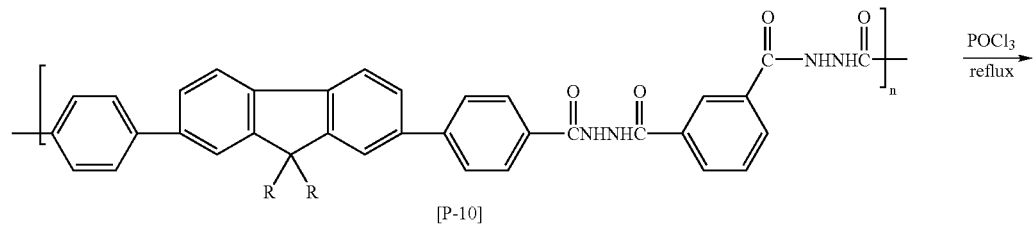
[P-10]
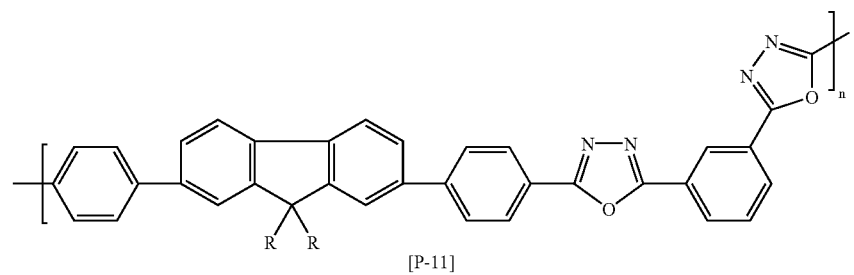
[P-11]
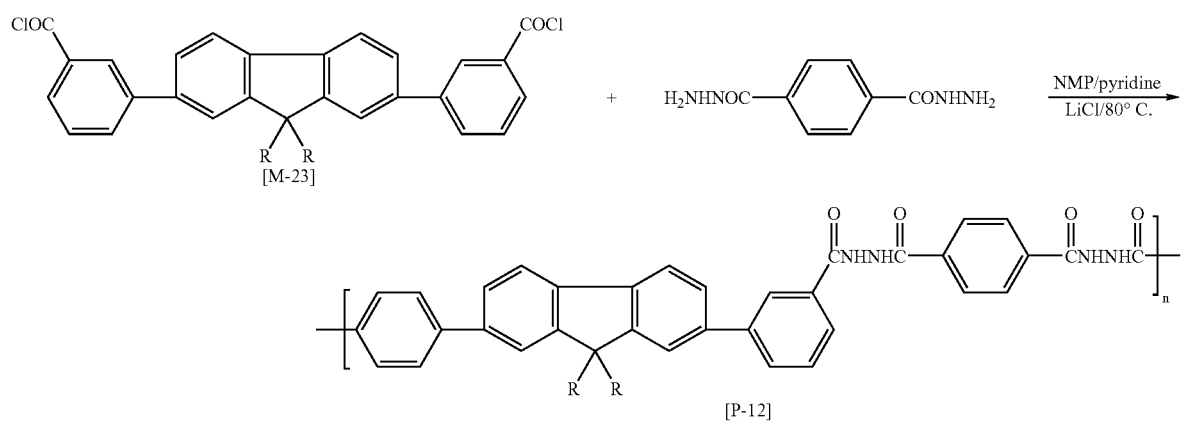
[M-23]
[P-12]
Reaction Scheme 11
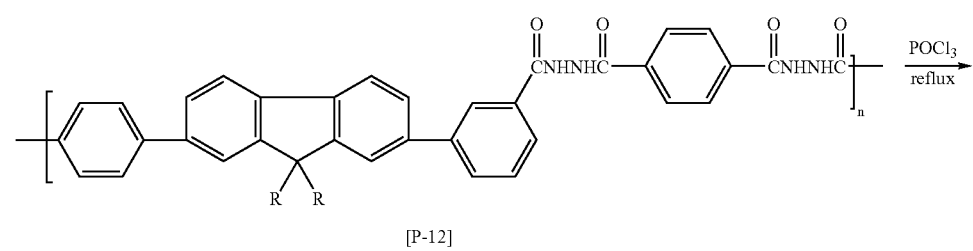
[P-12]
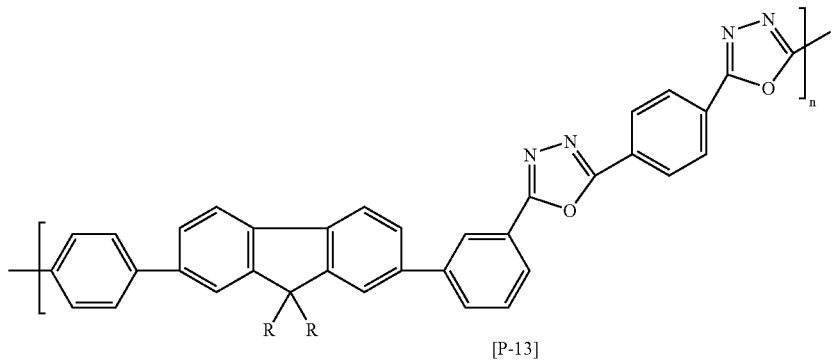
[P-13]

-continued
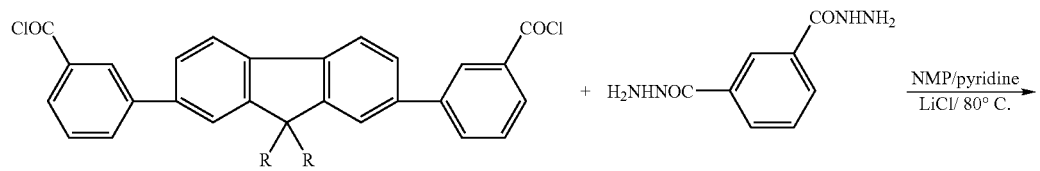
[M-23]
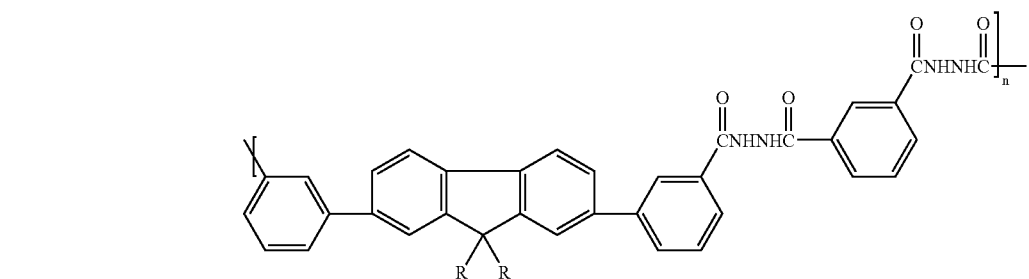
[P-14]
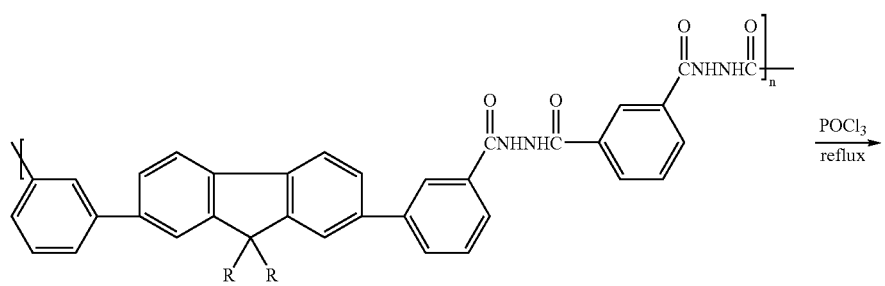
[P-14]
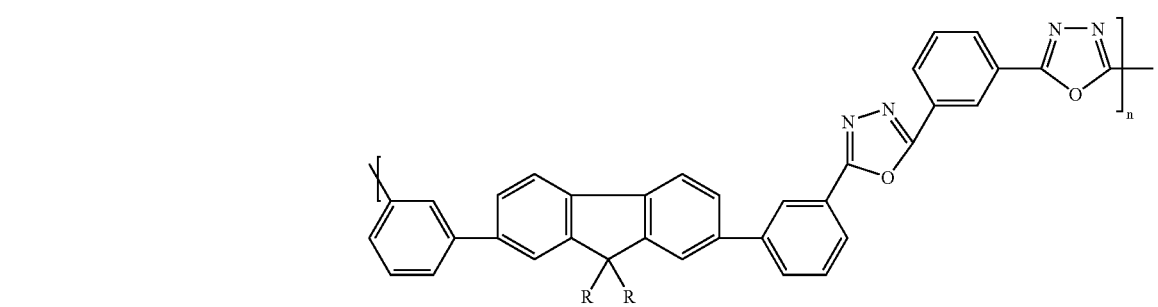
[P-15]
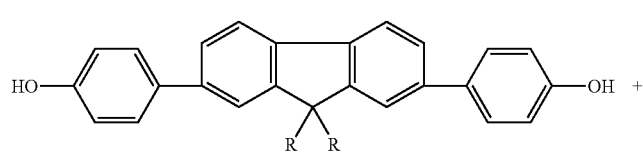
[M-29]
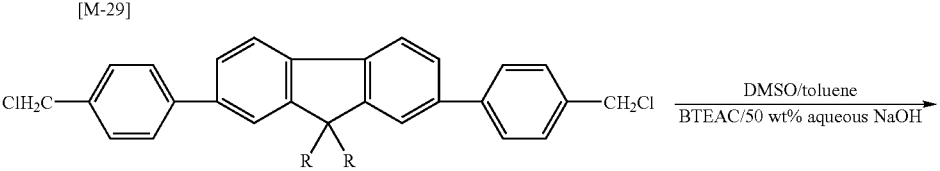
[M-25]

-continued
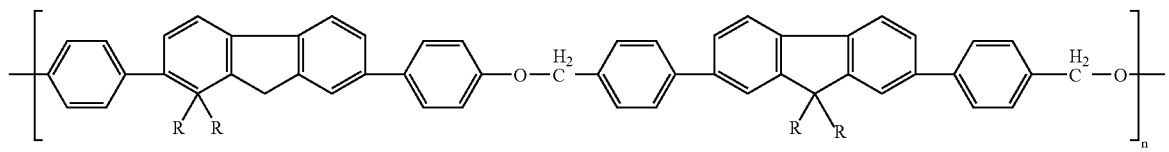
[P-16]
Reaction Scheme 12
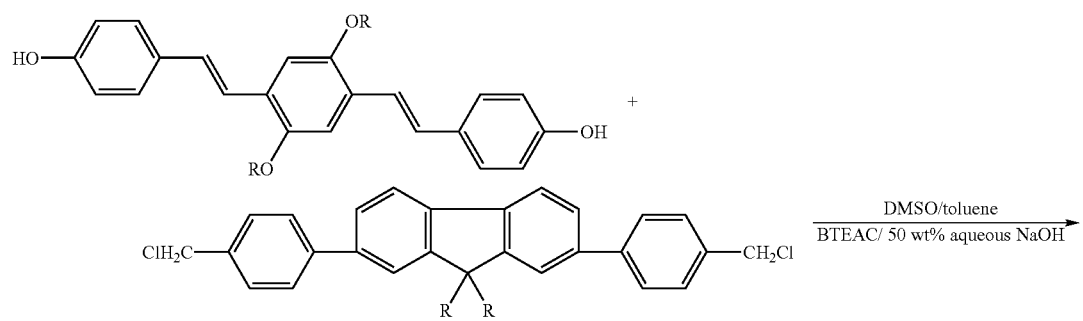
[M-25]
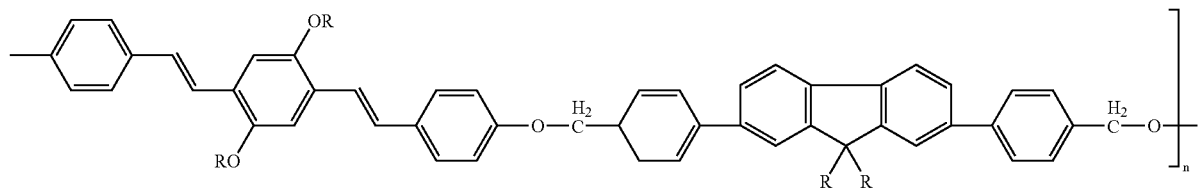
[P-17]
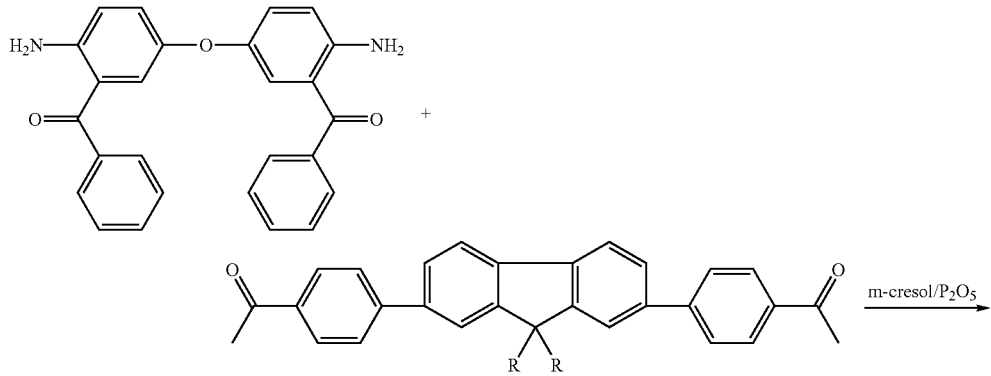
[M-34]
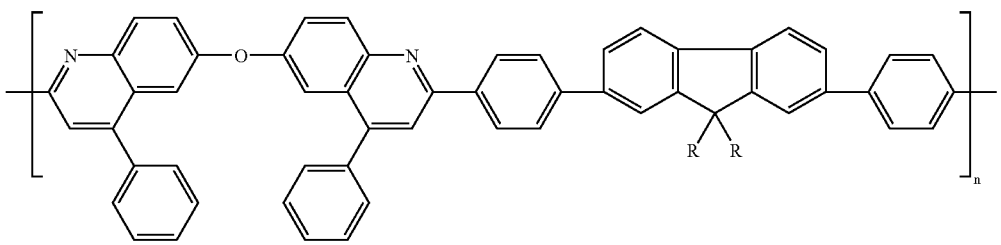
[P-18]

-continued
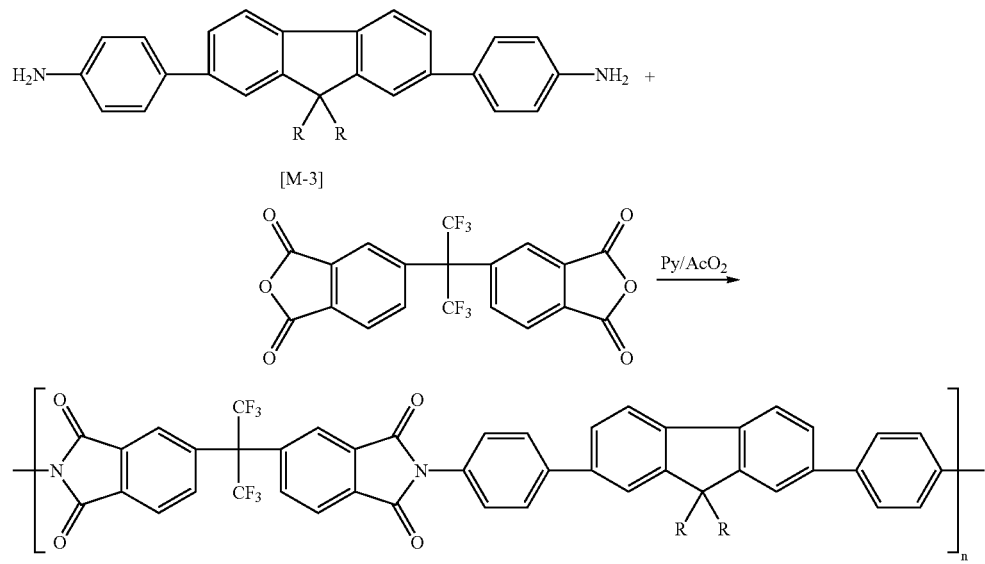
[M-3]
[P-19]
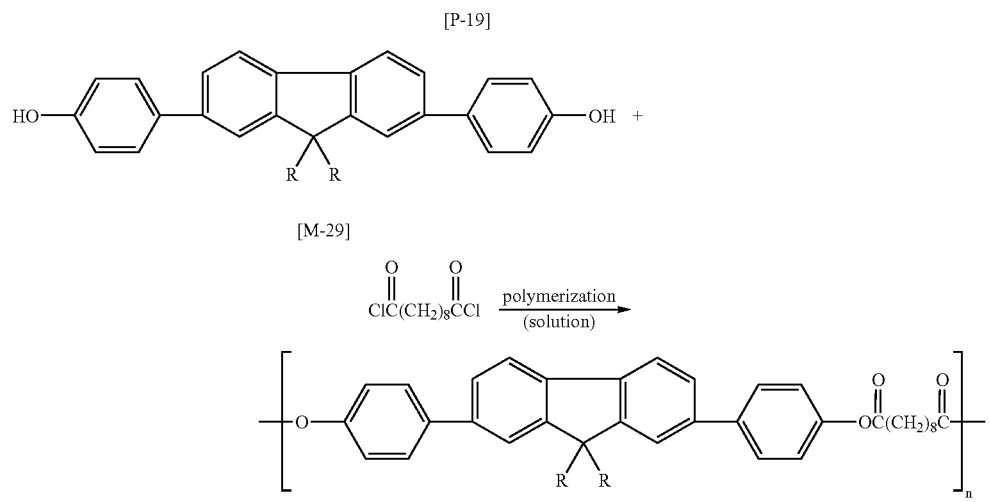
[M-29]
[p-20]
Reaction Scheme 13
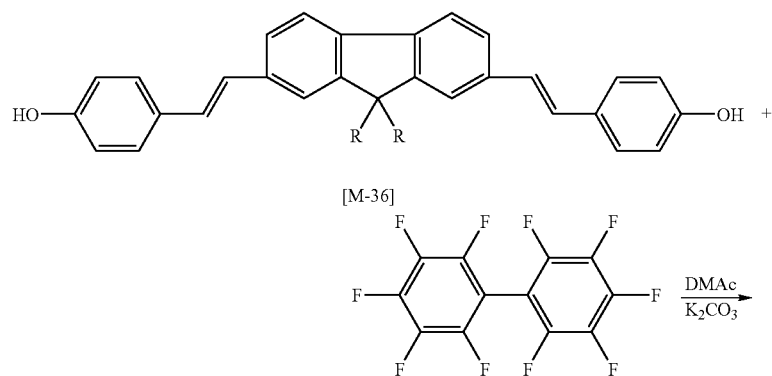
[M-36]

-continued
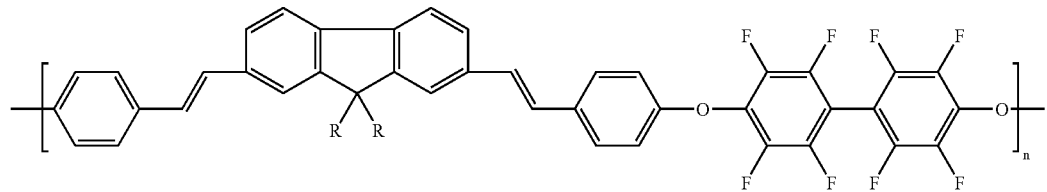
[P-21]
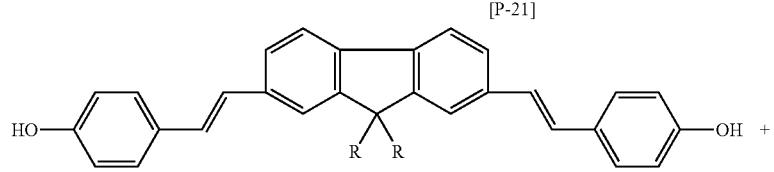
[M-36]
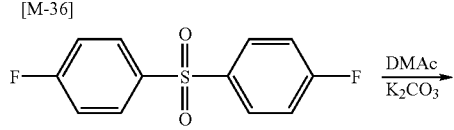
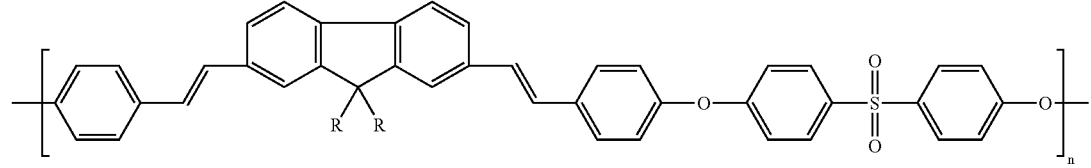
[P-22]
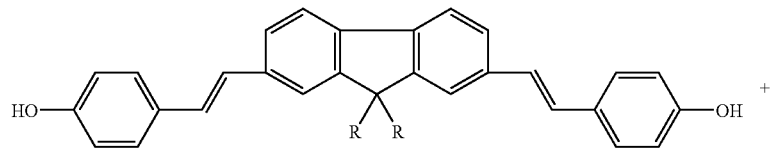
[M-36]
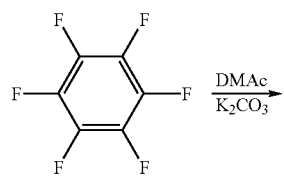
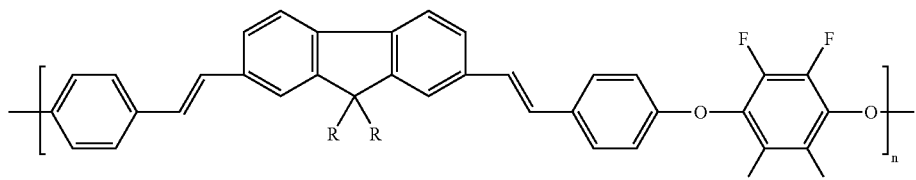
[P-23]
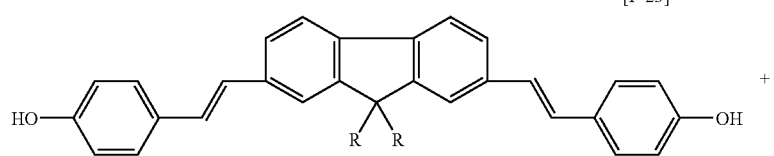
[M-36]
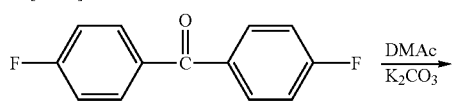

-continued
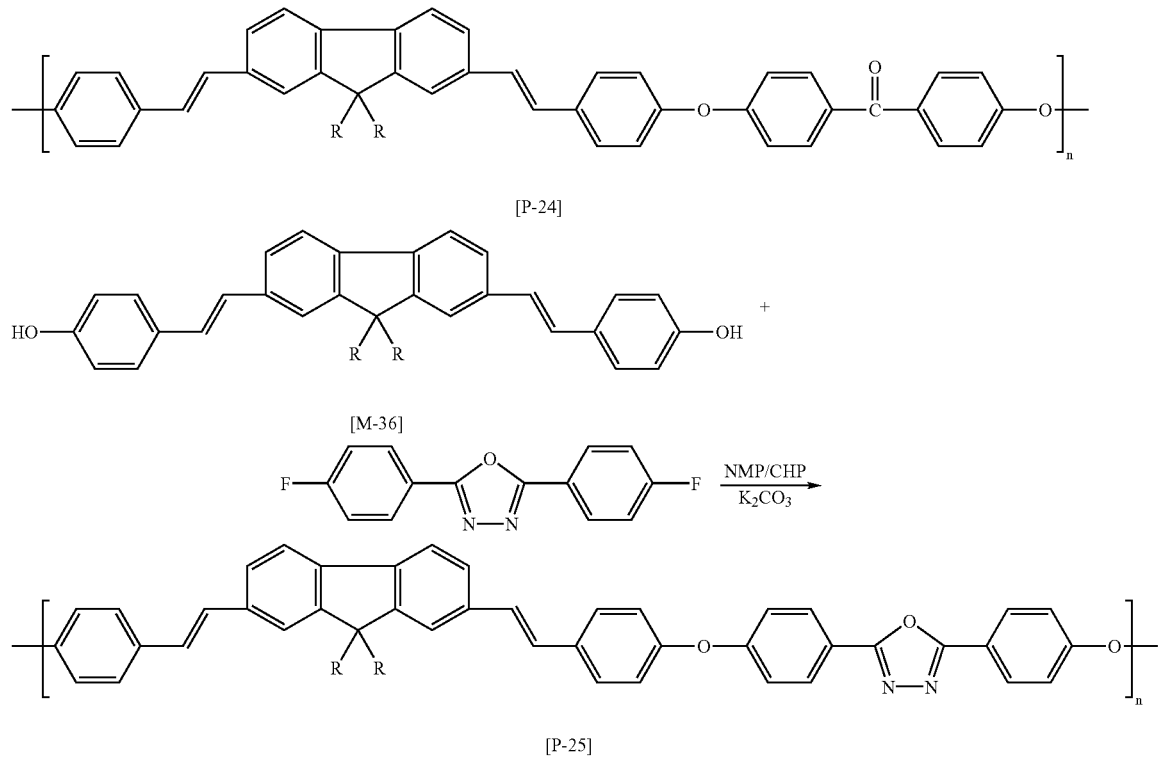
[P-24]
[M-36]
[P-25]
Reaction Scheme 14
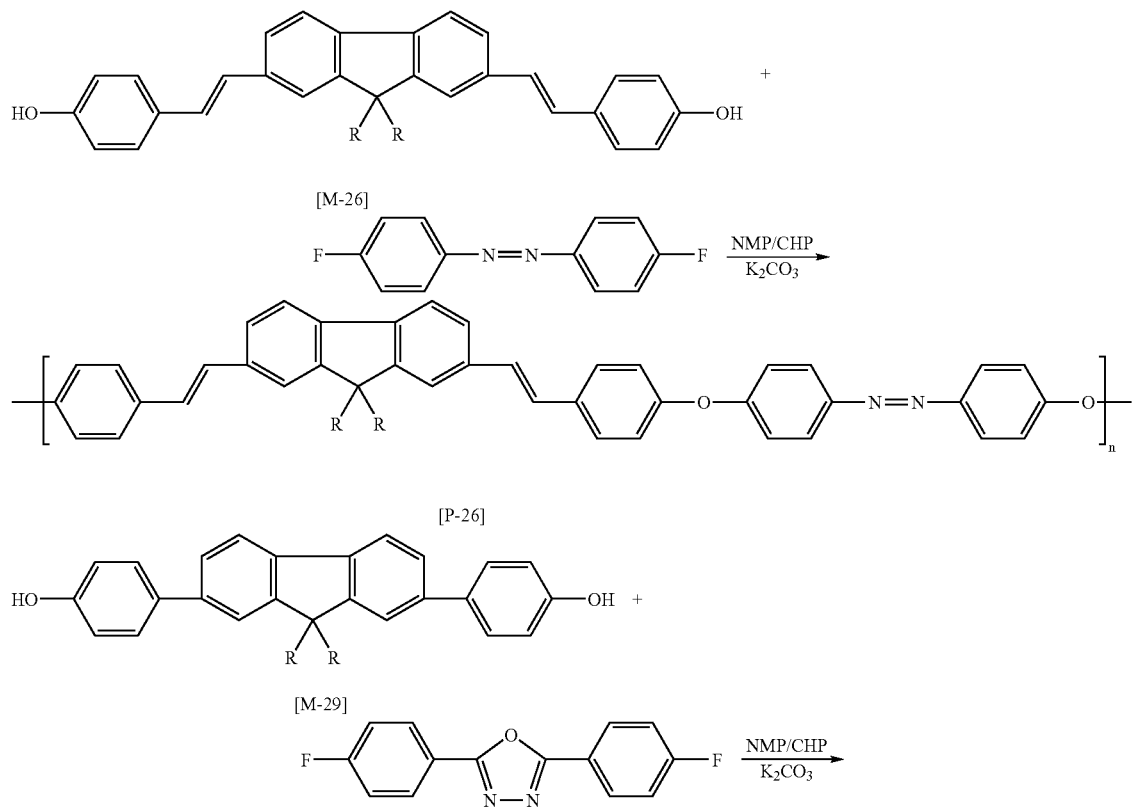
[M-26]
[P-26]
[M-29]

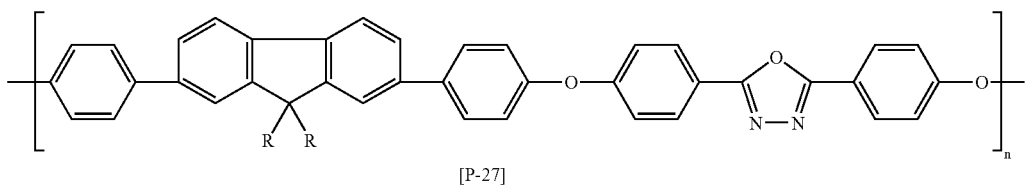
[P-27]
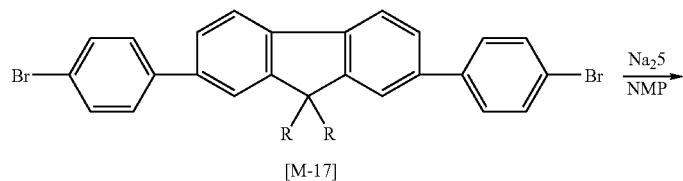
[M-17]
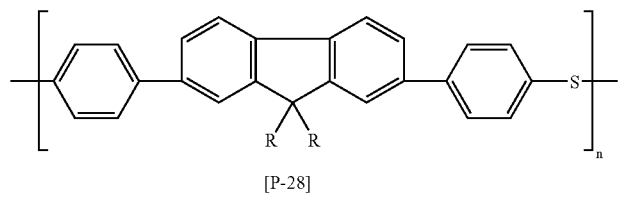
[P-28]
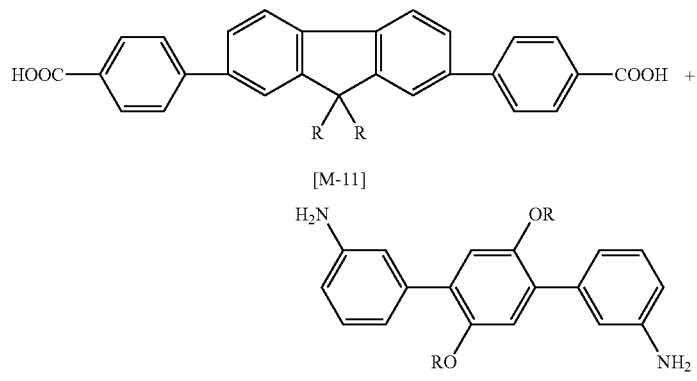
[M-11]
[M-16]
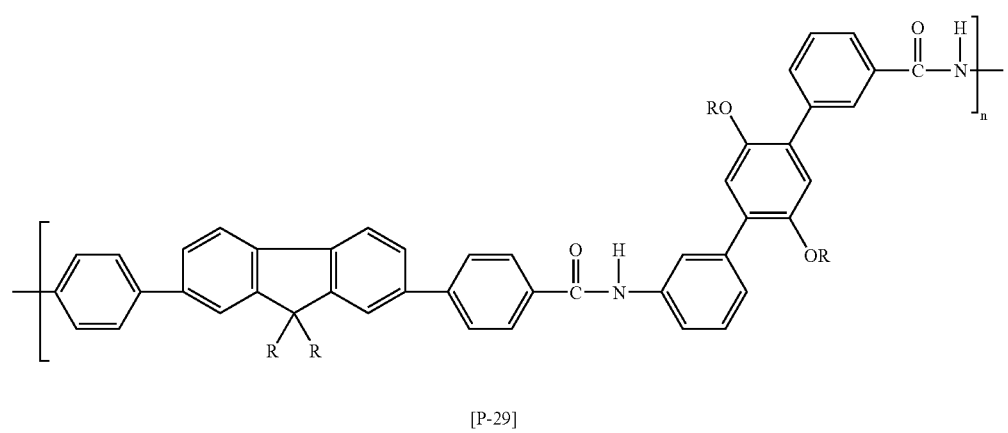
[P-29]
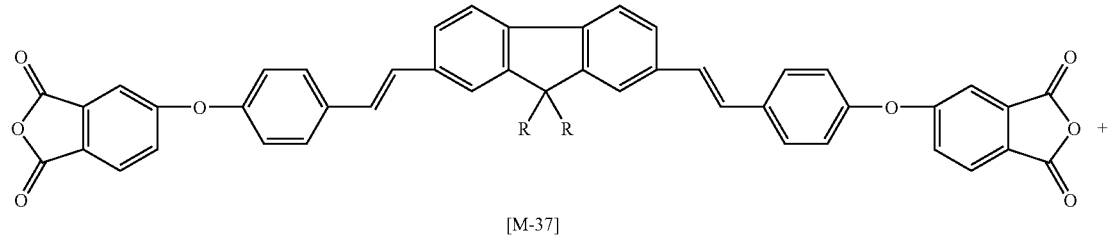
[M-37]

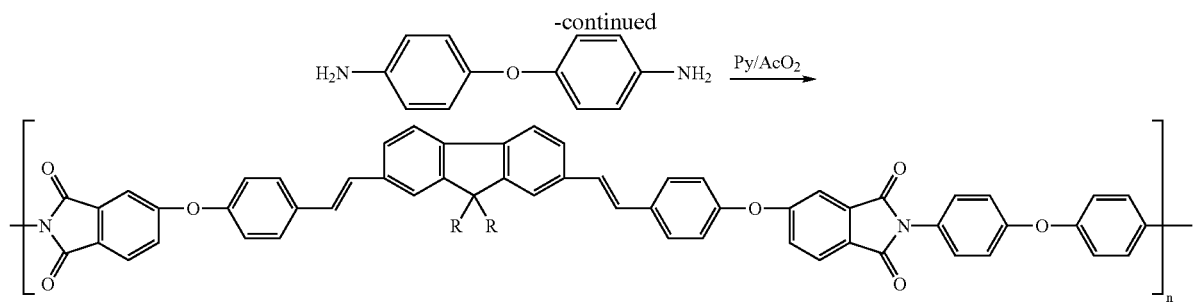

[P-30]

In addition to the above reaction procedures as described in Reaction Schemes 1 to 14, the fluorene compounds and/or the polymers thereof of the present invention can be prepared by using any known reactions if the final product has the same structure. That is, there is no need to limit a solvent, reaction temperature, concentration or catalyst used for preparing the fluorene compounds and/or polymers thereof of the present invention, and further it is regardless of a yield of the product.

The following Table 1 shows structures of the fluorene and other monomers M-1 to M-40 of the present invention, wherein the R is n-hexyl, and the light emitting properties thereof. The preparation and structures thereof will be described in more detail in Examples 1 to 40.

TABLE 1

| Monomers | Structure (R = n-Hexyl) | UV($\lambda_{max}$) (nm) | PL($\lambda_{max}$) (nm) | M.P.(° C.) |
|---|---|---|---|---|
| [M-1] | (HO)$_2$B—[fluorene, R = n-hexyl]—B(OH)$_2$ | 290/316 | 334 | 188-191 |
| [M-2] | O$_2$N—[phenyl]—[fluorene]—[phenyl]—NO$_2$ | 374 | — | 134-136 |
| [M-3] | H$_2$N—[phenyl]—[fluorene]—[phenyl]—NH$_2$ | 344 | 397 | 79-80 |
| [M-4] | O$_2$N—[phenyl]—[fluorene]—[phenyl]—NO$_2$ | 362 | — | 128-129 |
| [M-5] | H$_2$N—[phenyl]—[fluorene]—[phenyl]—NH$_2$ | 333 | 386 | 135-136 |

TABLE 1-continued

| Monomers | Structure (R = n-Hexyl) | UV($\lambda_{max}$) (nm) | PL($\lambda_{max}$) (nm) | M.P.(° C.) |
|---|---|---|---|---|
| [M-6] | OHC–C6H4–(fluorene-R,R)–C6H4–CHO | 354 | 428 | 120-121 |
| [M-7] | NCH2C–C6H4–(fluorene-R,R)–C6H4–CH2CN | 330 | 367/383 | 104-105 |
| [M-8] | CH2=CH–C6H4–(fluorene-R,R)–C6H4–CH=CH2 | 344 | 388/407 | 106-107 |
| [M-9] | ClH2C–C6H4(m)–(fluorene-R,R)–C6H4(m)–CH2Cl | 328 | 386/405 | 97-98 |
| [M-10] | H3C–C6H4–(fluorene-R,R)–C6H4–CH3 | 332 | 374 | 88-89 |
| [M-11] | HOOC–C6H4–(fluorene-R,R)–C6H4–COOH | 344 | 394 | 290-293 |
| [M-12] | ClOC–C6H4–(fluorene-R,R)–C6H4–COCl | 364 | 432 | 130-131 |
| [M-13] | C2H5O2C–C6H4(m)–(fluorene-R,R)–C6H4(m)–CO2C2H5 | 330 | 368/382 | 94-95 |
| [M-14] | C2H5O2C–C6H4–(fluorene-R,R)–C6H4–CO2C2H5 | 344 | 390/406 | 100-101 |

TABLE 1-continued

| Monomers | Structure (R = n-Hexyl) | UV($\lambda_{max}$) (nm) | PL($\lambda_{max}$) (nm) | M.P.(° C.) |
|---|---|---|---|---|
| [M-15] | O₂N–C₆H₄–C₆H₂(OR)₂–C₆H₄–NO₂ | 328 | — | 126-127 |
| [M-16] | H₂N–C₆H₄–C₆H₂(OR)₂–C₆H₄–NH₂ | 320 | 390 | 105-106 |
| [M-17] | Br–C₆H₄–(9,9-dihexylfluorene-2,7-diyl)–C₆H₄–Br | 332 | 368/386 | 12-123 |
| [M-18] | HC≡C–C₆H₄–(9,9-dihexylfluorene-2,7-diyl)–C₆H₄–C≡CH | 340 | 382 | 101-102 |
| [M-19] | OHC–C₆H₄–O–C₆H₄–(9,9-dihexylfluorene-2,7-diyl)–C₆H₄–O–C₆H₄–CHO | 334 | 376/482 | 86-88 |
| [M-20] | O₂N–C₆H₄–O–C₆H₄–(9,9-dihexylfluorene-2,7-diyl)–C₆H₄–O–C₆H₄–NO₂ | 334 | — | 102-103 |
| [M-21] | H₂N–C₆H₄–O–C₆H₄–(9,9-dihexylfluorene-2,7-diyl)–C₆H₄–O–C₆H₄–NH₂ | 335 | 375/393 | 57-58 |
| [M-22] | HOOC–C₆H₄–(9,9-dihexylfluorene-2,7-diyl)–C₆H₄–COOH | 330 | 404 | 227-229 |
| [M-23] | ClOC–C₆H₄–(9,9-dihexylfluorene-2,7-diyl)–C₆H₄–COCl | 326 | 445 | 113-114 |

TABLE 1-continued

| Monomers | Structure (R = n-Hexyl) | UV($\lambda_{max}$) (nm) | PL($\lambda_{max}$) (nm) | M.P.(° C.) |
|---|---|---|---|---|
| [M-24] | HOH₂C–(phenyl)–(fluorene with R,R)–(phenyl)–CH₂OH | 330 | 368/386 | 58-59 |
| [M-25] | ClH₂C–(phenyl)–(fluorene with R,R)–(phenyl)–CH₂Cl | 334 | 438 | 104-105 |
| [M-26] | H₂NHNOC–(phenyl)–(fluorene with R,R)–(phenyl)–CONHNH₂ | 343 | 406 | 134-136 |
| [M-27] | H₂NHNOC–(phenyl)–(fluorene with R,R)–(phenyl)–CONHNH₂ | 332 | 370/386 | 106-108 |
| [M-28] | H₃CO–(phenyl)–(fluorene with R,R)–(phenyl)–OCH₃ | 334 | 372/388 | 104-105 |
| [M-29] | HO–(phenyl)–(fluorene with R,R)–(phenyl)–OH | 340 | 397 | 142-143 |
| [M-30] | NCO–(phenyl)–(fluorene with R,R)–(phenyl)–OCN | 330 | 365/380 | 125-126 |
| [M-31] | (dicyanophenyl)–O–(phenyl)–(fluorene with R,R)–(phenyl)–O–(dicyanophenyl) | 332 | 364 | 183-184 |
| [M-32] | (dicarboxyphenyl)–O–(phenyl)–(fluorene with R,R)–(phenyl)–O–(dicarboxyphenyl) | 350 | 414 | 214-215 |
| [M-33] | (phthalic anhydride)–O–(phenyl)–(fluorene with R,R)–(phenyl)–O–(phthalic anhydride) | 332 | 374 | 187-188 |

TABLE 1-continued

| Monomers | Structure (R = n-Hexyl) | UV($\lambda_{max}$) (nm) | PL($\lambda_{max}$) (nm) | M.P.(° C.) |
|---|---|---|---|---|
| [M-34] | H₃COC–C₆H₄–(fluorene-R,R)–C₆H₄–COCH₃ | 350 | 414 | 130-131 |
| [M-35] | NC–C₆H₄–(fluorene-R,R)–C₆H₄–CN | 342 | 389/404 | 113-115 |
| [M-36] | HO–C₆H₄–CH=CH–(fluorene-R,R)–CH=CH–C₆H₄–OH | 378 | 415/438 | 96-97 |
| [M-37] | (phthalic anhydride)–O–C₆H₄–CH=CH–(fluorene-R,R)–CH=CH–C₆H₄–O–(phthalic anhydride) | 380 | 429 | 190-193 |
| [M-38] | F–C₆H₄–CH=CH–(fluorene-R,R)–CH=CH–C₆H₄–F | 372 | 407/430 | 110-111 |
| [M-39] | O₂N–C₆H₄(m)–CH=CH–(fluorene-R,R)–CH=CH–C₆H₄(m)–NO₂ | 376 | — | 189-192 |
| [M-40] | O₂N–C₆H₄–CH=CH–(fluorene-R,R)–CH=CH–C₆H₄–NO₂ | 374 | — | 164-166 |

The following Table 2 shows the structures of the fluorene-based polymers P-1 to P-30, wherein the R represents n-hexyl group, and the light emitting properties thereof. The preparation and structures thereof will be described in more detail in Examples 41 to 66.

TABLE 2

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-1] | | 370 | — | 19.9 | 2.54 |
| [P-1-1] | | 355 | 411 | — | — |
| [P-1-2] | | 348 | 418 | — | — |
| [P-2] | | 380 | — | 10.7 | 2.49 |
| [P-3] | | 333 | 375 | 9.6 | 1.82 |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-4] | | 360 | — | 19.2 | 2.44 |
| [P-5] | | 320 | — | 18.6 | 3.61 |
| [P-6] | | 362 | 425 | 4.8 | 1.88 |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-7] | | — | — | — | — |
| [P-8] | | 344 | 400 | 10.5 | 1.9 |
| [P-9] | | 366 | 454 | — | — |
| [P-10] | | 344 | 407 | 11.7 | 2.0 |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
| --- | --- | --- | --- | --- | --- |
| [P-11] | | 358 | 432 | — | — |
| [P-12] | | 334 | 386 | 12.3 | 2.1 |
| [P-13] | | 333 | 490 | — | — |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-14] | | 334 | 379 | 12.7 | 1.7 |
| [P-15] | | 326 | 398 | — | — |
| [P-16] | | 338 | 378/392 | 89.0 | 26 |
| [P-17] | | 334 | 448/475 | 76.2 | 2.4 |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-18] | | 374 | 431 | 40.3 | 3.38 |
| [P-19] | | 334 | 367 | $\eta_{inh}$ = 1.2 dl/g (30° C., 0.5 g/dl, NMP) | — |
| [P-20] | | 330 | 366/383 | 29.9 | 2.53 |
| [P-21] | | 378 | 415/438 | 258.8 | 3.57 |
| [P-22] | | 380 | 417/443 | 100.9 | 3.8 |

TABLE 2-continued

| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-23] | | 378 | 417/438 | 98.8 | 6.24 |
| [P-24] | | 380 | 418/442 | 28.2 | 2.66 |
| [P-25] | | 380 | 417/440 | 235.3 | 3.95 |
| [P-26] | | 384 | 418/443 | 13.7 | 2.28 |
| [P-27] | | 336 | 373/389 | 185.2 | 3.34 |

TABLE 2-continued
| Polymers | Structures (R = n-Hexyl) | UV($\lambda_{max}$) (nm) | PL($\lambda_{max}$) (nm) | $M_w \times 10^{-3}$ | P.D.I. |
|---|---|---|---|---|---|
| [P-28] | 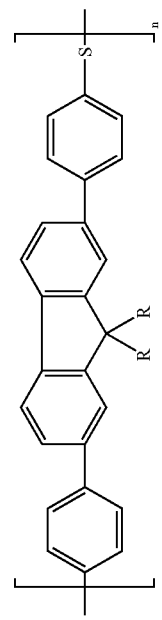 | 346 | 395 | 5.8 | 1.86 |
| [P-29] | 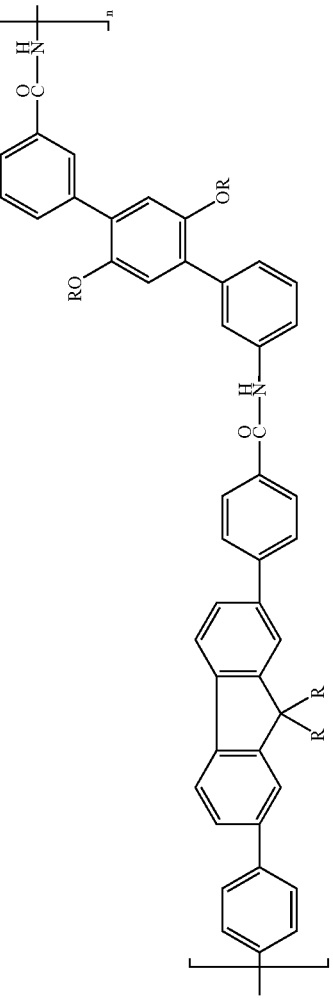 | 342 | 407 | — | $\eta_{inh}$ = 0.6 dl/g (30° C., 0.5 g/dl, DMAc) |
| [P-30] | 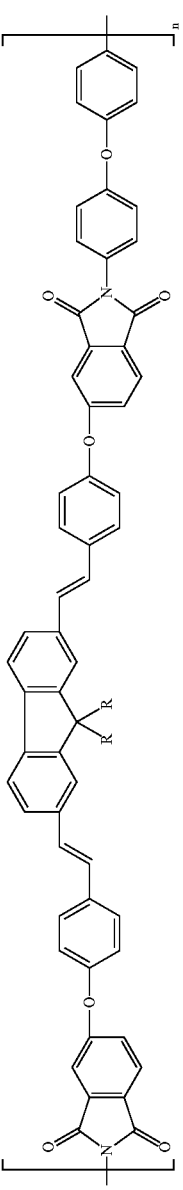 | 382 | — | — | $\eta_{inh}$ = 1.07 dl/g (30° C., 0.5 g/dl, NMP) |

The light emitting properties shown in the Tables 1 and 2 are measured using the method described in Example 67.

The organic and polymeric EL element and/or other optical elements according to the present invention can be fabricated using the fluorene compounds having various structures and functional groups and the polymers thereof as shown in the Table 1 and 2, as core materials for light emitting.

The fluorene compounds and/or polymers thereof can be made a film using known methods such as vacuum deposition, spin coating, role coating, bar coating, ink jet coating and the like, and can be directly used as EL materials.

The structure of the EL element can include a typical element constitution in which the material for the light emitting layer is inserted between an anode and a cathode, that is, an element constitution of anode/light emitting layer/cathode. Further, an element constitution in which uses together with a hole and electron transporting layer materials (Japanese Laid-open patent publications 2-135361, 3-152184 and 6-207170), that is, an element constitution of anode/hole transporting layer/light emitting layer/electron transporting layer/cathode can also be included. However, the constitution of the EL element of the present invention is not particularly limited.

The anode ordinarily comprises a transparent supporting substrate such as glass, transparent plastics, quartz, etc., coated with a metal or metal oxide such as ITO, gold, copper, tin oxide, zinc oxide, etc., or an organic semiconductor compound such as polypyrrole, polyaniline or polythiophene in the thickness of 10 nm to 1 μm thereon as electrode materials. The cathode is usually made of a metal such as sodium, magnesium, calcium, aluminum, indium, silver, gold, copper, or the like, or alloys thereof. In an embodiment of the present invention, the hole transporting layer can be formed by coating with polyvinylcarbazole, 2,5-bis(4'-diethylaminophenyl)-1,3,4-oxadiazole, N,N'-diphenyl-N,N'-(3-methylphenyl)-1,1'-biphenyl-4,4'-diamine (TPD) or the like, while the electron transporting layer can be formed by coating with known compounds such as tris(8-hydroxyquinolinato)aluminum, 2-(4'-t-butylphenyl)-5-(4"-biphenyl)-1,3,4-oxadiazole, 2,4,7-trinitro-9-fluorenone or the like, by employing known thin film formation methods such as vacuum deposition, spin-coating, casting, LB method, or the like.

The luminescent materials of the present invention can also be used by blending with the above hole or electron transporting layers, or other mutually different polymers of the present invention, and known luminescent polymers such as soluble PPV or PTh derivatives. For instance, polyvinylcarbazole, poly(1,4-hexyloxy-2,5-phenylenevinylene), poly(3-hexylthiophene), or the like and the fluorene-based polymers of the present invention can be dissolved in an organic solvent such as chloroform, and then coated them by spin coating, casting method, or the like. Although no particular restrictions are required, the concentration of the fluorene-based luminescent polymers of the present invention is in the range of 0.001 to 99%, preferably 0.1 to 50% of the polyvinylcarbazole, and the thickness of the film is from 5 nm to 5 μm, preferably from 50 nm to 1 μm.

Also, polymers that are soluble in any typical organic solvent and can be formed into a film may be used by blending with the luminescent material of the present invention in the same concentration and thickness as described above. Such polymers can include thermoplastics such as polymethylmethacrylate, polyarcylate, polystyrene, polycarbonate, polyvinyichloride, polyethylene, polypropylene, polyacrylonitrile, polyvinylpyrrolidone, polyvinylalcohol, polyvinylacetate, polyvinylbutyral, polyvinylamine, polycaprolacton, polyethylentherephthalate, polybutylentherephthalate, polyurethan, ABS, polysulfone, polyvinylfluoride, or the like, or resins for general use such as acetal, polyamides, polyimides, polyesters, alkyd, urea, furan, nylons, melamine, phenol, silicone, epoxy, or the like.

EXAMPLE

The present invention will now be described in more detail by examples which are not limited.

Synthesis of Monomers:

Example 1

Synthesis of 9,9'-di-n-hexylfluorene-2,7-diboranic acid (M-1)

Under an argon atmosphere, 2,7-dibromo-9,9'-dihexylefluorene 60.0 g (0.12 mol) and magnesium 11.9 g (0.49 mol) were introduced into a 1 L three-necked flask equipped with a stirrer, a thermometer and a reflux condenser and dissolved in 40 ml of anhydrous tetrahydrofuran (THF). After adding small amount of iodine to the above mixture, it was refluxed for 6 hours at 70° C., to obtain Grynard Reagent of pure brown color. Into a separate 2 L three-necked flask equipped with a mechanical stirrer, trimethyl borate [B(OCH$_3$)$_3$] 38.0 g (0.36 mol) was introduced, cooled with dry-ice and dissolved in 300 ml of anhydrous THF. To this solution, the Grynard Reagent obtained above was added, and the resulting solution was stirred for two hours at −78° C. and two days at room temperature. 500 ml of 2M hydrochloric acid was added gradually to the reaction mixture, and then the mixture was stirred for three hours, whereby pure yellow solution was obtained. The solution was extracted three times with diethyl ether, and combined extract was dried with anhydrous magnesium sulfate, filtered to remove drying agent, and then the solvent was removed, thereby to give pale brown solid. By recrystallizing in a mixture of acetone/hexane (20/80), white solid was obtained. The solid was filtered and dried in a vacuum oven at 40° C., to give 30 g of the desired product (yield 58.8%).

Mp: 188-189° C.; $^1$H NMR (DMSO-d$_6$): δ 0.42 (br, 6H, CH$_3$), 0.61-0.91 (t, 16H, CH$_2$), 1.9 (br, s, 4H, CCH$_2$), 7.73-7.81 (d, 6H, aromatic), 8.04 (s, 4H, OH).

Example 2

Synthesis of 2,7-bis (4-nitrophenyl)-9,9'-di-n-hexylfluorene (M-2)

Under an argon atmosphere, 9,9'-di-n-hexylfluorene-2,7-diboranic acid 5.0 g (11.8 mmol), 4-bromonitrobenzene 5.26 g (26.0 mmol) and tetrakistriphenylphosphine palladium [(PPh$_3$)$_4$]Pd(0) 0.3 g (0.26 mmol) were introduced into a 500 ml three-necked flask equipped with a stirrer, a thermometer and a reflux condenser and dissolved in 140 ml of toluene. In addition, 65 ml of 2M sodium carbonate solution was added to the mixture, and then the reaction mixture was refluxed for 48 hours. After the reaction was completed, the reaction mixture was cooled to be room temperature, and then the mixture was extracted three time with toluene. Combined extract was washed with water and dried with anhydrous magnesium sulfate. When the solvent was removed, visco-elastic liquid was obtained. The liquid was purified by performing chromatography on silica gel column using a mixture of hexane/methylenechloride (1/1) as an eluent. By performing recrystallization in a mixture of ethyl acetate/hexane, fine yellow crystal was obtained. By drying the obtained solid in a vacuum oven at 40° C., 5 g of the desired product (yield: 73.2%) was obtained.

Mp: 134-136° C.; $^1$H NMR (CDCl$_3$): δ 0.72-1.12 (m, 22H, CH$_2$ and CH$_3$), 2.04-2.12 (m, 4H, CCH$_2$), 7.62-7.81 (m, 14H, aromatic).

Example 3

Synthesis of 2,7-bis (4-aminophenyl)-9,9'-di-n-hexylfluorene (M-3)

2,7-bis (4-nitrophenyl)-9,9'-di-n-hexylfluorene 4.0 g (6.9 mmol) and 10 wt. % palladium activated carbon (Pd/C) 1 g were introduced into a 500 ml two-necked flask equipped with a stirrer and dissolved in 50 ml of ethyl acetate, and then the mixture was reacted at room temperature for 24 hours while filling hydrogen gas. When the reaction was completed, anhydrous magnesium sulfate was added to the reaction mixture to dry, the reaction mixture was filtered to remove the drying agent, and the solvent was then removed, to give viscous liquid. The liquid was purified by performing chromatography on silica gel column using methylenechloride as an eluent. By performing recrystallization in methanol, white fine crystal was obtained. The obtained solid was dried in a vacuum oven at 40° C., to give 2.2 g of the desired product (yield: 65.0%).

Mp: 79-81° C.; $^1$H NMR (CDCl$_3$): δ 0.72-1.15 (m, 22H, CH$_2$ and CH$_3$), 1.96-2.04 (m, 4H, CCH$_2$), 3.67 (br, s, 4H, NH$_2$), 6.76-7.72 (m, 14H, aromatic).

Example 4

Synthesis of 2,7-bis(3-nitrophenyl)-9,9'-di-n-hexylfluorene (M-4)

Under an argon atmosphere, 2,7-dibromo-9,9'-di-n-hexylfluorene 40.0 g (81.3 mmol), 3-nitrobenzeneboron acid [(O$_2$NC$_6$H$_4$B(OH)$_2$)] 29.8 g (0.178 mol) and tetrakistriphenylphosphine palladium 0.93 g (0.81 mmol) were introduced into a 1 L three-necked flask equipped with a thermometer, a mechanical stirrer and a reflux condenser and dissolved in 300 ml of toluene. In addition, 150 ml of 2M sodium carbonate was added to the mixture, and then the reaction mixture was refluxed for 48 hours. After the reaction was completed, the reaction mixture was cooled to be room temperature, and the reaction mixture was extracted with toluene three times. Combined extract was washed with water and dried with anhydrous magnesium sulfate. After filtering to remove the drying agent, solvent was removed, to give viscous liquid. The liquid was purified by performing chromatography on silica gel column using a mixture of ethyl acetate/hexane (1/3) as an eluent and then recrystallized in a mixture of ethyl acetate/hexane, to give fine yellow crystal. By drying the obtained solid in a vacuum oven at 40° C., 25 g of the desired product (yield: 53.3%) was obtained.

Mp: 135-136° C.; $^1$H NMR (CDCl$_3$): δ 0.72-1.13 (m, 22H, CH$_2$ and CH$_3$), 2.06-2.14 (m, 4H, CCH$_2$), 7.62-8.56 (m, 14H, aromatic).

Example 5

Synthesis of 2,7-bis(3-aminophenyl)-9,9'-di-n-hexylfluorene (M-5)

2,7-bis(3-nitrophenyl)-9,9'-di-n-hexylfluorene 9.0 g (15.6 mmol) and 10 wt % palladium activated carbon (Pd/C) 1.5 g were introduced into a 500 ml two necked flask equipped with a stirrer and dissolved in 100 ml of ethyl acetate, and then the reaction mixture was reacted at room temperature for 24 hours while filling hydrogen gas. When the reaction was completed, anhydrous magnesium sulfate was added to dry and removed by filtering, and then solvent was removed to give viscous liquid. The liquid was purified by performing chromatography on silica gel column using a mixture of ethyl acetate/hexane (1/1). By performing recrystallization in a mixture of diethyl ether/methanol, white crystal was obtained. The white crystal was dried in a vacuum oven at 40° C. to give 6.5 g of the desired product (yield: 80%).

Mp: 120-121° C.; $^1$H NMR (CDCl$_3$): δ 0.76-1.16 (m, 22H, CH$_2$ and CH$_3$), 2.02-2.10 (m, 4H, CCH$_2$), 3.77 (br, s, 4H, NH$_2$), 6.72-7.79 (m, 14H, aromatic).

Example 6

Synthesis of 2,7-bis(4-aldehydephenyl)-9,9'-di-n-hexylfluorene (M-6)

Under an argon atmosphere, 9,9'-di-n-hexylfluorene-2,7-diboranic acid 5.0 g (11.8 mmol), 4-bromobenzaldehyde (BrC$_6$H$_4$CHO) 4.8 g (26.0 mmol) and tetrakistriphenylphosphine palladium 0.3 g (0.26 mmol) were introduced into a 500 ml three-necked flask equipped with a thermometer, a stirrer and a reflux condenser, and then the mixture was refluxed for 48 hours. After the reaction was completed, the reaction mixture was cooled to be room temperature and extracted with toluene three times. Combined extract was washed with water several times and then dried with anhydrous magnesium sulfate. Solvent was removed to give viscous liquid. The liquid was purified by performing chromatography on silica gel column using methylenechloride as an eluent. By performing recrystallization in a mixture of ethyl acetate/hexane, yellow crystal was obtained. The crystal was dried in a vacuum oven at 40° C. to give 5.0 g of desired product (yield: 77.8%).

Mp: 128-129° C.; $^1$H NMR (CDCl$_3$): δ 0.71-1.12 (m, 22H, CH$_2$ and CH$_3$), 2.03-2.11 (m, 4H, CCH$_2$), 7.62-8.02 (m, 14H, aromatic), 10.08 (s, 2H, CHO).

Example 7

Synthesis of 2,7-bis(4-acetoniterylphenyl)-9,9'-di-n-hexylfluorene (M-7)

Under an argon atmosphere, 9,9'-di-n-hexylfluorene-2, 7-diboranic acid 9.0 g (16.58 mmol), 4-bromophenylacetonitryl (BrC$_6$H$_4$CH$_2$CN) 7.15 g (36.47 mmol) and tetrakistriphenylphosphine palladium 0.42 g (0.36 mmol) were introduced into a 500 ml three-necked flask equipped with a thermometer, a stirrer and a reflux condenser and dissolved 180 ml of in toluene. In addition, 90 ml of 2M sodium carbonate solution was added to the mixture and the reaction mixture was refluxed for 48 hours. After the reaction was completed, the reaction mixture was cooled down to room temperature, and the above solution was extracted with toluene three times. Combined extract was washed several times, and dried to anhydrous magnesium sulfate. In addition, the resultant was filtered and the solvent was removed to give viscous liquid. The liquid was purified by performing chromatography on silica gel column using ethyl acetate (1:2) mixture, after that recrystallized in a mixture of ethanol/chloroform to give yellow crystal. The crystal was dried in a vacuum oven at 40° C. and of desired product 4.7 g of desired product (yield: 50%). Mp:104-105° C.; $^1$H NMR (CDCl$_3$), δ 0.72-1.07 (m, 22H, CH$_2$ and CH$_3$), 2.01-2.18 (m, 4H, CCH$_2$), 3.83 (s, 4H, NH$_2$), 7.42-7.81 (m, 14H, aromatic).

Example 8

Synthesis of 2,7-bis(4-vinylphenyl)-9,9'-di-n-hexylfluorene (M-8)

In 500 ml three-necked flask equipped with a thermometer, a stirrer and a reflux condenser under nitrogen argon atmosphere, 2,7-dibromo-9,9'-di-n-hexylfluorene 20.0 g (40.6 mmol), 4-vinylphenylboron acid [H$_2$C=CHC$_6$H$_4$B(OH)$_2$] 13.3 g (89.4 mmol) and tetrakistriphenylphosphine palladium 0.46 g (0.4 mmol) were introduced and dissolved in toluene 200 ml, and 2M sodium carbonate 100 ml was added and refluxed for 48 hours. After the reaction was completed, the reaction mixture was cooled down to room temperature, and the mixture was extracted with toluene three times. Combined extract was washed with water several times and then dried with anhydrous magnesium sulfate. Solvent was removed to give viscous liquid. The obtained liquid was purified by performing chromatography on silica gel column using a mixture of ethyl acetate/hexane (1/3) and then crystallized in a mixture of ethyl acetate/hexane to give yellow crystal. The crystal was dried in vacuum oven at 40° C. to give 16.0 g of desired product (yield: 73%).

Mp: 106-107° C.; $^1$H NMR (CDCl$_3$): δ 0.75-1.16 (m, 22H, CH$_2$ and CH$_3$), 2.04-2.12 (m, 4H, CCH$_2$), 5.29-6.86 (m, 6H, vinyl), 7.53-7.82 (m, 14H, aromatic).

Example 9

Synthesis of 2,7-bis(3-chloromethylphenyl)-9,9'-di-n-hexylfluorene (M-9)

Under an argon atmosphere, 9,9'-di-n-hexylfluorene-2,7-diboron acid 2.0 g (4.7 mmol), 3-bromobenzylchloride (BrC$_6$H$_4$CH$_2$Cl) 2.14 g (10.4 mmol) and tetralystriphenylphosphine palladium 0.12 g (0.104 mmol) were introduced ito a is 250 ml three-necked flask equipped with a thermometer, a stirrer and a reflux condenser and dissolved in 50 ml of toluene. In addition, 25 ml of 2M sodium carbonate was added to the mixture and the reaction mixture was refluxed for 48 hours. After the reaction was completed, the reaction mixture was cooled down to room temperature and then extracted with toluene three times. Combined extract was washed with water several times and then dried with anhydrous magnesium sulfate. When the solvent was removed, viscous liquid was obtained. The liquid was purified by performing chromatography on silica gel column using a mixture of ethyl acetate/hexane (1:3) and then recrystallized in a mixture of ethyl acetate/hexane to give pale yellow crystal. The crystal was dried in a vacuum oven at 40° C. to give 1.2 g of desired product (yield: 43.5%).

Mp: 97-98° C.; $^1$H NMR (CDCl$_3$): δ 0.75-1.11 (m, 22H, CH$_2$ and CH$_3$), 2.05-2.13 (m, 4H, CCH$_2$), 4.73 (s, 4H, CH$_2$Cl), 7.41-7.84 (m, 14H, aromatic).

Example 10

Synthesis of 2,7-bis(toryl)-9,9'-di-n-hexylfluorene (M-10)

Under a nitrogen atmosphere, 2,7-dibromo-9,9'-di-n-hexylfluorene 40.0 g (81.3 mmol), 4-tolrylboron acid [CH$_3$C$_6$H$_4$B(OH)$_2$] 24.4 g (0.18 mmol) and tetrakystriphenylphosphine palladium 0.94 g (0.81 mmol) were introduced into a 1 L three-necked flask equipped with a thermometer, a stirrer and a reflux condenser and dissolved in 400 ml of toluene. In addition, 200 ml of 2M sodium carbonate was added to the mixture, and the reaction mixture was then refluxed for 48 hours. After the reaction was completed, the reaction mixture was cooled down to room temperature and extracted with toluene three times. Combined extract was washed with water several times and dried with anhydrous magnesium sulfate, and then solvent was removed, to give viscous liquid. The liquid was purified by performing chromatography on silica gel column using a mixture of ethyl acetate/hexane (1/2) as an eluent and then recrystallized in a mixture of ethyl acetate/hexane, to give pale yellow crystal. The crystal was dried in a vacuum oven at 40° C. to give 36.1 g of desired product (yield: 86%).

Mp: 88-89° C.; $^1$H NMR (CDCl$_3$): δ 0.76-1.10 (m, 22H, CH$_2$ and CH$_3$), 2.03-2.11 (m, 4H, CCH$_2$), 2.46 (s, 6H, CH$_3$), 7.31-7.82 (m, 14H, aromatic).

Example 11

Synthesis of 2,7-bis(4-carboxylphenyl)-9,9'-di-n-hexylfluorene (M-11)

Into a 1 L three-necked flask equipped with a thermometer, a stirrer and a reflux condenser, 2,7-bis(toryl)-9,9'-di-n-hexylfluorene 15.0 g (29.1 mmol) was introduced and dissolved in 270 ml of pyridine, and the resulting mixture was refluxed. After 50 ml of boiling water was added to the above solution, potassium permanganate (KmnO$_4$) 13.8 g (87.4 mmol) was also added for 4 hours. The mixture was then refluxed for 8 hours to give brown colored solution. To this solution, 350 ml of boiling water was added, and then the potassium permanganate 27.6 g was added for 6 hours. The resulting mixture was refluxed for 12 hours to give brown colored solution. The solution was filtered in a hot state and washed with boiling water several times, to give yellow colored solution. Concentrated hydrochloric acid was added to the solution to form white precipitate. The precipitate was filtered, washed with water and then dried in a vacuum oven at 50° C., to give 11.7 g of white solid (yield: 70%).

Mp: 290-2930C; $^1$H NMR (DMSO-d$_6$), δ 0.53-0.96 (m, 22H, CH$_2$ and CH$_3$), 0.96-2.11 (m, 4H, CCH$_2$), 7.71-8.05 (m, 14H, aromatic), 12.96 (br, s, 2H, COOH).

Example 12

Synthesis of 2,7-bis(4-chlorocarbonylphenyl)-9,9'-di-n-hexylfluorene (M-12)

Under an argon atmosphere, 2,7-bis(carboxylphenyl)-9,9'-di-n-hexylfluorene 6.0 g (10.4 mmol) and thionyl chloride (SOCl$_2$) 30 ml were introduced into a 50 ml three-necked flask equipped with a thermometer, a stirrer and a reflux condenser, and the mixture was heated to dissolve the starting material. Dimethylformamide 1 ml was then added to the mixture, and the resulting mixture was refluxed for 12 hours. The reaction mixture was cooled down to room temperature, the solvent was entirely removed under a reduced pressure, and then diethyl ether was added to the residue. Dissolved part in diethyl ether was separated from undissolved part and concentrated by removing solvent. The residue was recrystallized in a mixture of petrollium ether/diethyl ether to give yellow crystal. The obtained solid was filtered and dried in a vacuum oven at 40° C. to give 4.3 g of desired product (yield: 67%).

Mp: 130-131° C.; $^1$H NMR (CDCl$_3$), δ 0.71-1.12 (m, 22H, CH$_2$ and CH$_3$), 2.03-2.11 (m, 4H, CCH$_2$), 7.61-8.25 (m, 14H, aromatic).

Example 13

Synthesis of 2,7-bis(3-ethylformatylphenyl)-9,9'-di-n-hexylfluorene (M-13)

Under an argon atmosphere, 9,9'-di-n-hexylfluorene-2,7-diboron acid 10.0 g (23.7 mmol), ethyl 3-bromobenzoate 11.9 g (52.1 mmol) and tetrakistriphenylphosphine palladium 0.6 g (0.52 mmol) were introduced into a 500 ml three-necked flask equipped with a thermometer, a stirrer and a reflux condenser, and dissolved in 260 ml of toluene. 130 ml of 2M sodium carbonate solution was added to the mixture, and the resulting mixture was refluxed for 48 hours. After the reaction was completed, the reaction mixture was cooled down to room temperature and extracted with toluene three times. Combined extract was washed with water several times and dried with anhydrous magnesium sulfate, and then solvent was removed, to give viscous liquid. The liquid was purified by performing chromatography on silica gel column using a mixture of ethyl acetate/hexane (1/3) as an eluent and then recrystallized in a mixture of ethanol/acetone to give white crystal. The crystal was dried in a vacuum oven at 40° C. to give 11 g of desired product (yield: 73.8%).

Mp: 94-95° C.; $^1$H NMR (CDCl$_3$), δ 0.70-1.06 (m, 22H, CH$_2$ and CH$_3$), 1.39-1.46 (t, 6H, CH$_3$), 2.00-2.08 (m, 4H, CCH$_2$), 4.37-4.48 (q, 4H, OCH$_2$), 7.50-8.35 (m, 14H, aromatic).

Example 14

Synthesis of 2.7-bis(4-ethylformatylephenyl)-9,9'-di-n-hexylfluorene (M-14)

Under an argon atmosphere, 9,9'-di-n-hexylfluorene-2,7-diboron acid 10.0 g (23.7 mmol), ethyl 4-bromobenzoate 11.9 g (52.1 mmol) and tetrakistriphenylphosphine palladium 0.6 g (0.52 mmol) were introduced into a 500 ml three-necked flask equipped with a thermometer, a stirrer and a reflux condenser and dissolved in 260 ml of toluene. 130 ml of 2M sodium carbonate solution was then added to the mixture, and the resulting mixture was refluxed for 48 hours. After the reaction was completed, the reaction mixture was cooled down to room temperature and extracted with toluene three times. Combined extract was washed with water several times and dried with anhydrous magnesium sulfate, and then solvent was removed to give viscous liquid. The liquid was purified by performing chromatography on silica gel column using a mixture of ethyl acetate/hexane (1:3) as an eluent and then recrystallized in a mixture of ethanol/acetone to give white crystal. The crystal was dried in a vacuum oven at 40° C. to give 9 g of desired product (yield: 60%).

Mp: 100° C.; $^1$H NMR (CDCl$_3$), δ 0.72-1.05 (m, 22H, CH$_2$ and CH$_3$), 1.40-1.44 (t, 6H, CH$_3$), 2.00-2.08 (m, 4H, CCH$_2$), 4.38-4.45 (q, 4H, OCH$_2$), 7.58-8.14 (m, 14H, aromatic).

Example 15

Synthesis of 1,4-bis(3-nitrophenyl)-3,6-di-hexyloxybenzen (M-15)

Under an argon atmosphere, 1,4-dibromo-3,6-di-hexyloxybenzen 20.0 g (45.8 mmol), 3-nitrobenzenboron acid [(O$_2$NC$_6$H$_4$B(OH)$_2$)] 16.8 g (0.1 mol) and tetrakistriphenylphosphine palladium 0.53 g (0.46 mmol) were introduced into a 500 ml three-necked flask equipped with a thermometer, a stirrer and a reflux condenser, and dissolved in 200 ml of toluene. After adding 100 ml of 2M sodium carbonate solution to the mixture, the resulting mixture was refluxed for 48 hours. After the reaction was completed, the reaction mixture was cooled down to room temperature and extracted with toluene three times. Combined extract was washed with water several times and dried with anhydrous magnesium sulfate, and then solvent was removed to give viscous liquid. The liquid was purified by performing chromatography on silica gel column using a mixture of ethyl acetate/hexane (1/3) as an eluent and then recrystallized in a mixture of ethyl acetate/hexane to give yellow fine crystal. The crystal was dried in a vacuum oven at 40° C. to give 12 g of desired product (yield: 50%).

Mp: 126-127° C.; $^1$H NMR (CDCl$_3$), δ 0.87-1.77 (m, 22H, CH$_2$ and CH$_3$), 3.91-3.98 (m, 4H, OCH$_2$), 7.01-8.51 (m, 10H, aromatic).

Example 16

Synthesis of 1,4-bis(3-aminophenyl)-3,6-di-hexyloxybenzen (M-16)

Into a 500 ml three-necked flask equipped with a stirrer, 1,4-bis(3-nitrophenyl)-3,6-di-hexyloxybenzene 9.0 g (17.3 mmol) and 10 wt % palladium activated carbon (Pd/C) 2 g were introduced and dissolved in 200 ml of THF, and then the resulting mixture was reacted for 24 hours at room temperature while filling hydrogen gas therein. After the reaction was completed, the reaction mixture was dried with anhydrous magnesium sulfate, and then solvent was removed to give white crystal. The crystal was dried in a vacuum oven at 40° C. to give 7.0 g of desired product (yield: 88%).

Mp: 105-106° C.; $^1$H NMR (CDCl$_3$), δ 0.81-1.69 (m, 22H, CH$_2$ and CH$_3$), 3.57 (br, s, 4H, NH$_2$) 3.83-3.89 (m, 4H, OCH$_2$), 6.62-7.24 (m, 10H, aromatic).

Example 17

Synthesis of 2,7-bis(4-bromophenyl)-9,9(-di-n-hexylfluorene (M-17)

Into a 1 L three-necked flask equipped with a thermometer, a stirrer and a reflux condenser, 2,7-diphenyl-9,9(-di-n-hexylfluorene 50.0 g (0.1 mol) was introduced and dissolved in 400 ml of methylenechloride, and then the solution was cooled down to −5° C. using ice-salt bath. Bromine 33.6 g (0.21 mol) which was diluted in 100 ml of methylenechloride was added dropwise to the solution, and then the resulting mixture was reacted for 24 hours at 25° C. After the reaction was completed, 20% aqueous potassium hydroxide solution was gradually added to the solution until red color of the solution was disappeared, and then an organic layer was separated and washed with water several times. The solution was dried with anhydrous magnesium sulfate, and then solvent was removed to give viscous liquid. The liquid was dissolved in hexane and cooled down to −40° C., to give solid. The obtained solid was recrystallized in hexane two times to obtain pure white crystal. The crystal was filtered and dried in a vacuum oven at 40° C. to give 55 g of desired product (yield: 83.66%).

Mp: 121-123° C.; $^1$H NMR (CDCl$_3$), δ 0.71-1.06 (m, 22H, CH$_2$ and CH$_3$), 1.99-2.06 (m, 4H, CCH$_2$), 7.45-7.78 (m, 16H, aromatic).

Example 18

Synthesis of 2,7-bis(4-ethinylphenyl)-9,9'-di-n-hexylfluorene (M-18)

Into a 250 ml flask equipped with a thermometer and a stirrer, 2,7-bis[4-((trimethylsilyl)ethinyl)phenyl]-9,9'-di-n-hexylfluorene 4.0 g (5.8 mmol) and 20 wt % potassium fluoride 6 ml were introduced and dissolved in 100 ml of methanol, and then the resulting mixture was reacted for 6 hours at room temperature. After the reaction was completed, methanol 50 ml was added, and the solvent was removed under a vacuum condition. The residue was extracted with ether three times, and combined extract was washed with water several times and dried with magnesium sulfate. After removing solvent, the residue was purified by performing chromatography on silica gel column using a mixture of hexane/methylenechloride (4/1) as an eluent and then recrystallized in hexane to give 2.8 g of desired product as pale yellow solid (yield: 90%).

Mp: 101-102° C.; $^1$H NMR (CDCl$_3$), δ 0.78-1.42 (m, 22H, CH$_2$ and CH$_3$), 2.02-2.1 (m, 4H, CCH$_2$), 3.19 (s, 2H, CH), 7.42-7.78 (m, 14H, aromatic).

Example 19

Synthesis of 2,7-bis(4-aldehydephenyloxyphenyl)-9,9'-di-n-hexylfluorene (M-19)

Under an argon atmosphere, 2,7-bis(4-hydroxyphenyl)-9,9'-di-n-hexylfluorene 4.0 g (7.7 mmol), 4-fluorobenzaldehyde 1.96 g (15.8 mmol) and potassium carbonate 2.13 g (15.4 mmol) were introduced into a 100 ml three-necked flask equipped with a thermometer, a stirrer and a reflux condenser and dissolved in 25 ml of dimethyl acetamide (DMAc), and the resulting mixture was refluxed for 8 hours at 120° C. After the reaction was completed, the reaction mixture was cooled down to room temperature and then gradually dropped into 400 ml of water to form solid. The solid was filtered and dissolved in diethyl ether, and then the solution was washed with water several times and dried with anhydrous magnesium sulfate. After removing solvent the residue was recrystallized in a mixture of ethyl acetate/hexane to give white solid. The solid was dried in a vacuum oven at 40° C. to give 4.3 g of desired product (yield: 76.7%).

Mp: 86-88° C.; $^1$H NMR (CDCl$_3$), δ 0.73-1.09 (m, 22H, CH$_2$ and CH$_3$), 2.03-2.10 (m, 4H, CCH$_2$), 7.13-7.91 (m, 22H, aromatic), 9.95 (s, 2H, CHO).

Example 20

Synthesis of 2,7-bis(4-nitrophenyloxyphenyl)-9,9'-di-n-hexylfluorene (M-20)

Under an argon atmosphere, 2,7-bis(4-hydroxyphenyl)-9,9'-di-n-hexylfluorene 6.0 g (11.6 mmol), 1-fluoro-4-nitrobenzene 3.3 g (23.7 mmol) and potassium carbonate 3.2 g (23.1 mmol) were introduced into a 100 ml three-necked flask equipped with a thermometer, a stirrer and a reflux condenser and dissolved in 35 ml of dimethyl acetamide, and the resulting mixture was refluxed for 8 hours at 120° C. After the reaction was completed, the reaction mixture was cooled down to room temperature and gradually dropped into 400 ml of water to form solid. The solid was filtered and dissolved in diethyl ether, and then the solution was washed with water several times and dried with anhydrous magnesium sulfate. After removing solvent, the residue was recrystallized in a mixture of ethyl acetate/hexane to give pale yellow solid. The solid was dried in a vacuum oven at 40° C. to give 7.2 g of desired product (yield: 79.8%).

Mp: 102-103° C.; $^1$H NMR (CDCl$_3$), δ 0.73-1.09 (m, 22H, CH$_2$ and CH$_3$), 2.03-2.11 (m, 4H, CCH$_2$), 7.06-8.28 (m, 22H, aromatic).

Example 21

Synthesis of 2,7-bis(4-aminophenyloxyphenyl)-9,9'-di-n-hexylfluorene (M-21)

Into a 500 ml two-necked flask equipped with a stirrer, 2,7-bis(4-nitrophenyloxyphenyl)-9,9'-di-n-hexylfluorene 6.0 g (7.9 mmol) and 10 wt % palladium activated carbon (Pd/C) 2 g were introduced and dissolved in 200 ml of THF, and then the resulting mixture was reacted for 24 hours at room temperature while filling hydrogen gas therein. When the reaction was completed, the reaction mixture was dried with anhydrous magnesium sulfate, and then solvent was removed to give viscous liquid. The liquid was recrystallized in a mixture of ethyl acetate/hexane mixture to give yellow crystal. The crystal was dried in a vacuum oven at 40° C. to give 4.7 g of desired product (yield: 85%).

Mp: 57-58° C.; $^1$H NMR (CDCl$_3$), δ 0.71-1.05 (m, 22H, CH$_2$ and CH$_3$), 2.01-2.05 (m, 4H, CCH$_2$), 6.68-7.75 (m, 22H, aromatic).

Example 22

Synthesis of 2,7-bis(3-carboxylphenyl)-9,9'-di-n-hexylfluorene (M-22)

Under an argon atmosphere, 2,7-bis(3-ethylformatylephenyl)-9,9'-di-n-hexylfluorene 15.0 g (23.8 mmol) was introduced into a 500 ml three-necked flask equipped with a thermometer, a stirrer and a reflux condenser and dissolved in 100 ml of THF. 100 ml of 1M aqueous lithium hydroxide solution was added to the mixture, and the resulting mixture was refluxed for 5 hours. When the reaction was completed, THF was removed, and then concentrated hydrochloric acid solution was gradually added to the residue while stirring to form solid. The solid was filtered, washed with water completely and then put into hexane. The mixture was stirred for two hours and then filtered to obtain pale yellow solid. The solid was dried in a vacuum oven at 40° C. to give 13.1 g of desired product (yield: 95%).

Mp: 227-229° C.; $^1$H NMR (DMSO-d$_6$), δ 0.58-0.92 (m, 22H, CH$_2$ and CH$_3$), 2.05-2.09 (m, 4H, CCH$_2$), 7.5-8.28 (m, 14H, aromatic).

Example 23

Synthesis of 2,7-bis(3-chlorocarbonylphenyl)-9,9'-di-n-hexylfluorene (M-23)

Under an argon atmosphere, 2,7-bis(3-carboxyphenyl)-9,9'-di-n-hexylfluorene 8.0 g (13.9 mmol) was introduced into a 50 ml three-necked flask equipped with a thermometer, a stirrer and a reflux condenser and was dissolved in 40 ml of thionyl chloride by heating. 2 ml of dimethyl formamide (DMF) was added to the solution and the resulting mixture was refluxed for 24 hours. After the reaction was completed, the reaction mixture was cooled down to room temperature, and solvent was totally removed under a reduced pressure. Cyclohexane was added to the residue, and dissolved part in cyclohexane was separated from undissolved part and concentrated by removing solvent. The residue was dissolved and then recrystallized in hexane to give yellow crystal. The crystal was filtered and dried in a vacuum oven at 40° C. to give 6.0 g of desired product (yield: 70%).

Mp: 113-114° C.; $^1$H NMR (CDCl$_3$), δ 0.72-1.13 (m, 22H, CH$_2$ and CH$_3$), 2.04-2.11 (m, 4H, CCH$_2$), 7.26-8.41 (m, 14H, aromatic).

Example 24

Synthesis of 2,7-bis(4-hydroxymethylphenyl)-9,9'-di-n-hexylfluorene (M-24)

Under an argon atmosphere, 2,7-bis(4-ethylformatylephenyl)-9,9-di-n-hexylfuorene 6.0 g (9.5 mmol) was introduced into a 250 ml three-necked flask equipped with a dropping funnel, a stirrer and a reflux condenser and dissolved in 30 ml of anhydrous THF. 1M LiAlH$_4$ solution in 40 ml of anhydrous THF was prepared and rapidly added to the mixture using the dropping funnel, and the resulting mixture was refluxed for 24 hours. After an ice-bath was installed, to the reaction mixture, water and 16 wt % NaOH solution was gradually added sequentially. The precipitate was filtered and washed with chloroform, and then the filtrate solution was extracted with chloroform and washed with water. Combined extract was dried with anhydrous magnesium sulfate and concentrated by removing chloroform under a reduced pressure. The residue was recrystallized in a mixture of ethyl acetate/hexane to give white solid. The solid was dried in a vacuum oven at 40° C. to give 5.1 g of desired product (yield: 96%).

Mp: 113-114° C.; $^1$H NMR (CDCl$_3$), δ 0.73-1.07 (m, 22H, CH$_2$ and CH$_3$), 1.89 (s, 2H, OH), 2.01-2.09 (m, 4H, CCH$_2$), 4.78 (s, 4H, CH$_2$), 7.47-7.80 (m, 14H, aromatic).

Example 25

Synthesis of 2,7-bis(4-chloromethylphenyl)-9,9'-di-n-hexylfluorene (M-25)

Under an argon atmosphere, 2,7-bis(4-hydroxymethylphenyl)-9,9'-di-n-hexylfluorene 4.0 g (7.31 mmol) was introduced into a 100 ml three-necked flask equipped with a thermometer, a stirrer and a reflux condenser and dissolved in 50 ml of methylenechloride, and then thionyl chloride 1.4 ml and pyridine 0.05 ml were added to the mixture. The reaction mixture was refluxed for 12 hours and cooled down to room temperature, and then methylenechloride, thionyl chloride and pyridine were removed under a reduced pressure. The residual solid was purified by performing chromatography on silica gel column using a mixture of hexane/ethyl acetate (5/1) as an eluent and then recrystallized in a mixture of chloroform/methanol to give white crystal. The solid was filtered and dried in a vacuum oven at 40° C., to give 4.1 g of desired product (yield: 94%).

Mp: 104-105° C.; $^1$H NMR (CDCl$_3$), δ 0.73-1.13 (m, 22H, CH$_2$ and CH$_3$), 2.00-2.08 (m, 4H, CCH$_2$), 4.68 (s, 4H, CH$_2$Cl), 7.49-7.81 (m, 14H, aromatic).

Example 26

Synthesis of 2,7-bis(4-hydrazidephenyl)-9,9'-di-n-hexylfluorene (M-26)

Into a 100 ml three-necked flask equipped with a thermometer, a stirrer and a reflux condenser under an argon atmosphere, 2,7-bis(3-ethylformatylephenyl)-9,9'-di-n-hexylfluorene 5.0 g (7.92 mmol) was introduced and dissolved in 35 ml of butyl alcohol by heating, and then hydrazine monohydrate 6 ml was added. The resulting mixture was reacted for 48 hours at 80° C., cooled down to room temperature and extracted with ethyl acetate, sequentially. Combined extract was washed with water, and then ethyl acetate was removed except a small amount. The residue was dropped into hexane to form precipitate and washed for one hour, and then the solid was filtered and dried in a vacuum oven at 40° C., to give 2.0 g of desired product (yield: 42%).

Mp: 134-136° C.; $^1$H NMR (CDCl$_3$), δ 0.72-1.19 (m, 22H, CH$_2$ and CH$_3$), 2.03-2.10 (m, 4H, CH$_2$), 4.21 (br, s, 4H, NH$_2$), 7.51 (s, 2H, NH), 7.60-7.90 (m, 14H, aromatic).

Example 27

Synthesis of 2,7-bis(3-hydrazidephenyl)-9,9'-di-n-hexylfluorene (M-27)

Under an argon atmosphere, 2,7-bis(3-ethylformatylephenyl)-9,9'-di-n-hexylfluorene 5.0 g (7.92 mmol) was introduced into a 100 ml three-necked flask equipped with a thermometer, a stirrer and a reflux condenser and dissolved in 35 ml of butyl alcohol by heating, and then hydrazine monohydrate 6 ml was added. The resulting mixture was reacted for 48 hours at 80° C., cooled down to room temperature and then extracted with ethyl acetate. Combined extract was washed with water and dried with anhydrous magnesium sulfate, and then ethyl acetate was removed except a small amount. The residue was dropped into hexane to form precipitate and washed for one hour. The solid was filtered and dried in a vacuum oven at 40° C. to give 2.5 g of desired product (yield: 52.4%).

Mp: 106-108° C.; $^1$H NMR (CDCl$_3$), δ 0.72-1.06 (m, 22H, CH$_2$ and CH$_3$), 2.03-2.11 (m, 4H, CH$_2$), 4.21 (br, s, 4H, NH$_2$), 8.09 (s, 2H, NH), 7.60-7.90 (m, 14H, aromatic).

Example 28

Synthesis of 2,7-bis(4-methoxyphenyl)-9,9'-di-n-hexylfluorene (M-28)

Under an argon atmosphere, 2,7-(dibromo)-9,9'-di-n-hexylfluorene 45.1 g (81.4 mmol), p-methoxyphenylboronic acid 32.0 g (0.21 mol) and tetrakistriphenylphosphinine palladium 1.06 g (1 mmol) were introduced into a round bottom flask equipped with a condenser and a stirrer and dissolved in 600 ml of toluene, and then 400 ml of 2M aqueous potassium carbonate solution was added. The resulting mixture was reacted for 48 hours at 120° C. and extracted with toluene several times. Combined extract was washed with water several times, dried with anhydrous magnesium sulfate, and then solvent was removed. The residue was purified by performing chromatography on silica gel column using ethyl acetate (5/1) as an eluent and then recrystallized in ethyl acetate/hexane, to give 41.5 g of desired product (yield: 83%).

Mp: 104-105° C.; $^1$H NMR (CDCl$_3$), δ 0.76-1.16 (m, 22H, CH$_2$ and CH$_3$), 2.10-2.11 (m, 4H, CCH$_2$), 3.91 (s, 6H, OCH$_3$), 7.03-7.75 (m, 14H, aromatic).

Example 29

Synthesis of 2,7-bis(4-hydroxyphenyl)-9,9'-di-n-hexylfluorene (M-29)

Into a round bottom flask, 2,7-bis(4-methoxyphenyl)-9,9'-di-n-hexylfluorene 30.0 g (54.9 mmol) was introduced and dissolved in 400 ml of methylenechloride, and then 220 ml of 1 M triboromoborate was added dropwise for one hour at –76° C. The mixture was reacted at –76° C. for one hour, allowed to reach room temperature and then reacted for 24 hours at room temperature. Hydrolysis was carried out by adding water to the reaction mixture, and then organic layer was separated. 2N sodium hydroxide was added to the organic layer to form alkaline solid, and then diluted hydrochloric acid was added to neutralize and to make a clear solution by dissolving the solid. The resulting solution was extracted with ether. Combined extract was washed with distilled water several times and dried with anhydrous magnesium sulfate and then concentrated. The residue was purified by performing chromatography on silica gel column using a mixture of ethyl acetate/hexane (1:10) as an eluent and then recrystallized in ether, to give 21.8 g of desired product (yield: 76.6%).

Mp: 142-143° C.; $^1$H NMR (DMSO-d$_6$), δ 0.61-1.16 (m, 22H, —CH$_2$— and —CH$_3$), 2.10-2.12 (m, 4H, —CCH$_2$—), 6.89-7.85 (m, 14H, aromatic), 9.57 (s, 2H, —OH).

Example 30

Synthesis of 2,7-bis(4-cyanatephenyl)-9,9'-di-n-hexylfluorene (M-30)

Under an argon atmosphere, 2,7-bis(4-hydroxyphenyl)-9,9'-di-n-hexylfluorene 10.0 g (19.3 mmol) and bromocyanide 6.1 g (57.9 mmol) were introduced into a round bottom flask and dissolved in 100 ml of acetone by stirring, and then 8 ml of triethylamine was added dropwise for 30 minutes at –30° C. The resulting mixture was reacted for 10 hours while allowing to reach room temperature. The reaction was quenched by adding 500 ml of water, and the reaction mixture was extracted with methylenechloride. Combined organic extract was washed with distilled water several times, dried with anhydrous magnesium sulfate and then concentrated. The residue was recrystallized in ethyl acetate to give 8.7 g of desired product (yield: 79.4%).

Mp: 125-126° C.; $^1$H NMR (CDCl$_3$), δ 0.74-1.08 (m, 22H, —CH$_2$— and —CH$_3$—), 2.03-2.07 (m, 4H, —CCH$_2$—), 7.40-7.84 (m, 14H, aromatic).

Example 31

Synthesis of 2,7-bis[4-(3,4-dicyanophenoxy)phenyl]-9,9'-di-n-hexylfluorene (M-31)

Into a round bottom flask equipped with dean-stark device, 2,7-bis(4-hydroxyphenyl)-9,9'-di-n-hexylfluorene 10.0 g (19.3 mmol) was introduced and dissolved in 50 ml of DMF and 40 ml of toluene, and then potassium carbonate 5.6 g (40.5 mmol) was added. The reaction mixture was refluxed while maintaining the temperature at 140° C. After removing water and toluene completely from the dean-stark device, the temperature was cooled down to 60° C. p-nitrophthalonitrile 6.93 g (40.5 mmol) was added to the mixture, and then the resulting mixture was reacted for 24 hours at the same temperature. The reaction mixture was precipitated in 1000 ml of water, and then the precipitate was filtered and dried at 60° C. under a reduced pressure. The residue was purified by performing chromatography on silica gel column using hexane/ethyl acetate (4/1) as the elution solvent and then recrystallized in ethyl acetate to give 10.2 g of desired product (yield: 69%).

Mp: 183-184° C.; $^1$H NMR (CDCl$_3$), δ 0.68-0.81 (m, 22H, —CH$_2$— and —CH$_3$), 2.06-2.08 (m, 4H, —CCH$_2$—), 7.14-7.80 (m, 20H, aromatic).

Example 32

Synthesis of 2,7-bis[4-(3,4-dicarboxyphenoxy)phenyl]-9,9'-di-n-hexylfluorene (M-32)

Into a round bottom flask, 2,7-bis[4-(3,4-dicyanophenoxy)phenyl]-9,9'-di-n-hexylfluorene 10 g (13 mmol), potassium hydroxide 14.6 g (0.26 mmol), 75 ml of distilled water and 75 ml of ethanol were introduced, and the mixture was refluxed for 3 days with stirring. After the hot reaction mixture was filtered to remove impurities which were not dissolved, the pH of the solution was adjusted to be 2-3 by adding hydrochloric acid to give solid. The solid was filtered, washed with water several times, neutralized, dried at 60° C. for 24 hours under a reduced the pressure and recrystallized in a mixture of ethyl acetate and normal hexane, sequentially, thereby to obtain 8.6 g of desired product as white crystal (yield 78.3%).

Mp: 214-215° C.; $^1$H NMR (DMSO-d$_6$), δ 0.58-1.20 (m, 22H, CH$_2$ and CH$_3$), 2.16-2.20 (m, 4H, CCH$_2$), 7.16-7.92 (m, 20H, aromatic).

Example 33

Synthesis of 2,7-bis[4-(3,4-dicarboxyphenoxy)phenyl]-9,9'-di-n-hexylfluorene dianhydride (M-33)

Into a round bottom flask, 2,7-bis[4-(3,4-dicarboxyphenoxy)phenyl]-9,9'-di-n-hexylfluorene 5.0 g (5.9 ml) and acetic anhydride 50 ml were introduced, and the resulting mixture was refluxed for 24 hours. After the hot solution was filtered to remove impurities which were not dissolved, the solution was cooled down slowly to give 3.75 g of desired product (yield: 78%).

Mp: 187-188° C.; $^1$H NMR (CDCl$_3$), δ 0.76-1.12 (m, 22H, CH$_2$ and CH$_3$), 2.13-2.15 (m, 4H, CCH$_2$—), 7.24-8.04 (m, 20H, aromatic).

Example 34

Synthesis of 2,7-bis(4-acetylephenyl)-9,9'-di-n-hexylfluorene (M-34)

Into a 1.0 L round bottom flask equipped with a condenser and a dripping funnel, after 2,7-bis(diphenyl)-9,9'-di-n-hexylfluorene 30.0 g (61.6 mmol) was introduced and dissolved in 500 ml of carbondisulfide with stirring at room temperature, aluminum trichloride 24.66 g (185 mmol) was added at 0° C. Acetyl chloride 14.5 g (185 mmol) was added dropwise to the resulting solution for an hour using the dripping funnel, and then the reaction mixture was refluxed for 24 hours. The reaction mixture was poured into a mixture of 2M hydrochloric acid and ice to quench the reaction and extracted with methylenechloride. Combined organic extract was washed with water, dried with anhydrous magnesium sulfate and then concentrated. The residue was purified by performing chromatography on silica gel column using methylenechloride/hexane (1/10) as an elution solvent and then recrystallized in methylenechloride/hexane, thereby to obtain 23.5 g of desired product (yield: 66.8).

Mp: 130-131° C.; $^1$H NMR (CDCl$_3$), δ 0.73-0.79 (m, 22H, CH$_2$ and CH$_3$), 2.07 (m, 4H, CCH$_2$—), 2.68 (s, 6H, COCH$_3$), 7.63-8.12 (m, 14H, aromatic).

Example 35

Synthesis of 2,7-bis(4-cyanophenyl)-9,9'-di-n-hexylfluorene (M-35)

After 2,7-bis(4-bromophenyl)-9,9'-di-n-hexylfluorene 10.0 g (15.5 mmol) and cyanide copper 4.g (46.5 mmol) were introduced into a round bottom flask equipped with a condenser and dissolved in 60 ml of dimethylformamide (DMF), the reaction mixture was refluxed for 48 hours with stirring. The reaction mixture was poured into 1.0 L of 15% aqueous ammonia solution to generate precipitate. The precipitate was collected with filtering, washed with 15% and 10% aqueous ammonia solution and distilled water, and then dried to remove moisture under a reduced pressure at 60° C. The residue was dissolved in hot acetone, and the solution was filtered to remove impurities which were not dissolved in acetone and concentrated. The residue was purified by performing chromatography on silica gel column using a mixture of ethyl acetate/hexane (1/1) as the elution solvent and then recrystallized in a mixture of ethyl acetate/hexane, thereby to obtain 6.6 g of desired product (yield: 79.4%).

Mp: 113-115° C.; $^1$H NMR (CDCl$_3$), δ 0.71-1.58 (m, 22H, CH$_2$ and CH$_3$), 2.01-2.08 (m, 4H, CCH$_2$), 7.56-7.85 (m, 14H, aromatic).

Example 36

Synthesis of 2,7-bis(p-hydroxystyryl)-9,9'-di-n-hexylfluorene (M-36)

Under a nitrogen atmosphere, 2,7-bis(p-acetoxystyryl)-9,9'-di-n-hexylfluorene 32.7 g (0.05 mol) and KOH 28.0 g (0.5 mol) were introduced into a 500 ml three-necked flask equipped with a stirrer, a thermometer and a reflux condenser and dissolved in 200 ml of methanol, and then the resulting mixture was refluxed for 12 hours. The reaction mixture was cooled down to room temperature and then dropped into 2.0 L of 2.0N aqueous hydrochloric acid to generate solid. The generated solid was filtered, washed with water and dissolved in toluene. The solution was distilled to remove water with toluene from the crude solid product. The solid was recrystallized in toluene two times to give 27.1 g of desired product as pure yellow solid (yield: 95%).

Mp: 96-97° C.; $^1$H NMR (CDCl$_3$), δ 0.56-1.15 (m, 22H, CH$_2$ and CH$_3$), 2.00 (br, 4H, CH$_2$), 5.10 (br, s, 2H, OH), 6.82-6.86 (d, 4H, vinyl), 7.08-7.64 (m, 14H, aromatic).

Example 37

Synthesis of 2,7-bis[4-(3,4-dicarboxyphenoxy)phenylenevinyl]-9,9'-di-n-hexylfluorene dianhydride (M-37)

After 2,7-bis[4-(3,4-dicarboxyphenoxy)phenylenevinyl]-9,9'-di-n-hexylfluorene 3.0 g (3.3 mmol), acetic anhydride 15 ml, and acetic acid 15 ml were introduced into a 250 ml three-necked flask equipped with a thermometer, a stirrer and a reflux condenser, the resulting mixture was refluxed for 24 hours. The hot solution was filtered to remove the undissolved impurities and slowly cooled down, to give 1.9 g of desired product (yield: 67%).

Mp: 190-193° C.; $^1$H NMR (CDCl$_3$), δ 0.71-1.25 (m, 22H, CH$_2$ and CH$_3$), 2.00 (br, 4H, CH$_2$), 6.82-6.86 (d, 4H, vinyl), 7.09-7.65 (m, 20H, aromatic).

Example 38

Synthesis of 2,7-bis(4-fluorostyryl)-9,9'-di-n-hexylfluorene (M-38)

Under an argon atmosphere, 2,7-dibromo-9,9'-di-n-hexylfluorene 17.7 g (36 mmol), 4-fluorostyrene log (82 mmol), palladium (II) acetate 0.113 g, tri-o-tolylphosphine 1.13 g, tri-n-butylamine 17 ml and 60 ml of DMF were introduced into a 250 ml three-necked flask equipped with a thermometer, a stirrer and a reflux condenser, and then the resulting mixture was reacted for 24 hours at 100° C. The reaction mixture was cooled down to room temperature, extracted with diethyl ether and washed with water. Combined organic extract was dried with anhydrous magnesium sulfate and concentrated under a reduced pressure. The residue was recrystallized using hexane/ethyl acetate to give yellow solid. The solid was dried in a vacuum oven at 40° C. to give 11.1 g of desired product (yield: 53%).

Mp: 110-111° C.; $^1$H NMR (CDCl$_3$), δ 0.66-1.15 (m, 22H, CH$_2$ and CH$_3$), 1.95-2.00 (br, 4H, CH$_2$), 7.08-7.65 (m, 14H, aromatic, 4H, vinyl).

Example 39

Synthesis of 2,7-bis(3-nitrostyryl)-9,9'-di-n-hexylfluorene (M-39)

Under an argon atmosphere, after 2,7-dibromo-9,9'-di-n-hexylfluorene 33.0 g (67 mmol), 3-nitrostyrene 25 g (168 mmol), palladium (II) acetate 0.151 g, tri-o-tolylphosphine 1.232 g and triethylamine 15 g were introduced into a 250 ml three-necked flask equipped with a thermometer, a stirrer and a reflux condenser, 100 ml of DMF was added, and then the resulting mixture was reacted for 24 hours at 100° C. The reaction mixture was then cooled down to room temperature and then dropped into 1 L of methanol containing small amount of hydrochloride acid, to generate solid. The solid was filtered, washed with methanol and then dried in a vacuum oven at 40° C., to give 31.5 g of desired product (yield: 75%).

Mp: 189-192° C.; $^1$H NMR (CDCl$_3$), δ 0.66-1.15 (m, 22H, CH$_2$ and CH$_3$), 1.95-2.00 (m, 4H, CH$_2$), 7.15-8.48 (m, 14H, aromatic, 4H, vinyl).

Example 40

Synthesis of 2,7-bis(4-nitrostyryl)-9,9'-di-n-hexylfluorene (M-40)

Under an argon atmosphere, after 2,7-dibromo-9,9'-di-n-hexylfluorene 33.0 g (67 mmol), 4-nitrostyrene 25 g (168 mmol), palladium (II) acetate 0.151 g, tri-o-tolylphosphine 1.232 g and triethylamine 15.g were introduced into a 250 ml three-necked flask equipped with a thermometer and a reflux condenser, 100 ml of DMF was added, and then the resulting mixture was reacted for 24 hours at 100° C. The reaction mixture was then cooled down to room temperature and then dropped into 1 L of methanol containing small amount of hydrochloric acid, thereby to generate solid. The solid was filtered, washed with methanol and then dried in a vacuum oven at 40° C., to give 33 g of desired product (yield: 78%).

Mp: 164-166° C.; $^1$H NMR (CDCl$_3$), δ 0.66-1.15 (m, 22H, CH$_2$ and CH$_3$), 1.95-2.00 (m, 4H, CH$_2$), 7.15-7.81 (m, 14H, aromatic, 4H, vinyl).

Synthesis of Polymers

Example 41

Polymerization of 2,7-bis(4-aminophenyl)-9,9'-di-n-hexylfluorene (M-3) and isophtalaldehyde (P-1, P-1-1 and P-1-2)

Under a nitrogen atmosphere, 2,7-bis(4-aminophenyl)-9,9'-di-n-hexylfluorene 0.516 g (1 mmol), isophtalaldehyde 0.1 34 g (1 mmol), p-toluenesulfonic acid monohydrate 3.0 mg (0.016 mmol) and calcium chloride 0.224 g were introduced into a 50 ml flask equipped with a stirrer and dissolved in 3 ml of hexamethylphosphoramide and 3 ml of dimethyl sulfoxide, and then the resulting mixture was reacted for 24 hours at room temperature. The reaction mixture was slowly dropped into 1 L of methanol to deposit the produced polymer. The polymer was filtered, dissolved again in chloroform and then reprecipitated in methanol. The reprecipitated polymer was filtered, washed thoroughly with methanol and then dried in a vacuum oven at 40° C., thereby to obtain 0.57 g of yellow-colored polymer (yield: 92.8%).

$^1$H NMR (CDCl$_3$), δ 0.76-1.1 (CH$_2$ and CH$_3$), 2.08 (br, s, CCH$_2$), 7.39-8.52 (m, aromatic), 8.68 (s, ArCH=NAr).

When P-1 polymer which has not exhibited photoluminescence was dissolved in chloroform and, to this solution, one drop of an inorganic acid such as concentrated hydrochloric acid, acid-added polymer (P-1-1) was formed, and this acid-added polymer exhibited photoluminescence. In the same manner, when the P-1 polymer was dissolved in chloroform and, to this solution, small amount of an organic acid such as p-toluenesulfonic acid was dropped, acid-added polymer (P-1-2) was formed, and this acid-added polymer also exhibited photoluminescence.

Example 42

Polymerization of 2,7-bis(4-aminophenyl)-9,9'-di-n-hexylfluorene (M-3) and 2,7-bis(4-aldehydephenyl)-9,9'-di-n-hexylfluorene (M-6) (P-2)

Under a nitrogen atmosphere, 2,7-bis(4-aminophenyl)-9,9'-di-n-hexylfluorene 0.516 g (1 mmol), 2,7-bis(4-aldehyde phenyl)-9,9'-di-n-hexylfluorene 0.542 g (1 mmol), p-toluenesulfonic acid monohydrate 0.003 g (0.016 mmol) and calcium chloride 0.336 g were introduced into 50 ml flask equipped with a stirrer and dissolved in 3 ml of hexamethylphosphoramide and 3 ml of dimethyl sulfoxide. The resulting mixture was reacted for 24 hours at room temperature and then dropped slowly into 1 L of methanol to deposit the produced polymer. The polymer was filtered, dissolved again in chloroform and then reprecipitated in methanol. The reprecipitated polymer was filtered, washed thoroughly with methanol and then dried in a vacuum oven at 40° C., thereby to obtain 0.87 g of yellow-colored polymer (yield 85.3%).

$^1$H NMR (CDCl$_3$), δ 0.79-1.1 (CH$_2$ and CH$_3$), 2.11 (br, s, CCH$_2$), 7.43-8.09 (m, aromatic), 8.64 (s, ArCH=NAr).

Example 43

Polymerization of 2,7-bis(4-aminophenyl)-9,9'-di-n-hexylfluorene (M-3) and 3,6-di-hexyloxy terephthalaldehyde (P-3)

Under a nitrogen atmosphere, 2,7-bis(4-aminophenyl)-9,9'-di-n-hexylfluorene 0.258 g (0.5 mmol), 3,6-di-hexyloxy terephthalaldehyde 0.167 g (0.5 mmol), calcium chloride 0.0176 g were introduced into a 50 ml flask equipped with a stirrer and dissolved in 1.5 ml of hexamethylphosphoramide and 1.5 ml of dimethyl sulfoxide. The resulting mixture was reacted for 24 hours at room temperature and then dropped slowly into 1 L of methanol to deposit the produced polymer. The obtained polymer was filtered, dissolved again in chloroform and reprecipitated in methanol. The reprecipitated polymer was filtered, washed thoroughly with methanol and then dried in a vacuum oven at 40° C., thereby to obtain 0.23 g of yellow-colored polymer (yield: 57.5%).

$^1$H NMR (CDCl$_3$), δ 0.74-1.85 (CH$_2$ and CH$_3$), 2.01 (br, s, CCH$_2$), 4.10 (t, —OCH$_2$), 7.43-7.80 (m, aromatic), 9.02 (s, ArCH=NAr).

Example 44

Polymerization of 2,7-bis(3-aminophenyl)-9,9'-di-n hexylfluorene (M-5) and 2,7-bis(4-aldehydephenyl)-9,9'-di-n-hexylfluorene (M-6) (p-4)

Under a nitrogen atmosphere, 2,7-bis(3-aminophenyl)-9,9'-di-n hexylfluorene 0.516 g (1 mmol), 2,7-bis(4-aldehydephenyl)-9,9'-di-n-hexylfluorene 0.542 g (1 mmol), p-toluenesulfonic acid monohydrate 0.003 g (0.016 mmol) and calcium chloride 0.336 g were introduced into a 50 ml flask equipped with a stirrer and dissolved in 3 ml of hexamethylphosphoramide and 3 ml of dimethyl sulfoxide. The resulting mixture was reacted for 24 hours at room temperature and then dropped slowly into 1 L of methanol to deposit the produced polymer. The polymer was filtered, dissolved in chloroform and reprecipitated in methanol. The reprecipitated polymer was filtered, washed thoroughly with methanol and then dried in a vacuum oven at 40° C., thereby to obtain 0.85 g of yellow-colored polymer (yield: 83.3%).

$^1$H NMR (CDCl$_3$), δ 0.74-1.1 (CH$_2$ and CH$_3$), 2.11 (br, s, CCH$_2$), 4.10 (t, —OCH$_2$), 7.54-8.09 (m, aromatic), 8.65 (s, ArCH=NAr).

Example 45

Polymerization of 2,7-bis(3-aminophenyl)-9,9'-di-n-hexylfluorene (M-5) and isophthalaldehyde (P-5)

Under a nitrogen atmosphere, 2,7-bis(3-aminophenyl)-9,9'-di-n-hexylfluorene 0.516 g (1 mmol), isophthalaldehyde 0.134 g (1 mmol), p-toluenesulfonic acid monohydrate 0.003 g (0.016 mmol) and calcium chloride 0.224 g were introduced into a 50 ml flask equipped with a stirrer and dissolved in 3 ml of hexamethylphosphoramide and 3 ml of dimethyl sulfoxide. The resulting mixture was reacted for 24 hours at room temperature and then dropped slowly into 1 L of methanol to deposit the produced polymer. The polymer was filtered, dissolved in chloroform and then reprecipitated in methanol. The reprecipitated polymer was filtered, washed thoroughly with methanol and then dried in a vacuum oven at 40° C., thereby to obtain 0.53 g of white-colored polymer (yield 86.3%).

$^1$H NMR (CDCl$_3$), δ 0.76-1.1 (CH$_2$ and CH$_3$), 2.09 (br, s, CCH$_2$), 7.54-8.52 (m, aromatic), 8.68 (s, ArCH=NAr).

Example 46

Polymerization of 1,4-bis(3-aminophenyl)-3,6-di-hexyloxy benzene (M-16) and 2,7-bis(4-aldehydephenyl)-9,9'-di-n-hexylfluorene (M-6) (P-6)

Under a nitrogen atmosphere, 1,4-bis(3-aminophenyl)-3,6-di-hexyloxy benzene 0.46 g (1 mmol) and 2,7-bis(4-aldehydephenyl)-9,9'-di-n-hexylfluorene 0.542 g (1 mmol), p-toluenesulfonic acid monohydrate 0.003 g (0.016 mmol) and calcium chloride 0.224 g were introduced into a 50 ml flask equipped with a stirrer and dissolved in 3 ml of hexamethylphosphoramide and 3 ml of dimethyl sulfoxide. The resulting mixture was reacted for 24 hours at room temperature and then dropped slowly into 1 L of methanol to deposit the produced polymer. The polymer was filtered, dissolved in chloroform and then reprecipitated in methanol. The reprecipitated polymer was filtered, washed thoroughly with methanol and then dried in a vacuum oven at 40° C., thereby to obtain 0.64 g of yellow-colored polymer (yield: 66.3%).

$^1$H NMR (CDCl$_3$)$_1$ 5 0.65-1.75 (CH$_2$ and CH$_3$), 2.09 (br, s, CCH$_2$), 4.10 (t, OCH$_2$), 6.68-8.02 (m, aromatic), 8.58 (s, ArCH=NAr).

Example 47

Polymerization of 2,7-bis(4-carboxylphenyl)-9,9'-di-n-hexylfluorene (M-11) and 3,3-dihydro oxybenzidine (P-7)

Under a nitrogen atmosphere, 2,7-bis(4-carboxylphenyl)-9,9'-di-n-hexylfluorene 1.149 g (2 mmol) and 3,3-dihydro oxybenzidine 0.432 g (2 mmol) were introduced into a 100 ml flask equipped with a stirrer and dissolved in 10 ml of phosphorus pentoxide/methanesulfonic acid (hereinafter referred to as "PPMA") and 20 ml of tetramethylenesulfone. The resulting mixture was reacted for one and a half hour at 140° C. and reacted for 3 hours after further adding 5 ml of PPMA. The reaction mixture was cooled down to room temperature and then dropped into 1 L of water to deposit the produced polymer. The polymer was washed with diluted aqueous sodium bicarbonate solution, washed with water, washed with methanol thoroughly, and then dried in a vacuum oven at 40° C., thereby to obtain 1.4 g of polymer in black (yield: 98%). The polymer was not dissolved in a typical organic solvent well.

Example 48

Polymerization of 2,7-bis(4-chlorocarbonylphenyl)-9,9'-di-n-hexylfluorene (M-12) and terephthalic dihydrazide (P-8 and P-9)

Under a nitrogen atmosphere, 2,7-bis(4-chlorocarbonylphenyl)-9,9'-di-n-hexylfluorene 0.4 g (0.65 mmol), terephthalic dihydrazide 0.126 g (0.65 mmol), lithium chloride 0.1 g were introduced into a 50 ml flask equipped with a stirrer and dissolved in 11 ml of NMP. To this mixture, pyridine 0.126 g was added, and then the resulting mixture was reacted for 4 hours at 80° C. The reaction mixture was cooled down to room temperature and then dropped into 1 L of methanol to deposit the produced polymer. The polymer was filtered, washed with water and methanol thoroughly and then dried in a vacuum oven at 40° C., thereby to obtain 0.475 g of ivory-colored polymer P-8).

$^1$H NMR (DMSO-d$_6$), δ 0.74-1.05 (CH$_2$ and CH$_3$), 2.16 (br, s, CCH$_2$), 6.68-8.02 (br, aromatic), 10.82 (s, CONH).

The obtained polymer P-8 0.2 g was dissolved in POCl$_3$ by heating, and then the solution was refluxed for 4 hours while stirring. The reaction mixture was then dropped into 1 L of water to deposit the produced polymer. The polymer was filtered, washed with methanol and then dried in a vacuum oven at 40° C., thereby to obtain yellow-colored polymer P-9. The polymer shows lower solubility, and therefore, only a small amount of the polymer was dissolved in a typical organic solvent.

Example 49

Polymerization of 2,7-bis(4-chlorocarbonylphenyl)-9,9'-di-n-hexylfluorene (M-12) and isophthalic dihydrazide (P-10 and P-11)

Under a nitrogen atmosphere, 2,7-bis(4-chlorocarbonylphenyl)-9,9'-di-n-hexylfluorene 0.8 g (1.3 mmol) and isophthalic dihydrazide 0.253 g (1.3 mmol), lithium chloride 0.15 g were introduced into a 30 ml flask equipped with a stirrer and dissolved in NMP 18 ml. Pyridine 0.252 g was added to the solution, and the resulting mixture was reacted for 4 hours at 80° C. The reaction mixture was cooled down to room temperature and then dropped into 1 L of methanol slowly to deposit the produced polymer. The polymer was filtered, washed with water and methanol, and then dried in a vacuum oven at 40° C., thereby to obtain 0.54 g of ivory-colored polymer P-12. (yield: 92%).

$^1$H NMR (DMSO-d$_6$), δ 0.62-1.03 (CH$_2$ and CH$_3$), 2.16 (br, s, CCH$_2$), 7.65-8.34 (m, aromatic), 10.82 (s, CONH).

The polymer P-12 0.3 g was dissolved in 10 ml of POCl$_3$ by heating and refluxed for 4 hours as stirring. The reaction mixture was dropped into 1 L of water to deposit the produced polymer. The polymer was filtered, washed with methanol and then dried in a vacuum oven at 40° C., thereby to obtain ivory-colored polymer P-13. The polymer shows lower solubility, and therefore, only a small amount of the polymer was dissolved in a typical organic solvent.

Example 51

Polymerization of 2,7-bis(3-chlorocarbonylphenyl)-9,9'-d-n-hexylfluorene (M-23) and isophthalic dihydrazide (P-14 and P-15)

Under a nitrogen atmosphere, 2,7-bis(3-chlorocarbonylphenyl)-9,9'-d-n-hexylfluorene 1 g (1.63 mmol), isophthalic dihydrazide 0.317 g (1.63 mmol), lithuim chloride 0.1 g were introduced into a 50 ml flask equipped with a stirrer and dissolved in 7 ml of NMP. Pyridine 0.256 g was added to the solution, and the resulting mixture was reacted for 4 hours at 80° C. The reaction mixture was cooled down to room temperature and then dropped into 1 L of methanol slowly to deposit the produced polymer. The polymer was filtered, washed with water and methanol, and then dried in a vacuum oven at 40° C., thereby to obtain 1.1 g of ivory-colored polymer P-14. (yield: 92%).

¹H NMR (DMSO-d₆), δ 0.62-1.03 (CH₂ and CH₃), 2.16 (br, s, CCH₂), 7.65-8.59 (m, aromatic), 10.82 (s, CONH).

The polymer P-14 0.4 g was dissolved in 20 ml of POCl₃ by heating and the resulting mixture was refluxed for 24 hours while stirring. The reaction mixture was dropped into 1 L of water to deposit the produced polymer. The polymer was filtered, washed with methanol and then dried in a vacuum oven at 40° C., thereby to obtain 0.38 g of ivory-colored polymer P-13. The polymer shows lower solubility, and therefore, only a small amount of the polymer was dissolved in a typical organic solvent.

Example 52

Polymerization of 2,7-bis(4-hydroxyphenyl)-9,9'-di-n-hexylfluorene (M-29) and 2,7-bis(4-chloromethylphenyl)-9,9'-di-n-hexylfluorene (M-25) (P-16)

Under a nitrogen atmosphere, 2,7-bis(4-hydroxyphenyl)-9,9'-di-n-hexylfluorene 0.44 g (0.85 mmol), 2,7-bis(4-chloromethylphenyl)-9,9'-di-n-hexylfluorene 0.50 g (0.85 mmol), benzyltriethylammonium chloride 0.04 g (0.17 mmol) were introduced into a 50 ml three-necked flask equipped with a stirrer and a reflux condenser and dissolved in a mixture of 1.7 ml of DMSO and 5.2 ml of toluene. 7 ml of 50 wt. % aqueous sodium hydroxide solution was then added to the solution. The resulting mixture was then reacted for 7 hours at 100° C. while stirring vigorously and then cooled down to room temperature. After removing aqueous layer, the organic layer was dropped into 1 L of methanol containing small amount of hydrochloric acid, thereby to deposit white-colored polymer. The polymer was filtered, washed with methanol thoroughly, dissolved in chloroform, and then reprecipitated in methanol. The reprecipitated polymer was filtered, washed with methanol and then dried in a vacuum oven at 40° C., thereby to obtain 0.75 g of white-colored polymer (yield: 85.2%).

¹H NMR (CDCl₃), δ 0.74-1.1 (CH₂ and CH₃), 2.01 (br, s, CCH₂), 5.09 (s, OCH₂C), 7.08-7.80 (m, aromatic).

Example 53

Polymerization of 2,7-bis(4-chloromethylphenyl)-9,9'-di-n-hexylfluorene (M-25) and 1,4-bis(4-hydroxystyryl)-3,6-di-hexyloxy benzene (P-17)

Under a nitrogen atmosphere, 1,4-bis(4-hydroxystyryl)-3,6-di-hexyloxy benzene 0.44 g (0.85 mmol), 2,7-bis(4-chloromethylphenyl)-9,9'-di-n-hexylfluorene 0.50 g (0.85 mmol), benzyltriethylammonium chloride 0.04 g (0.17 mmol) were introduced into a 50 ml three-necked flask equipped with a stirrer and a reflux condenser and dissolved in a mixture of 1.7 ml of DMSO and 5.2 ml of toluene. 7 ml of 50 wt. % aqueous sodium hydroxide solution was then added to the solution. The resulting mixture was reacted for 7 hours at 100° C. while stirring vigorously. The reaction mixture was then cooled down to room temperature and then dropped into 1 L of methanol containing small amount of hydrochloric acid, to deposit yellow-colored polymer. The polymer was filtered, washed with methanol thoroughly, dissolved in chloroform and then reprecipitated in methanol. The reprecipitated polymer was filtered, washed with methanol and then dried in a vacuum oven at 40° C., thereby to obtain 0.7 g of white-colored polymer (yield 79.7%).

¹H NMR (CDCl₃), δ 0.75-1.87 (CH₂ and CH₃), 2.00 (br, s, CCH₂), 4.04 (s, OCH₂), 5.09 (s, OCH₂C), 7.03-7.72 (m, aromatic).

Example 54

Polymerization of 2,7-bis(4-acetylphenyl)-9,9'-di-nhexylfluorene (M-34) and 4,4'-diamino-3,3'-dibenzoyidiphenyl ether (P-1 8 and P-1 8-1)

Under an argon atmosphere, phosphorus pentoxide 1.49 g (14.7 mmol) and m-cresol 5 ml were introduced into a round bottom flask at 0° C., and the resulting mixture was reacted for 3 hours at 110° C. to obtain a dehydrating agent. The temperature of the flask was then cooled down to room temperature, 4,4'-diamino-3,3'-dibenzoyldiphenyl ether 0.5 g (12 mmol) and 2,7-bis(4-acetylphenyl)-9,9'-di-nhexylfluorene 0.69 g (1 2 mmol) were introduced into the flask, and then 1 0 ml of m-cresol was further added to wash the wall of the flask and to dilute the reaction mixture. And then, the temperature was rapidly raised to 110° C., and then the mixture was reacted for 11 hours at that temperature. After the reaction was completed, the reaction mixture was precipitated three times in 15% triethylamine/ethanol solution and then filtered. The precipitate was washed with ethanol, water and methanol, several times, and then dried at 40° C. under a reduced pressure, thereby to obtain 0.98 g of polyquinoline P-18 (yield: 89%).

¹H NMR (CDCl₃), 10.70-1.38 ppm (m, 22H, CH₂, CH₃), 1.85-2.38 ppm (m, 4H, CCH₂), 7.10-8.60 ppm (m, 32H, aromatic).

When the P-18 polymer which has a maximum PL wavelength of 431 nm was dissolved in chloroform in a concentration of 10-5M and then concentrated hydrochloric acid was dropped onto the solution, acid-added polymer P-18-1 was formed. The P-18-1 polymer exhibited a maximum PL wavelength of 554 nm and therefore photoluminescence.

Example 55

Polymerization of 2,7-bis(4-aminophenyl)-9,9'-di-nhexylfluorene (M-3) and 6-FDA (P-19)

Under an argon atmosphere, 2,7-bis(4-aminophenyl)-9,9'-di-n-hexylfluorene 0.50 g (0.97 mmol) was introduced into a round bottom flask at room temperature and dissolved in 3 ml of N-methylpyrrolidone. 4,4'-(hexafluoroisopropylidene)diphthalic anhydride (6-FDA) 0.43 g (0.97 mmol) and 5 ml of N-methylpyrrolidone were then added to the solution. After the resulting mixture 7C was then reacted for 24 hours, pyridine 0.47 g (5.83 mmol) and acetic anhydride 0.61 g (5.83 mmol) were added to the reaction mixture, and then the resulting mixture was further reacted for 6 hours at 40° C., to form aimide. The reaction mixture was cooled down to room temperature and precipitated in a mixture of water and methanol (1/1). The precipitate was filtered, washed with methanol several times and dried at 60° C. under a reduced pressure, thereby to obtain 0.81 g of pale yellow polyimide (yield: 90.2%).

¹H NMR (CDCl₃), δ 0.74-1.45 ppm (m, 22H, CH₂, CH₃), 1.52-2.45 ppm (m, 4H, CCH₂), 7.20-8.40 ppm (m, 20H, aromatic).

Example 56

Polymerization of 2,7-bis(4-hydroxyphenyl)-9,9'-di-nhexylfluorene (M-29) and sebacoyl chloride (P-20)

Under an argon atmosphere, 2,7-bis(4-hydroxyphenyl)-9,9'-di-n-hexylfluorene 1 g (1.9 mmol) and sebacoyl chloride 0.48 g (1.9 mmol) were introduced into a round bottom flask equipped with a reflux condenser and dissolved in toluene, and then the resulting mixture was refluxed for 5 days at 120° C., to perform solution polymerization. The reaction mixture was then cooled down to room temperature, precipitated three times in methanol and then filtered. the precipitate was washed with water and methanol several times, and dried at 40° C. under a reduced pressure, thereby to obtain 1.3 g of polyester (yield: 98%).

$^1$H NMR (CDCl$_3$), δ 0.58-2.45 ppm (m, 34H, CH$_2$, CH$_3$, CCH$_2$), 2.50-2.90 ppm (m, 4H, COCH$_2$), 7.05-8.10 ppm (m, 14H, aromatic).

Example 57

Polymerization of 2,7-bis(4-hydroxystyryl)-9,9'-di-n-hexylfluorene (M-26) and decafluorobiphenyl (P-21)

Under a nitrogen atmosphere, 2,7-bis(4-hydroxystyryl)-9,9'-di-n-hexylfluorene 1.36 g (2.38 mmol) and decafluorobiphenyl 0.79 g (2.38 mmol) were introduced into a 100 ml two-necked flask and dissolved in 20 ml of DMAc, and then the resulting mixture was reacted for 17 hours at 120° C. The reaction mixture was cooled down to room temperature, dropped into 1 L of water/methanol (1/1), to give yellow-colored polymer. The polymer was filtered, dissolved in chloroform and then reprecipitated in 1 L of methanol. The reprecipitated polymer was filtered, washed thoroughly with methanol and then dried in a vacuum oven at 40° C., thereby to obtain 1.48 g of pale yellow polymer (yield: 72%).

$^1$H NMR (CDCl$_3$), δ 0.72-1.06 (CH$_2$, CH$_3$), 2.00 (br, s, CCH$_2$), 7.06-7.65 (m, vinyl, aromatic).

Example 58

Polymerization of 2,7-bis(4-hydroxystyryl)-9,9'-di-n-hexylfluorene (M-36) and 4,4'-difluorordiphenylsulfone (P-22)

Under a nitrogen atmosphere, 2,7-bis(4-hydroxystyryl)-9,9'-di-n-hexylfluorene 1.36 g (2.38 mmol), 4,4'-difluorordiphenylsulfone 0.61 g (2.38 mmol) and potassium carbonate 0.871 g (6.30 mmol) were introduced into a 100 ml two-necked flask and dissolved in 20 ml of DMAC. After the temperature was raised to 120° C., and the resulting mixture was reacted for 17 hours at that temperature. After the reaction was completed, the reaction mixture was cooled down to room temperature and then dropped slowly into 1 L of water/methanol (1/1), to give ivory-colored polymer. The polymer was filtered, dissolved in chloroform and then reprecipitated in 1 L of methanol. The reprecipitated polymer was filtered, washed thoroughly with methanol and then dried in a vacuum oven at 40° C., thereby to obtain 1.3 g of ivory-colored polymer (yield: 70%).

$^1$H NMR (CDCl$_3$), δ 0.72-1.06 (CH$_2$, CH$_3$), 2.00 (br, s, CCH$_2$), 7.04-7.92 (m, vinyl, aromatic).

Example 59

Polymerization of 2,7-bis(4-hydroxystyryl)-9,9'-di-n-hexylfluorene (M-36) and hexafluorobenzene (P-23)

Under a nitrogen atmosphere, 2,7-bis(4-hydroxystyryl)-9,9'-di-n-hexylfluorene 1.23 g (2.1 mmol), hexafluorobenzene 0.4 g (2.1 mmol) and potassium carbonate 0.871 g (6.30 mmol) were introduced into a 100 ml two-necked flask and dissolved in 20 ml of DMAc. After the temperature was raised to 120° C., the resulting mixture was reacted for 4 hours at that temperature. After the reaction was completed, the reaction mixture was cooled down to room temperature and then dropped slowly into 1 L of water/methanol (1/1), to give ivory-colored polymer. The polymer was filtered, dissolved in chloroform and then reprecipitated in 1 L of methanol. The polymer was filtered, washed thoroughly with methanol and then dried in a vacuum oven at 40° C., thereby to obtain 1.38 g of ivory-colored polymer (yield: 89.6%).

$^1$H NMR (CDCl$_3$), δ 0.55-1.16 (CH$_2$, CH$_3$), 2.00 (br, s, CCH$_2$), 7.10-8.60 (m, vinyl, aromatic).

Example 60

Polymerization of 2,7-bis(4-hydroxystyryl)-9,9'-di-n-hexylfluorene (M-36) and 4,4'-difluorobenzophenone (P-24)

Under a nitrogen atmosphere, 2,7-bis(4-hydroxystyryl)-9,9'-di-n-hexylfluorene 1.36 g (2.38 mmol), 4,4'-difluorobenzophenone 0.52 g (2.38 mmol) and potassium carbonate 0.87 g (6.30 mmol) were introduced into a 100 ml two-necked flask and dissolved in 20 ml of DMAc. After the temperature was raised to 120° C., the resulting mixture was reacted for 17 hours at that temperature. After the reaction was completed, the reaction mixture was cooled down to room temperature and then dropped slowly into 1 L of water/methanol (1/1), to give yellow-colored polymer. The polymer was filtered, dissolved in chloroform and then reprecipitated in 1 L of methanol. The polymer was filtered, washed thoroughly with methanol and then dried in a vacuum oven at 40° C., thereby to obtain 1.47 g of yellow-colored polymer (yield: 82%).

$^1$H NMR (CDCl$_3$), δ 0.60-1.12 (CH$_2$, CH$_3$), 2.00 (br, s, CCH$_2$), 7.04-7.96 (m, vinyl, aromatic).

Example 61

Polymerization of 2,7-bis(4-hydroxystyryl)-9,9'-di-n-hexylfluorene (M-36) and 2,5-bis(4-fluorophenyl)-1,3,4-oxadiazole (P-25)

Under a nitrogen atmosphere, 2,7-bis(4-hydroxystyryl)-9,9'-di-n-hexylfluorene 1.36 g (2.38 mmol), 2,5-bis(4-fluorophenyl)-1,3,4-oxadiazole 0.61 g (2.38 mmol) and potassium carbonate 0.6 g (4.34 mmol) were introduced into a 100 ml two-necked flask equipped with a dean-stock trap and dissolved in 20 ml of NMP/CHP (1/1) mixture. After the temperature was raised to 150° C., the solution was refluxed for 6 hours at that temperature to remove the moisture totally in the reaction flask. After the temperature was raised to 180° C., the resulting mixture was reacted for 20 hours. The reaction mixture was then cooled down to room temperature and diluted with NMP and then dropped slowly into 1 L of water/methanol (1/1), to give yellow-colored polymer. The polymer was filtered, washed thoroughly with acetone, hot water and methanol, sequentially, and then dried in a vacuum oven at 40° C., thereby to obtain 1.36 g of yellow-colored polymer (yield: 72.4%).

$^1$H NMR (CDCl$_3$), δ 0.58-1.24 (CH$_2$, CH$_3$), 2.00 (br, s, CCH$_2$), 7.10-8.60 (m, vinyl, aromatic).

Example 62

Polymerization of 2,7-bis(4-hydroxystyryl)-9,9'-di-n-hexylfluorene (M-36) and 4,4'-difluoroazobenzene (P-26)

Under a nitrogen atmosphere, 2,7-bis(4-hydroxystyryl)-9,9'-di-n-hexylfluorene 1.36 g (2.38 mmol), 4,4'-difluoroazobenzene 0.53 g (2.38 mmol) and potassium carbonate 0.6 g (4.34 mmol) were introduced into a 100 ml two-necked flask equipped with a dean-stock trap and dissolved in 20 ml of NMP/CHP (1/1) mixture. After the temperature was raised to 150° C., the solution was refluxed for 6 hours at that temperature to remove the moisture totally in the reaction flask. After the temperature was raised to 180° C., the resulting mixture was reacted for 20 hours. The reaction mixture was cooled down to room temperature, diluted with NMP and then dropped slowly into 1 L of water/methanol (1/1), to give yellow-colored polymer. The polymer was filtered, washed thoroughly with acetone, hot water and methanol, sequentially, and then dried in a vacuum oven at 40° C., thereby to obtain 0.71 g of yellow-colored polymer (yield: 40%).

$^1$H NMR (CDCl$_3$), δ 0.58-1.24 (CH$_2$, CH$_3$), 2.00 (br, s, CCH$_2$), 6.98-8.01 (m, vinyl, aromatic).

Example 63

Polymerization of 2,7-bis(4-hydroxyphenyl)-9,9'-di-n-hexylfluorene (M-29) and 2,5-bis(4-fluorophenyl)-1,3,4-oxadiazole (P-27)

Under a nitrogen atmosphere, 2,7-bis(4-hydroxyphenyl)-9,9'-di-n-hexylfluorene 1.0 g (1.9 mmol), 2,5-bis(4-fluorophenyl)-1,3,4-oxadiazole 0.49 g (1.9 mmol) and potassium carbonate 0.66 g (4.8 mmol) were introduced into a 100 ml two-necked flask equipped with a dean-stock trap and dissolved in 20 ml of NMP/CHP (1/1) mixture. After the temperature was raised to 150° C., the solution was refluxed for 6 hours at that temperature to remove the moisture totally in the reaction flask. After the temperature was raised to 180° C., the resulting mixture was reacted for 17 hours. The reaction mixture was cooled down to room temperature, diluted with NMP and then dropped slowly into 1 L of water/methanol (1/1), to give yellow-colored polymer. The polymer was filtered, washed thoroughly with acetone, hot water and methanol, sequentially, and then dried in a vacuum oven at 40° C., thereby to obtain 1.15 g of yellow-colored polymer (yield: 81.8%).

$^1$H NMR (CDCl$_3$), δ 0.45-1.42 (CH$_2$, CH$_3$), 1.78-2.38 (m, CCH$_2$), 7.82-8.35 (m, aromatic).

Example 64

Polymerization of 2,7-bis(4-bromophenyl)-9,9'-di-n-hexylfluorene (M-17) and sodiumsulphide (P-28)

Into a 100 ml ample flask equipped with a stirrer, 2,7-bis(4-bromophenyl)-9,9'-di-n-hexylfluorene 5 g (7.75 mmol) and sodium sulphide 0.6 g (7.75 mmol) were introduced and dissolved in 65 ml of NMP, and then the ample was sealed. After reacted for 48 hours at 200° C., the reaction mixture was cooled down to room temperature, and then the ample was then opened. The mixture was then dropped into 1 L of methanol slowly, to deposit the produced polymer. The polymer was filtered, dissolved in chloroform and then reprecipitated in methanol. The reprecipitated polymer was filtered, washed thoroughly with methanol and then dried in a vacuum oven at 40° C., thereby to obtain 3.03 g of white-colored polymer (yield: 75%).

$^1$H NMR (CDCl$_3$), δ 0.73-1.06 (m, CH$_2$, CH$_3$), 2.01 (br, s, CCH$_2$), 7.34-7.80 (m, aromatic).

Example 65

Polymerization of 2,7-bis(4-carboxylphenyl)-9,9'-di-n-hexylfluorene (M-11) and 1,4-bis(3-aminophenyl)-3,6-dihexyloxy benzene (P-29)

Under a nitrogen atmosphere, 2,7-bis(4-carboxylphenyl)-9,9'-di-n-hexylfluorene 0.718 g (1.25 mmol), 1,4-bis(3-aminophenyl)-3,6-di-hexyloxy benzene 0.575 g (1.25 mmol) and calcium chloride 0.4 g were introduced into a 50 ml flask equipped with a stirrer, and NMP 3 ml, pyridine 1 ml and triphenylphosphite 0.9 ml were added, and then the resulting mixture was reacted for 4 hours at 120° C. The reaction mixture was then cooled down to room temperature and then dropped slowly into 1 L of methanol to deposit the produced polymer. The polymer was filtered, dissolved in chloroform and then reprecipitated in methanol. The reprecipitated polymer was filtered, washed thoroughly with methanol and then dried in a vacuum oven at 40° C., thereby to obtain 1.2 g of white-colored polymer (yield: 97%).

$^1$H NMR (CDCl$_3$), δ 0.75-1.66 (CH$_2$, CH$_3$), 2.03 (br, s, CCH$_2$), 4.10 (br, —OCH$_2$), 7.03-7.99 (m, aromatic, and NH).

Example 66

Polymerization of 2,7-bis[4-(3,4-dicarboxyphenoxy)phenylenevinyl]-9,9'-di-n-hexylfluorene dianhydride (M-37) and 4,4-oxydianiline (P-30)

After 4,4-oxydianiline (ODA) 0.23 g (1.15 mmol) was introduced into a round bottom flask and dissolved in 4 ml of N-methylpyrrolidone at room temperature under an argon atmosphere, 2,7-bis[4-(3,4-dicarboxy-phenoxy)phenylenevinyl]-9,9'-di-n-hexylfluorene dianhydride 0.99 g (1.15 mmol) and N-methylpyrrolidone 7 ml were added, and then the resulting mixture was reacted for 24 hours. Pyridine 0.55 g (6.95 mmol) and acetic acid anhydride 0.71 g (6.95 mmol) were then added to the mixture, and then the mixture was further reacted for 6 hours at 40° C. to form imide. The mixture was then cooled down to room temperature and precipitated in a mixture of water and methanol (1/1). The precipitates were filtered, washed with methanol several times and then dried at 60° C. under a reduced pressure, thereby to obtain 1.02 g of pale yellow-colored polyimide (yield: 86.1%).

$^1$H NMR (CDCl$_3$), δ 0.72-1.42 (m, CH$_2$, CH$_3$), 1.62-2.38 (m, CCH$_2$), 6.75-8.10 (m, aromatic and vinyl).

Example 67

Structure analysis, and UV, PL and EL properties

Figure 2:
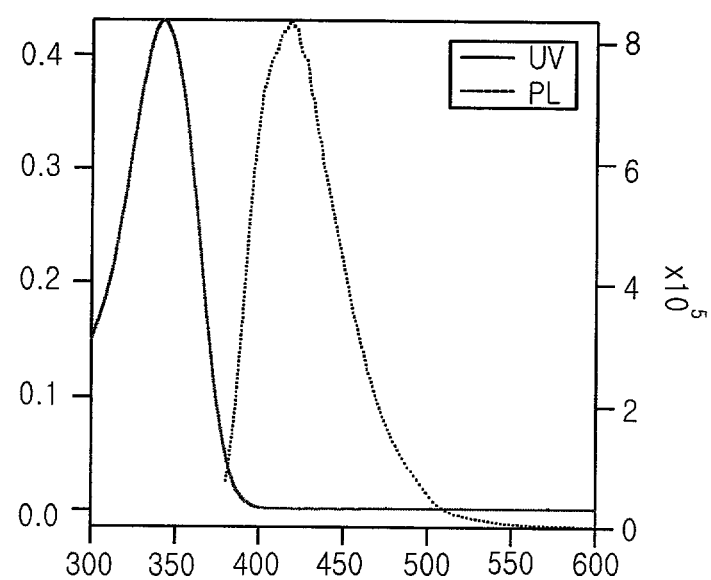
FIG. 2 shows UV-Vis and PL spectra of the monomer M-34 of Example 34.
Figure 3:
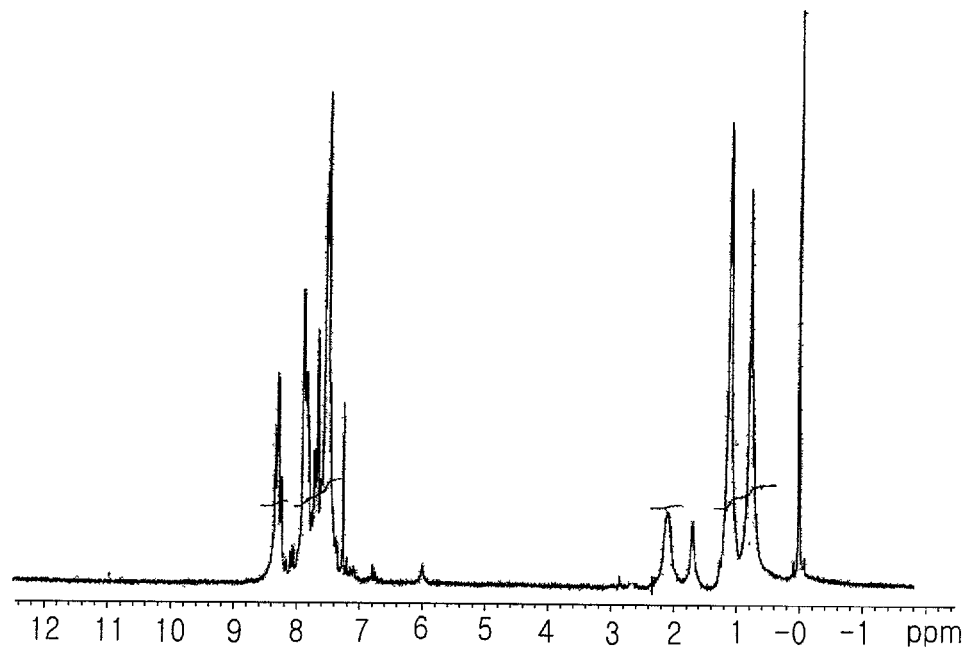
FIG. 3 shows a $^1$H NMR spectrum of the polymer P-18 of Example 54.
Figure 4:
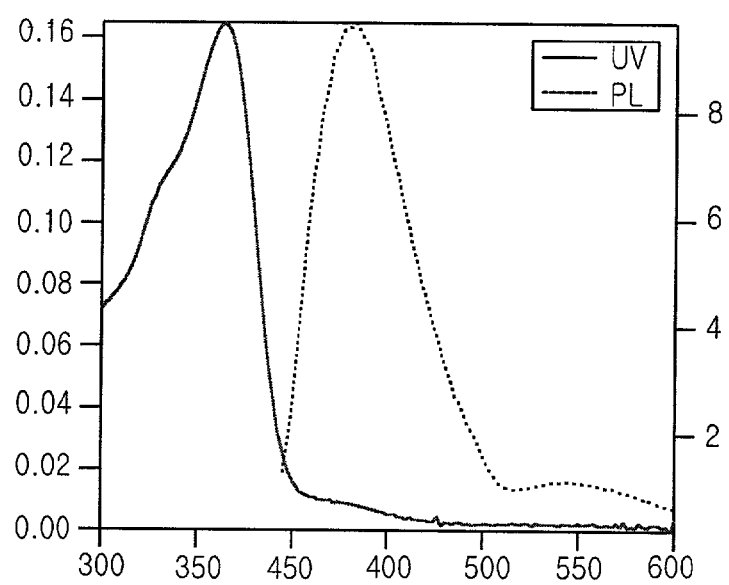
FIG. 4 shows UV-Vis and PL spectra of the polymer P-18 of Example 54.
Figure 5:
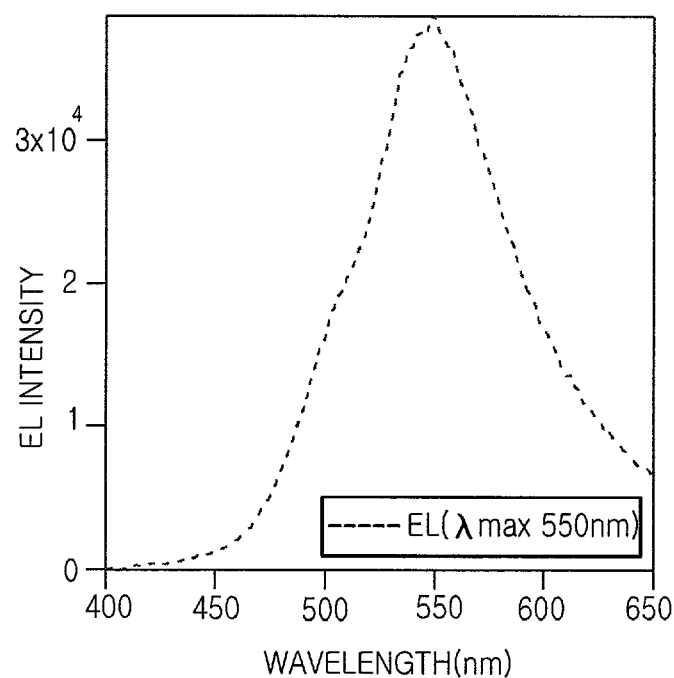
FIG. 5 shows an EL spectrum of the polymer P-18 of Example 54.
Figure 6:
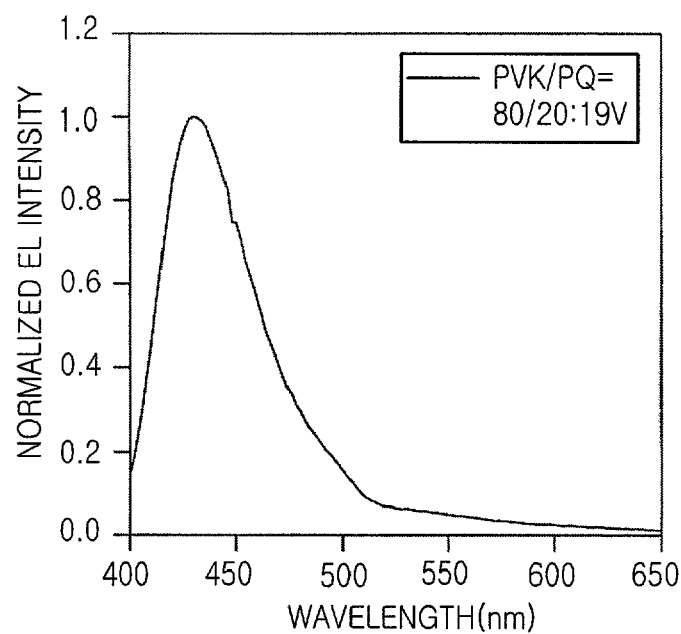
FIG. 6 shows an EL spectrum of the polymer P-18 of Example 54 which is blended with polyvinylcarbazole (polyvinylcarbazole: P-18=8:2)

FIGS. 1 and 3 show NMR spectrum of the monomer in Example 34 and of the polymer P-18 in Example 54. FIG. 2 shows ultraviolet-visible (UV-Vis) and PL spectrum of the monomer M-34 in Example 34. Thin film of polymer P-18 was formed by dissolving the polymer 0.1 g in chloroform 5 ml, filtering the obtained solution using a micro-filter of 0.2 micron in size, and then performing spin coating while controlling the spinning speed (generally in the range of 900-1200 rpm) so that the thickness of the film was to be 100 nm. The coated sample was dried at room temperature. UV spectrum was determined, and then PL spectrum was determined in the wavelength of maximum UV peak value. The results were shown in FIG. 4. EL device comprising ITO/light emitting layer/electrode was made, and its EL properties were examined. As a light emitting layer, the copolymer itself prepared in Examples as described above was used, or the blend of it in chloroform with a generally used polymer, such as polyvinylcarbazole, polymethylmethacrylate, polystyrene or epoxy resin, was used. As the electrode, aluminum was selected. The EL device was fabricated by performing vacuum deposition of aluminum onto the light emitting layer which was spin coated in a thickness of 100 nm on the ITO glass substrate, as the same manner in preparing the sample for UV-Vis or PL spectrum measurement. EL spectrum results of polymer P-18 itself and of blending it with polyvinylcarbazole are shown in FIGS. 5 and 6.

The fluorene compounds and the polymers of the present invention can be applied to LED (Light Emitting Diode), that is, an EL element. Also, the compounds and polymers of the present invention have photo and electrical activities, and therefore, show PL properties, nonlinear optical properties, and photo and electrical conductivity, whereby these can be applied to an optical switch, a sensor, a module, a wave guide, a transistor, laser, an optical absorbent, a polymer separating film, etc.

As the present invention may be embodied in several forms without departing from the spirit or essential properties thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A fluorene compound represented by the following general formula:

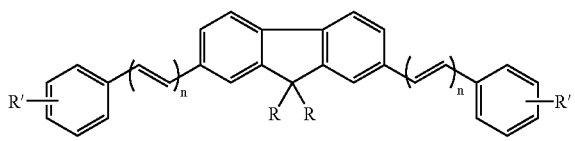

wherein R represents hydrogen, $C_1$-$C_{22}$ aliphatic alkyl or alkoxy, $C_1$-$C_{22}$ alicyclic alkyl or alkoxy, $C_6$-$C_{18}$ aryl or aryloxy, or alkyl or aryl derivatives of silicon, tin or germanium;

R' means a functional group which presents in meta- or para-position of the phenyl and is selected from the group consisting of amide, aldehyde, ketone, sulfone, sulfide, nitro, nitrile, halogen, carboxylic acid, boronic acid, hydrazide, isocyanate, urethane, carbonate, chloromethyl, anhydride, cyanate, azometine, quinoline, oxadiazole and azo, wherein R' is not bromine, provided that if R is methyl, then R' is not at para-position of phenyl; and n represents 0.

2. The compound according to claim 1, which has a maximum PL wavelength of 300 nm 600 nm.

3. The compound according to claim 1, the compound being a luminescent material for light emitting layer of an EL element.

4. The fluorene compound of claim 1, wherein R' means a functional group which presents in meta- or para-position of the phenyl and is selected from the group consisting of amide, aldehyde, ketone, sulfone, sulfide, nitro, nitrile, halogen, boronic acid, hydrazide, isocyanate, urethane, carbonate, chloromethyl, anhydride, cyanate, azometine, quinoline, oxadiazole and azo.

5. A fluorene-based polymer, comprising product formed by polymerization of the same or different fluorene compounds represented by the general formula of the fluorene compound of claim 1 or by polymerization of the fluorene compound of claim 1 and other organic compound selected from the group consisting of isophthalaldehyde, 3,6-dihexyloxyterephthaldehyde, 3,3'-dihydroxybenzidine, terephthalic dihydrazide, isophthalic dihydrazide, 1,4-bis(4-hydroxystyryl)-3,6-dihexyloxybenzene, 4,4'-diamino-3,3'-dibenzoyldiphenyl ether, 4,4'-(hexafluoroisopropylidene) diphthalic anhydride, sebacoyl chloride, decafluorobiphenyl, 4,4'-difluorodiphenylsulfone, hexafluorobenzene, 4,4'-difluorobenzophenone, 2,5-bis(4-fluorophenyl)-1,3,4-oxadiazole, 4,4'-difluoroazobenzene, 1,4-bi(3-aminophenyl)-3,6-di-hexyloxybenzene and 4,4'-oxydianiline.

6. The fluorene-based polymer according to claim 5, the fluorene-based polymer being an acid-added salt.

7. The fluorene-based polymer according tp claim 6, the fluorene-based polymer being a salt of polyazometine, polyquinoline or polyimide.

8. The fluorene-based polymer according tb claim 6, wherein the acid is hydrochloric acid or p-toluenesulfonic acid.

9. The polymer according to claim 5, the fluorene-based polymer being a luminescent material for a light emitting layer of an EL element.

10. An EL element comprising the polymer according to claim 5 as a luminescent material for a light emitting layer of an EL element that comprising an anode/light emitting layer/cathode or anode/hole transport layer/light emitting layer/cathode.

11. The EL element accordingto claim 10, wherein the luminescent material comprises a blend of the polymer according to claim 1 with polyvinylcarbazole, poly(1,4-hexyloxy-2,5-phenylenevinylene) or poly(3-hexyl-thiophene).

12. A fluorene compound represented by the following general formula:

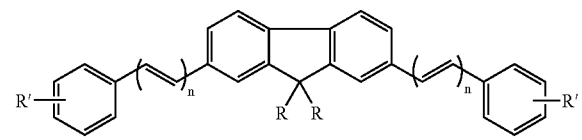

wherein R represents $C_1$-$C_{22}$ aliphatic alkyl or alkoxy, $C_1$-$C_{22}$ alicyclic alkyl or alkoxy, $C_6$-$C_{18}$ aryl or aryloxy, or alkyl or aryl derivatives of silicon, tin or germanium;

R' means a functional group which presents in meta- or para-position of the phenyl and is selected from the group consisting of amine, amide, aldehyde, ketone, sulfone, sulfide, fluoro, nitrile, halogen, carboxylic acid, boronic acid, hydrazide, isocyanate, urethane, carbonate, chloromethyl, hydroxy, anhydride, cyanate, azometine, quinoline, oxadiazole and azo; and n represents 1.

13. A fluorene-based polymer, comprising product formed by polymerization of the same or different fluorene compounds of claim 12 or by polymerization of the fluorene compound of claim 12 and other organic compound selected from the group consisting of isophthalaldehyde, 3,6-dihexyloxyterephthaldehyde, 3,3'-dihydroxybenzidine, terephthalic dihydrazide, isophthalic dihydrazide, 1,4-bis(4-hydroxystyryl)-3,6-dihexyloxybenzene, 4,4'-diamino-3,3'-dibenzoyldiphenyl ether, 4,4'-(hexafluoroisopropylidene) diphthalic anhydride, sebacoyl chloride, decafluorobiphenyl, 4,4'-difluorodiphenylsulfone, hexafluorobenzene, 4,4'-difluorobenzophenone, 2,5-bis(4-fluorophenyl)-1,3,4oxadiazole, 4,4'-difluoroazobenzene, 1,4-bi(3-aminophenyl)-3,6-di-hexyloxybenzene and 4,4'-oxydianiline.

14. The fluorene-based polymer according to claim 13, the fluorene-based polymer being an acid-added salt.

15. The fluorene-based polymer according to claim 14, the fluorene-based polymer being a salt of polyazometine, polyquinoline or polyimide.

16. The fluorene-based polymer according to claim 14, wherein the acid is hydrochloric acid or p-toluenesulfonic acid.

17. A luminescent material for light emitting layer of an EL element comprising the compound of claim 12.

18. The fluorene compound of claim 12, wherein R' means a functional group which presents in meta- or para-position of the phenyl and is selected from the group consisting of amine, amide, aldehyde, ketone, sulfone, sulfide, nitro, nitrile, halogen, boronic acid, hydrazide, isocyanate, urethane, carbonate, chloromethyl, anhydride, cyanate, azometine, quinoline, oxadiazole and azo.

19. A fluorene compound represented by the following general formula:

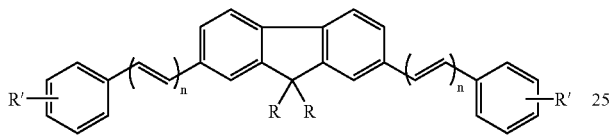

wherein R represents hydrogen, $C_1$-$C_{22}$ aliphatic alkyl or alkoxy, $C_1$-$C_{22}$ alicyclic alkyl or alkoxy, $C_6$-$C_{18}$ aryl or aryloxy, or alkyl or aryl derivatives of silicon, tin or germanium;

R' means a functional group which presents in meta-position of the phenyl and is selected from the group consisting of amide, aldehyde, ketone, sulfone, sulfide, nitro, nitrile, halogen, carboxylic acid, boronic acid, hydrazide, isocyanate, urethane, carbonate, chloromethyl, anhydride, cyanate, azometine, quinoline, oxadiazole and azo; wherein R' is not bromine, or R' means a functional group which presents in para-position of the phenyl and is selected from the group consisting of amide, aldehyde, ketone, sulfone, sulfide, nitro, nitrile, halogen, carboxylic acid, boronic acid, hydrazide, isocyanate, urethane, carbonate, chloromethyl, anhydride, cyanate, azometine, quinoline, oxadiazole and azo; wherein R' is not bromine; and n represents 0.

* * * * *